US011968893B2

(12) United States Patent
Schafer et al.

(10) Patent No.: US 11,968,893 B2
(45) Date of Patent: *Apr. 23, 2024

(54) ELECTROLUMINESCENT DEVICE

(71) Applicant: UDC IRELAND LIMITED, Dublin (IE)

(72) Inventors: Thomas Schafer, Basel (CH); Patrice Bujard, Courtepin (CH); Jonathan Rogers, White Plains, NY (US); Kristina Bardon, Waldshut (DE)

(73) Assignee: UDC Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/698,247

(22) Filed: Mar. 18, 2022

(65) Prior Publication Data

US 2022/0216422 A1    Jul. 7, 2022

Related U.S. Application Data

(63) Continuation of application No. 15/919,667, filed on Mar. 13, 2018, now Pat. No. 11,289,658, which is a continuation of application No. 13/654,550, filed on Oct. 18, 2012, now Pat. No. 9,923,148, which is a continuation of application No. 12/794,828, filed on Jun. 7, 2010, now abandoned, which is a continuation of application No. 10/531,780, filed as application No. PCT/EP03/11637 on Oct. 21, 2003, now Pat. No. 8,012,602.

(30) Foreign Application Priority Data

Oct. 30, 2002   (GB) .................................... 0225244
Jan. 31, 2003   (EP) .................................... 03405047

(51) Int. Cl.
*H10K 85/60* (2023.01)
*C07D 239/26* (2006.01)
*C07D 403/10* (2006.01)
*C09K 11/06* (2006.01)
*H10K 50/11* (2023.01)

(52) U.S. Cl.
CPC ......... *H10K 85/654* (2023.02); *C07D 239/26* (2013.01); *C07D 403/10* (2013.01); *C09K 11/06* (2013.01); C09K 2211/1018 (2013.01); H10K 50/11 (2023.02); H10K 85/6565 (2023.02)

(58) Field of Classification Search
CPC .................................................. H01L 51/0067
See application file for complete search history.

(56) References Cited

U.S. PATENT DOCUMENTS

| | | |
|---|---|---|
| 3,442,898 A | 5/1969 | Luethi |
| 4,539,507 A | 9/1985 | Vanslyke |
| 4,698,091 A | 10/1987 | Brunner |
| 5,077,142 A | 12/1991 | Sakon |
| 5,104,740 A | 4/1992 | Shinkai |
| 5,116,708 A | 5/1992 | Shikatani |
| 5,150,006 A | 9/1992 | Van Slyke |
| 5,151,629 A | 9/1992 | Vanslyke |
| 5,238,600 A | 8/1993 | Kelly |
| 5,486,406 A | 1/1996 | Shi |
| 5,518,824 A | 5/1996 | Funhoff |
| 5,597,854 A | 1/1997 | Birbaum |
| 5,629,389 A | 5/1997 | Roitman |
| 5,753,729 A | 5/1998 | Valet |
| 5,770,108 A | 6/1998 | Totani |
| 5,948,551 A | 9/1999 | Gompper |
| 6,057,048 A | 5/2000 | Hu |
| 6,225,467 B1 | 5/2001 | Esteghamatian |
| 6,280,859 B1 | 8/2001 | Onikubo |
| 6,352,791 B1 | 3/2002 | Fink |
| 6,414,104 B1 | 7/2002 | Pei |
| 8,012,602 B2 * | 9/2011 | Schafer .................. C09B 57/00 313/506 |
| 9,923,148 B2 | 3/2018 | Schafer |
| 11,289,658 B2 * | 3/2022 | Schafer .................. C09K 11/06 |
| 2002/0028329 A1 | 3/2002 | Ise |
| 2002/0121638 A1 | 9/2002 | Grushin |
| 2002/0190250 A1 | 12/2002 | Grushin |
| 2003/0197183 A1 | 10/2003 | Grushin |
| 2006/0041126 A1 | 2/2006 | Schafer |

(Continued)

FOREIGN PATENT DOCUMENTS

| | | |
|---|---|---|
| CH | 542212 | 9/1973 |
| DE | 3001188 | 7/1981 |

(Continued)

OTHER PUBLICATIONS

Anker et al. "The Action of Organo-alkali Compounds on Benzonitrile" Journal of the Chemical Society, 1941, pp. 323-331. (Year: 1941).*
Koyama et al. "Polycyclic N-Hetero Compounds. IX. Reactions of Tetralones with Formamide or Trisformylaminomethane" Chem. Pharm. Bull. 1975, 23(12), 3151-3153. (Year: 1975).*
Kreutzberger et al. "2-(Diäthylamino)pyrimidine" Arzneimittel-Forschung, 1978, vol. 28, Issue 11, pp. 2051-2054. (Year: 1978).*
Perjési et al. "Synthesis and Structure of 2-Phenyl-4-aryl-3,4,5,6-tetrahydrobenxo[h]quinazolines" Monatshefte für Chemie, 1993, 124, pp. 167-175. (Year: 1993).*
Dodson et al. "The Reaction of Amidines with α,β-Unsaturated Ketones" J. Org. Chem., 1951, 16 ,3, 461-465. (Year: 1951).*
Barluenga et al. "Reactions of N-Unsubstituted 4-amino-1-azadienes Towards Electrophiles" Synthesis, 1996, 1, 133-140. (Year: 1996).*

(Continued)

*Primary Examiner* — Peter F Godenschwager
(74) *Attorney, Agent, or Firm* — Riverside Law LLP

(57) ABSTRACT

Disclosed are electroluminescent devices that comprise organic layers that contain certain organic compounds containing one ore more pyrimidine moieties. The organic compounds containing one ore more pyrimidine moieties are suitable components of blue-emitting, durable, organo-electroluminescent layers. The electroluminescent devices may be employed for full color display panels in for example mobile phones, televisions and personal computer screens.

14 Claims, No Drawings

(56) References Cited

U.S. PATENT DOCUMENTS

| | | |
|---|---|---|
| 2006/0154105 A1 | 7/2006 | Yamamoto |
| 2010/0240892 A1 | 9/2010 | Schafer |

FOREIGN PATENT DOCUMENTS

| | | |
|---|---|---|
| DE | 3319843 | 12/1984 |
| DE | 3915804 A1 | 11/1990 |
| DE | 19809944 A1 | 10/1998 |
| EP | 0096657 | 12/1983 |
| EP | 0318423 A2 | 5/1989 |
| EP | 0563009 A1 | 9/1993 |
| EP | 0690053 | 1/1996 |
| EP | 0926216 A1 | 6/1999 |
| EP | 1013740 | 6/2000 |
| EP | 1097982 A1 | 5/2001 |
| EP | 1202608 | 5/2002 |
| JP | 2002324678 A | 11/2002 |
| JP | 2003045662 | 2/2003 |
| JP | 2004031004 | 1/2004 |
| JP | 2004095262 | 4/2004 |
| WO | 9804007 | 1/1998 |
| WO | 9947474 A1 | 9/1999 |
| WO | 0019994 A1 | 4/2000 |
| WO | 0105863 | 1/2001 |
| WO | 0202714 A2 | 1/2002 |
| WO | 2008073440 A2 | 6/2008 |

OTHER PUBLICATIONS

Mosher et al. "The Synthesis of 2,4,-Diaryl-5H-indeno- and 2,4-Diaryl-5H-pyridocyclopenta[1,2-d]pyrimidin-5-ones" J. Org. Chem., 1971, 36, 22, 3382-3385. (Year: 1971).*

Pourzal "Bortrifluorid-katalysierte [2+2'+2']-Cycloaddition von Alkynen und Nitrilen zu Pyrimidinen" Synthesis, 1983, 717-718. (Year: 1983).*

Bajic et al., "Synthesis of 2,4,6-Tris(4-N-isopropylamidinophenyl)pyrimidine trihydrochloride", Molecules, vol. 6, pp. 477-480 (2001).

Boger et al. "Thermal Cycloaddition of 1, 3, 5-triazine with Enamines: Regiospecific Pyrimidine Annulation" J. Org. Chem., 1982, 47, 2673-2675 (Year: 1982).

F. Elbe et al., 104 Journal of Physical Chemistry A, 8296-8306 (2000).

Ghosh et al. ("A Convenient Method for the Preperation of Highly Substituted Pyrimidines: Synthesis of Tri- and Tetra-Substituted Pyrimidines from 1,3-Dicarbonyl Compoundsand N,N,N'-Tris-(Triemthylsilyl)amidines" J. Heterocylcic Chem., 39, 1101 (2002) ( Year: 2002).

K.C. Gupta et al., 58 India Current Science, 1196-1198 (1989).

Lin et al. ("Formation of hexagonal columnar phases by heterocyclic pyrimidine derivatives" Liquid Crystals, 2002, vol. 29, No. 2, 237-242) (Year: 2002).

Mosher, W. A. et al., "Synthesis of 2,4-diaryl-5H-indeno- and 2,4-diaryl-5H-pyridocycopenta[1,2-d]pyrimidin-5-ones", Journal of Organic Chemistry, 1971, vol. 36, No. 22, pp. 3382-3385.

Parham et al. "2,2-Dichlorocyclopropyl Acetates as Intermediates for the Preparation of Pyrazoles and Pyrimidines" J. Org. Chem. 1969, vol. 34, No. 5, pp. 1474-1477. (Year: 1969).

Schomaker et al., "Arylation of Halogenated Pyrimidines via a Suzuki Coupling Reaction," Journal of Organic Chemistry, vol. 66, No. 21, pp. 7125-7128, Oct. 2001.

Thelakkat et al. "Low molecular weight and polymeric heterocyclics as electron transport/hole-blocking materials in organic light-emitting diodes," Polymers for Advanced Technologies, vol. 9, No. 7, pp. 429-442, Jul. 1998.

U. Ghosh et al., 39 Journal of Heterocyclic Chemistry, 1101-1104 (2002).

Vlachos, P. et al., "Electron-transporting and photopolymerisable liquid crystals", Chem. Commun., 2002, Issue 8, pp. 874-875.

Wong et al., "Suzuki Coupling Approach for the Synthesis of Phenylene-Pyrimidine Alternating Oligomers for Blue Light-Emitting Material," vol. 4, No. 4, pp. 513-516, Feb. 2002.

Wu et al., "Highly bright blue organic light-emitting devices using spirobifluorene-cored conjugated compounds," Applied Physics Letters, vol. 81, No. 4, pp. 577-579, Jul. 2002.

Y-C Lin et al., 29 Liquid Crystals 237-242 (2002).

Zambias, R. A. et al., "A convenient synthesis of 4-tert-butyl-5-benzofuranols and dihydrobenzofuranols", Journal of Organic Chemistry, 1988, vol. 53, No. 17, pp. 4135-4137.

* cited by examiner

ELECTROLUMINESCENT DEVICE

CROSS-REFERENCE TO RELATED APPLICATIONS

This application is a continuation of U S. application Ser. No. 15/919,667, filed Mar. 13, 2018, now allowed, which is a continuation of U.S. application Ser. No. 13/654,550, filed Oct. 18, 2012, now U.S. Pat. No. 9,923,148, which is a continuation of U.S. application Ser. No. 12/794,828, filed Jun. 7 2010, which is a continuation of U.S. application Ser. No. 10/531,780, filed Apr. 19, 2005. now U.S. Pat. No. 8,012,602, which is a national stage of PCT/EP2003/011637, filed Oct. 21, 2003, which claims priority to United Kingdom Application No. GB0225244.3, filed Oct. 30, 2002, and European Application No. EP03405047.6, filed Jan. 31, 2003, the contents of all foregoing documents are herein incorporated by reference.

This application is a continuation of pending U.S. application Ser. No. 12/794,828 filed Jun. 7, 2010, which is a continuation of U.S. application Ser. No. 10/531,780 filed Apr. 19, 2005 and issued as U.S. Pat. No. 8,012,602 on Sep. 6, 2011, which is a national stage of PCT/EP 2003/11637, filed Oct. 21, 2003, the contents of all foregoing documents are herein incorporated by reference.

The present invention relates to organo-electroluminescent (EL) devices, in particular EL devices that comprise durable, blue-emitting organo-electroluminescent layers. The organo-electroluminescent layers comprise certain organic compounds containing one or more pyrimidine moieties.

Progress has been made towards developing organic-based electroluminescent devices suitable for full color displays. Generally, an EL device is comprised of a light-emitting layer or layers and a pair of facing electrodes sandwiching the light-emitting layer(s). Application of an electric field between the electrodes results in the injection of electrons and holes to the system, resulting in the release of energy as light.

However, organo EL devices have not been developed that have suitable stability under continuous operation. In particular, there remains a need for blue-emitting, stable organo EL devices.

U.S. Pat. No. 5,104,740 teaches an electroluminescent element that comprises a fluorescent layer containing a coumarinic or azacoumarinic derivative and a hole transport layer, both made of organic compounds and laminated on top of the other.

U.S. Pat. No. 6,280,859 discloses certain polyaromatic organic compounds for use as a light-emitting material in organo-electroluminescent devices.

U.S. Pat. No. 5,116,708 is aimed at a hole transport material for EL devices.

WO98/04007 and EP-A-1013740 relate to an electroluminescent arrangement with the electron-conducting layer containing one or more compounds comprising triazine as basic substance.

EP-A-1013740 discloses the use of triazine compounds in EL devices.

EP-A-1,202,608 discloses EL devices comprising a carbazole compound of formula

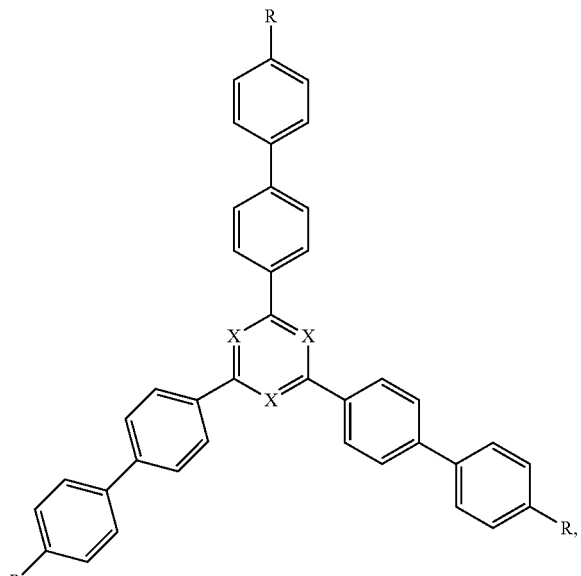

wherein R is

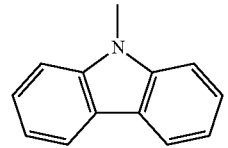

and X is C or N, which constitutes the hole transporting layer.

JP2002324678 relates to light emitting elements comprising at least one kind of compound of formula

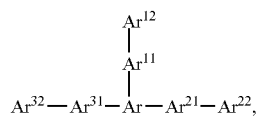

wherein
$Ar^{11}$, $Ar^{21}$ and $Ar^{31}$ denote arylene groups, $Ar^{12}$, $Ar^{22}$ and $Ar^{32}$ denote substituents or hydrogen atoms, wherein at least one of $Ar^{11}$, $Ar^{21}$, $Ar^{31}$, $Ar^{12}$, $Ar^{22}$ and $Ar^{32}$ is either a condensed ring aryl structure or a condensed ring heteroaryl structure; Ar denotes an arylene group or a heteroarylene group; and at least one amine derivative having a condensed ring group with two or more rings are contained in a luminous layer. As examples of compounds of the above formula, wherein Ar denotes a heteroarylene group the following two compounds are explicitly mentioned:

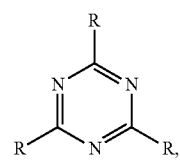

R is a group of formula

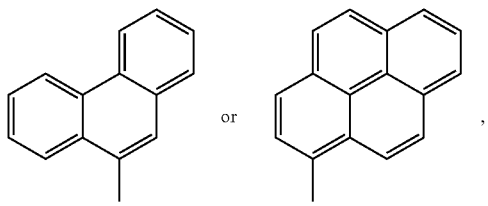

or

WO02/02714 relates to electroluminescent iridium compounds with fluorinated phenylpyridines, phenylpyrimidines, and phenylquinolines and devices made with such compounds.

U.S. Pat. No. 5,770,108 describes liquid crystal compositions comprising pyrimidine compounds of the following formula

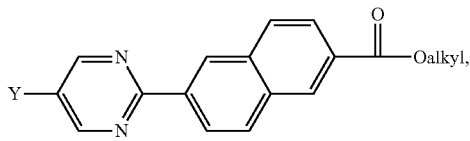

wherein Y is alkyl or —O-alkyl and liquid crystal element comprising said composition.

WO01/05863 relates to EL devices comprising arylamine-substituted poly(arylene vinylenes).

JP2000347432 describes the use of

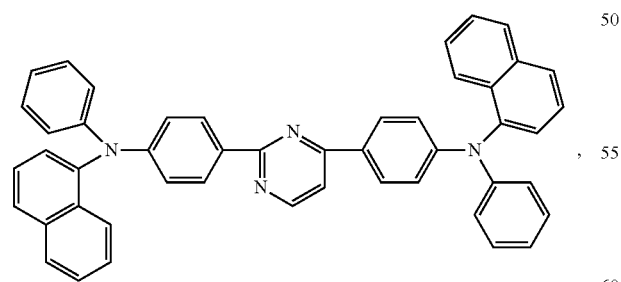

in EL devices.

EP-A-926216 relates to EL devices using triaryl amine compounds, such as

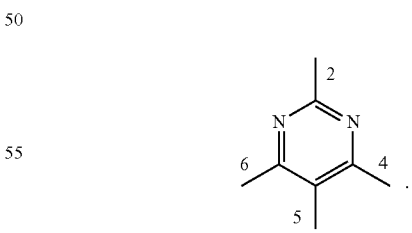

EP-A-690 053 relates to the use of conjugated compounds containing two or more pyrimidine rings, which are part of the conjugated system, as electroluminescent materials. The conjugated compounds described in EP-A-690 053 comprise pyrimidin-2,5-diyl groups which do not carry substituents at positions 4 and 6.

EP-A-563009 relates to EL devices comprising

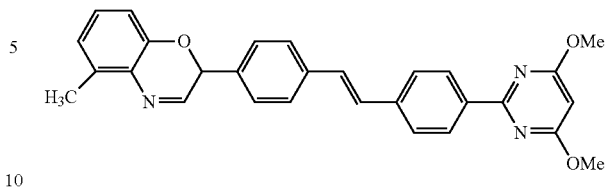

as light emitting material.

U.S. Pat. No. 5,077,142 relates to EL devices comprising a number of organic compounds as light emitting material. A pyrimidine moiety,

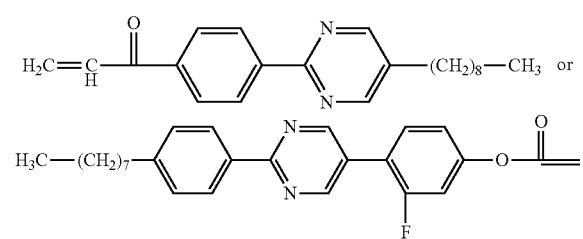

is listed among a long list of possible organic compounds.

It is the object of the present invention to provide a light emitting element with excellent light emitting characteristics and durability.

Certain organic compounds containing one or more pyrimidine moieties are found to be suitable for use in organo-electroluminescent devices. In particular, certain pyrimidine derivatives are suitable blue emitters with good durability.

The present invention is aimed at an electroluminescent device comprising an organic light-emitting layer that contains at least one blue-emitting organic compound containing one or more pyrimidine moieties.

Accordingly the present invention relates to an electroluminescent device comprising an anode, a cathode and one or a plurality of organic compound layers sandwiched therebetween, in which said organic compound layers comprise an organic compound containing one ore more pyrimidine moieties:

For example, the present organic compounds comprise one, two, three or more pyrimidine moieties, including oligomers. It is understood that the open valences in the pyrimidine moiety represents a covalent bond that is not limited in its substitution.

In general, the organic compound or compounds emit light below about 520 nm, in particular between about 380 nm and about 520 nm.

The organic compound or compounds have especially a NTSC coordinate of between about (0.12, 0.05) and about (0.16, 0.10), more especially a NTSC coordinate of about (0.14, 0.08).

The organic compound or compounds have a melting point above about 150° C., preferably above about 200° C. and most preferred above about 250° C.

For example, the organic compound is a pyrimidine compound of formula

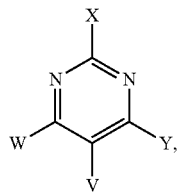
(I)

wherein

V is $C_6$-$C_{30}$aryl or $C_2$-$C_{30}$heteroaryl, which can be substituted or unsubstituted, in particular

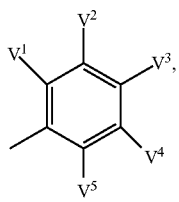

H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; —$NR^5R^6$;

W is $C_6$-$C_{30}$aryl or $C_2$-$C_{30}$heteroaryl, which can be substituted or unsubstituted, in particular

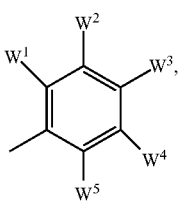

H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; —$NR^5R^6$;

Y is $C_6$-$C_{30}$aryl or $C_2$-$C_{30}$heteroaryl, which can be substituted or unsubstituted, in particular

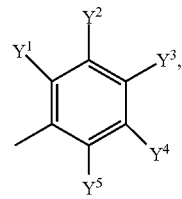

H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; —$NR^5R^6$;

X is $C_6$-$C_{30}$aryl or $C_2$-$C_{30}$heteroaryl, which can be substituted or unsubstituted, in particular

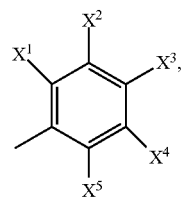

H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; —$NR^5R^6$; wherein the groups $V^1$ to $V^5$, $W^1$ to $W^5$, $X^1$ to $X^5$ and $Y^1$ to $Y^5$ are independently of each other H; halogen, $C_6$-$C_{24}$aryl; $C_6$-$C_{24}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D;

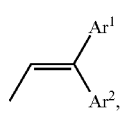

wherein $Ar^1$ is $C_6$-$C_{30}$aryl or $C_2$-$C_{30}$heteroaryl, especially phenyl, $Ar^2$ is $C_6$-$C_{30}$aryl or $C_2$-$C_{30}$heteroaryl, especially phenyl, or H, $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; —$NR^5R^6$; $C_2$-$C_{24}$ hetero-aryl; $C_2$-$C_{24}$heteroaryl which is substituted by L; —$SOR^4$; —$SO_2R^4$; —$COR^B$; —$COOR^7$; —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D; or $W^5$ or $Y^5$ together with V form a group —$CR^9_2$—, —$CR^9_2$—$CR^9_2$—, —$C(=O)CR^9_2$—, —$C(=O)$—, or —$CR^9$=$CR^9$—, or $W^5$ and $Y^5$ together with V form a group

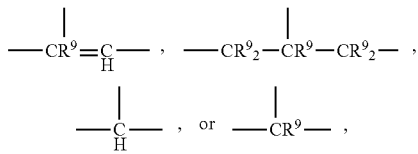

wherein $R^9$ is H; $C_1$-$C_{18}$alkyl, $C_1$-$C_{18}$alkyl which is interrupted by —O—, $C_6$-$C_{18}$aryl, $C_6$-$C_{18}$aryl which is substituted by $C_1$-$C_{18}$alkyl, or $C_1$-$C_{18}$alkoxy, or one of the substituents V, W, X, or Y is a group of the formula —Z, —Ar—Z, wherein Ar is $C_6$-$C_{24}$aryl or $C_2$-$C_{24}$heteroaryl, which can be substituted, in particular

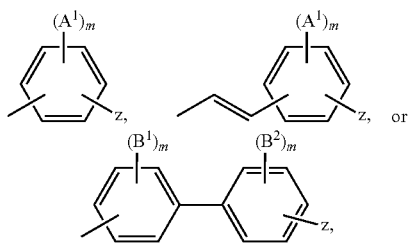

wherein Z is a group of formula

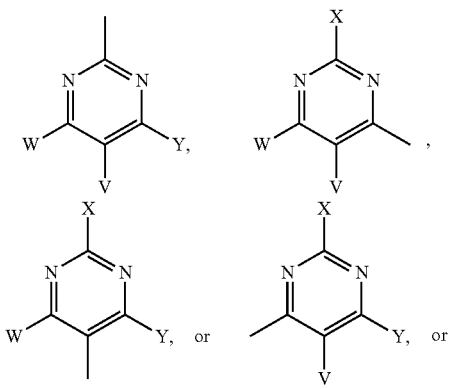

one of the substituents
$V^1$ to $V^5$, $W^1$ to $W^5$, $X^1$ to $X^5$, or $Y^1$ to $Y^5$ is a group of the formula —Z', —Ar—Z', wherein Ar is $C_6$-$C_{24}$aryl or $C_2$-$C_{24}$heteroaryl, which can be substituted, in particular

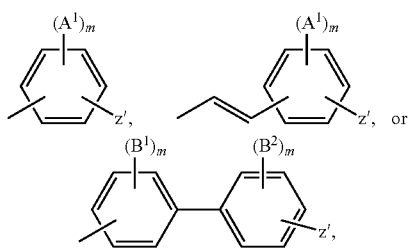

wherein Z' is a group of formula

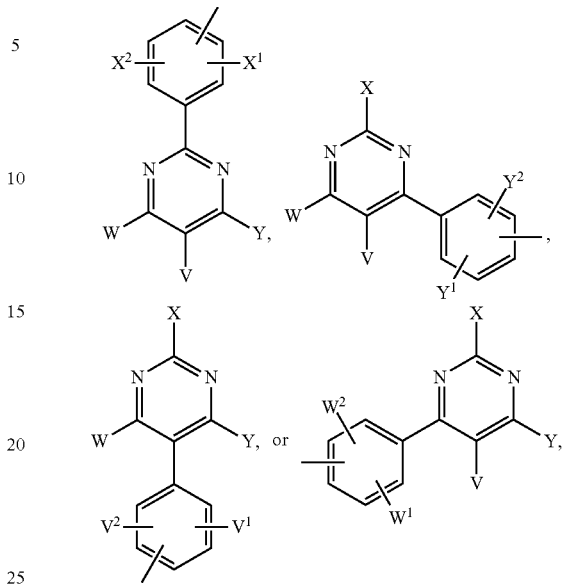

wherein
$A^1$, $B^1$ and $B^2$ are independently of each other H; $C_6$-$C_{18}$aryl; $C_6$-$C_{18}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; —$NR^5R^6$; $C_2$-$C_{18}$heteroaryl; $C_2$-$C_{18}$heteroaryl which is substituted by L; —$SOR^4$; —$SO_2R^4$; —$COR^B$; —$COOR^7$; —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D; or
two substituents $A^1$, $B^1$, $B^2$ or $B^1$ and $B^2$ form a five to seven membered ring, which can be substituted,
m is an integer of 1 to 4; and $W^1$, $W^2$, $Y^1$, $Y^2$, $X^1$, $X^2$, V, W, X and Y are as defined above;
D is —CO—; —COO—; —OCOO—; —S—; —SO—; —$SO_2$—; —O—; —$NR^5$—; —$SiR^5R^6$—; —$POR^5$—; —$CR^5$=$CR^6$—; or —C≡C—;
E is —$OR^5$; —$SR^5$; —$NR^5R^6$; —$COR^8$; —$COOR^7$; —$CONR^5R^6$; —CN; —$OCOOR^7$; or halogen, especially F;
G is E; K; heteroaryl; heteroaryl which is substituted by $C_6$-$C_{18}$aryl; $C_6$-$C_{18}$aryl which is substituted by E and/or K;
K is $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; $C_4$-$C_{18}$cycloalkyl; $C_4$-$C_{18}$cycloalkyl which is substituted by E and/or interrupted by D; $C_4$-$C_{18}$cycloalkenyl; or $C_4$-$C_{18}$cycloalkenyl which is substituted by E and/or interrupted by D;
L is E; K; $C_6$-$C_{18}$aryl; or $C_6$-$C_{18}$aryl which is substituted by G, E and/or K;
$R^4$ is $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^5$ and $R^6$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; or $R^5$ and $R^6$ together form a five or six membered ring, in particular

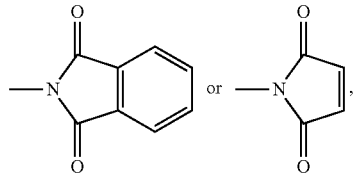

$R^7$ is H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; $C_1$-$C_{18}$alkyl which is interrupted by —O—;

$R^8$ is H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; $C_1$-$C_{18}$alkyl which is interrupted by —O—.

or two substituents selected from $V^1$ to $V^5$, $W^1$ to $W^5$, $X^1$ to $X^5$, $Y^1$ to $Y^5$ which are in neighborhood to each other form a five to seven membered ring.

Preferably at least one, more preferably at least two, most preferably at least three of the groups V, W, X and Y are $C_6$-$C_{30}$aryl or $C_2$-$C_{30}$heteroaryl, which optionally can be substituted.

Preferred are compounds of formula I, wherein Y is

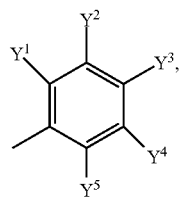

wherein $Y^1$ to $Y^5$ are as defined above and at least one of the substituents $Y^1$ to $Y^5$ is different from H; W is

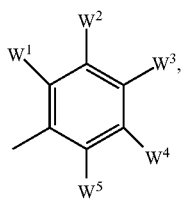

wherein $W^1$ to $W^5$ are as defined above and at least one of the substituents $W^1$ to $W^5$ is different from H; X is

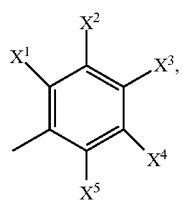

wherein $X^1$ to $X^5$ are as defined above and at least one of the substituents $X^1$ to $X^5$ is different from H, and/or V is

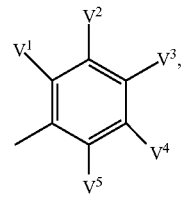

wherein $V^1$ to $V^5$ are as defined above and at least one substituent $V^1$ to $V^5$ is different from H.

In one further embodiment compounds of formula I are preferred, wherein Y is

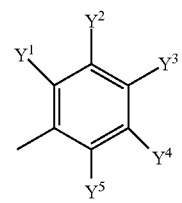

and

W is

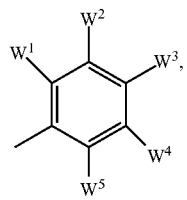

wherein $W^1$ and $W^5$ and $Y^1$ and $Y^5$ are independently of each other H; $C_1$-$C_{18}$alkyl; or $C_1$-$C_{18}$alkyl which is substituted by E and/or interrupted by D.

Examples of suitable groups Ar are

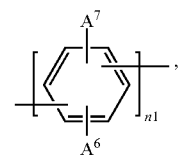

especially

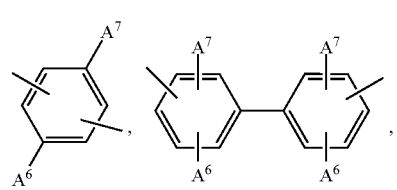

-continued
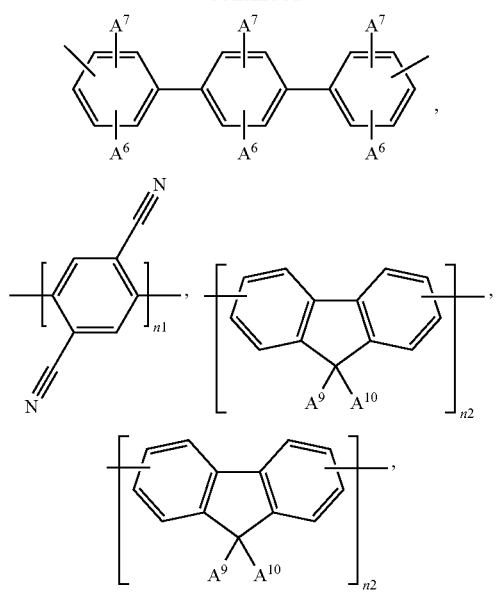
especially
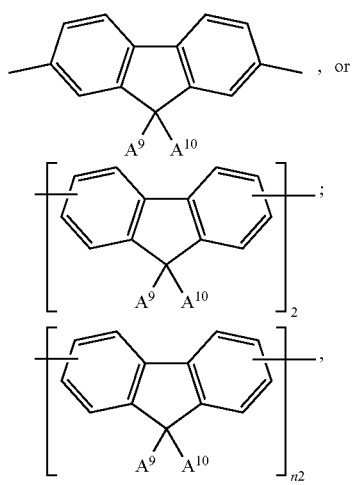, or
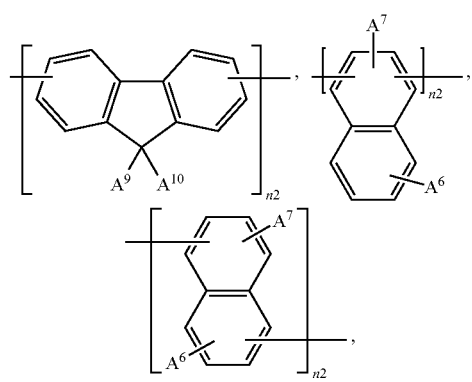
especially
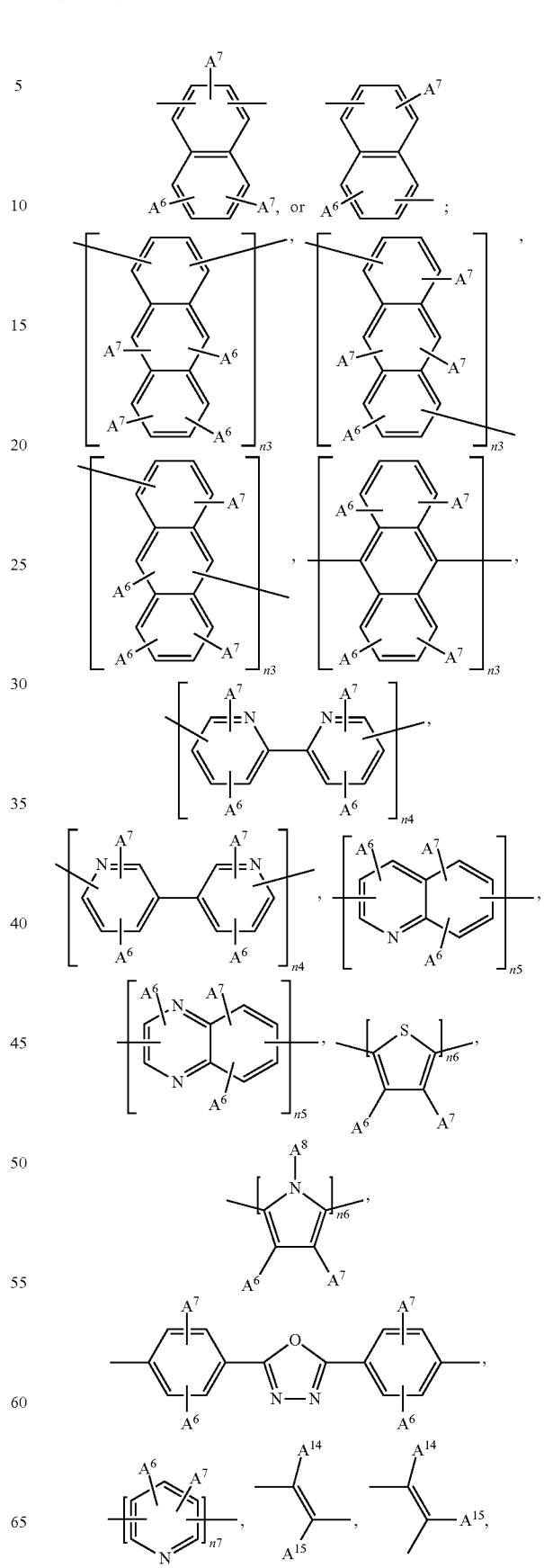

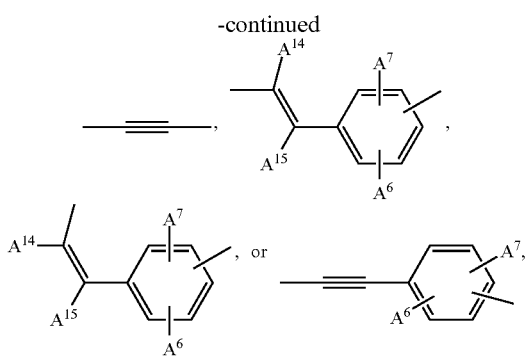

wherein
n1, n2, n3, n4, n5, n6 and n7 are integers of 1 to 10, in particular 1 to 3, $A^6$ and $A^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —CO—$R^{28}$, $A^8$ is $C_1$-$C_{18}$alkyl, $C_1$-$C_{18}$alkyl which is substituted by E and/or interrupted by D, $C_6$-$C_{24}$ aryl, or $C_7$-$C_{25}$aralkyl, $A^9$ and $A^{10}$ are independently of each other $C_1$-$C_{18}$ alkyl, $C_1$-$C_{18}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $A^9$ and $A^{10}$ form a ring, especially a five- or six-membered ring, $A^{14}$ and $A^{15}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by E, $C_2$-$C_{20}$heteroaryl, or $C_2$-$C_{20}$heteroaryl which is substituted by E, D is —CO—; —COO—; —S—; —SO—; —$SO_2$—; —O—; —$NA^{25}$—; —$SiA^{30}A^{31}$-; —$POA^{32}$-; —$CA^{23}$=$CA^{24}$-; or —C≡C—; and E is —$OA^{29}$; —$SA^{29}$; —$NA^{25}A^{26}$; —$COA^{28}$; —$COOA^{27}$; —$CONA^{25}A^{26}$; —CN; —$OCOOA^{27}$; or halogen;

wherein $A^{23}$, $A^{24}$, $A^{25}$ and $A^{26}$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

or $A^{25}$ and $A^{26}$ together form a five or six membered ring, in particular

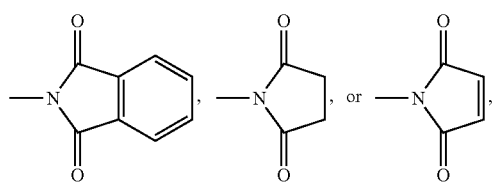

$A^{27}$ and $A^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $A^{29}$ is H; $C_6$-$C_{18}$aryl; $C_6$-$C_{18}$aryl, which is substituted by $C_1$-$C_{18}$alkyl, $C_1$-$C_{18}$alkoxy; $C_1$-$C_{18}$alkyl; or $C_1$-$C_{18}$alkyl which is interrupted by —O—, $A^{30}$ and $A^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $A^{32}$ is $C_1$-$C_{18}$alkyl, $C_6$-$C_{18}$aryl, or $C_6$-$C_{18}$aryl, which is substituted by $C_1$-$C_{18}$alkyl.

Preferably, $A^6$ and $A^7$ are independently of each other H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{18}$alkyl which is substituted by E and/or interrupted by D, such as —$CH_2OCH_3$, —$CH_2OCH_2CH_3$, —$CH_2OCH_2CH_2OCH_3$, or —$CH_2OCH_2CH_2OCH_2CH_3$, $C_6$-$C_{24}$aryl, such as phenyl, naphthyl, or biphenyl, $C_6$-$C_{24}$aryl which is substituted by E, such as —$C_6H_4OCH_3$, —$C_6H_4OCH_2CH_3$, —$C_6H_3(OCH_3)_2$, or —$C_6H_3(OCH_2CH_3)_2$, —$C_6H_4CH_3$, —$C_6H_3(CH_3)_2$, —$C_6H_2(CH_3)_3$, or —$C_6H_4$tBu.

$A^8$ is preferably H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, n-heptyl, or $C_6$-$C_{24}$aryl, such as phenyl, naphthyl, or biphenyl.

Preferably, $A^9$ and $A^{10}$ are independently of each other H, $C_1$-$C_{18}$alkyl, such as n-butyl, sec-butyl, hexyl, octyl, or 2-ethyl-hexyl, $C_1$-$C_{18}$alkyl which is substituted by E and/or interrupted by D, such as —$CH_2(OCH_2CH_2)_wOCH_3$, w=1, 2, 3, or 4, $C_6$-$C_{24}$aryl, such as phenyl, naphthyl, or biphenyl, $C_6$-$C_{24}$aryl which is substituted by E, such as —$C_6H_4OCH_3$, —$C_6H_4OCH_2CH_3$, —$C_6H_3(OCH_3)_2$, —$C_6H_3(OCH_2CH_3)_2$, —$C_6H_4CH_3$, —$C_6H_3(CH_3)_2$, —$C_6H_2(CH_3)_3$, or —$C_6H_4$tBu, or $A^9$ and $A^{10}$ together form a 4 to 8 membered ring, especially a 5 or 6 membered ring, such as cyclohexyl, or cyclopentyl.

Preferably, $A^{14}$ and $A^{15}$ are independently of each other H, $C_1$-$C_{18}$alkyl, such as as methyl, ethyl, n-propyl, iso-propyl, n-butyl, isobutyl, or sec-butyl, or $C_6$-$C_{24}$aryl, such as phenyl, naphthyl, or biphenyl.

D is preferably —CO—, —COO—, —S—, —SO—, —$SO_2$—, —O—, —$NA^{25}$-, wherein $A^{25}$ is $C_1$-$C_{18}$alkyl, such as methyl, ethyl, n-propyl, iso-propyl, n-butyl, isobutyl, or sec-butyl, or $C_6$-$C_{24}$aryl, such as phenyl, naphthyl, or biphenyl.

E is preferably —$OA^{29}$; —$SA^{29}$; —$NA^{25}A^{25}$; —$COA^{28}$; —$COOA^{27}$; —$CONA^{25}A^{25}$; or —CN; wherein $A^{25}$, $A^{27}$, $A^{28}$ and $A^{29}$ are independently of each other $C_1$-$C_{18}$ alkyl, such as methyl, ethyl, n-propyl, iso-propyl, n-butyl, isobutyl, sec-butyl, hexyl, octyl, or 2-ethyl-hexyl, or $C_6$-$C_{24}$ aryl, such as phenyl, naphthyl, or biphenyl.

Among the above-mentioned Ar the following groups are preferred:

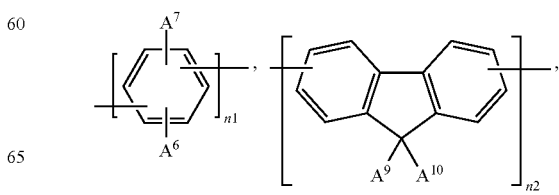

-continued

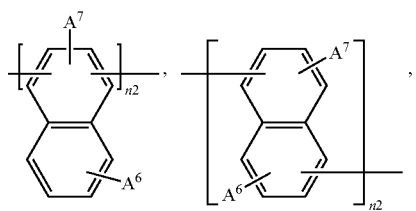

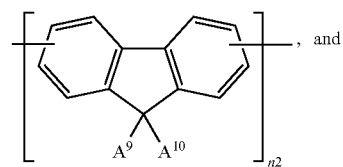

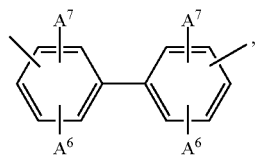

wherein the substituents are defined as above.

Preferably the electroluminescent device comprises pyrimidine compounds of formula I to VI:

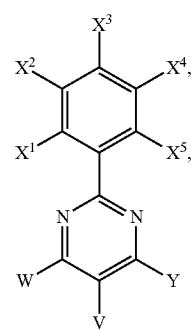
(II)

wherein V, W, Y and $X^1$ to $X^5$ are as defined above;

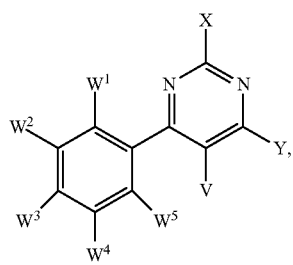
(III)

wherein V, X, Y and $W^1$ to $W^5$ are as defined above, especially

Y is $R^1$, if X is

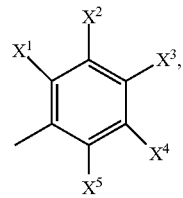

or X is $R^1$, if Y is

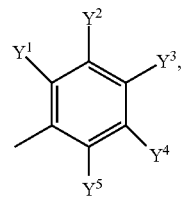

wherein $R^1$ is H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; or —$NR^5R^6$; wherein $W^1$ to $W^5$, $X^1$ to $X^5$, $Y^1$ to $Y^5$, E, D, $R^5$ and $R^6$ are as defined above, wherein most preferred $W^1$ and $W^5$ and $Y^1$ and $Y^5$ are independently of each other H; $C_1$-$C_{18}$alkyl; or $C_1$-$C_{18}$alkyl which is substituted by E and/or interrupted by D;

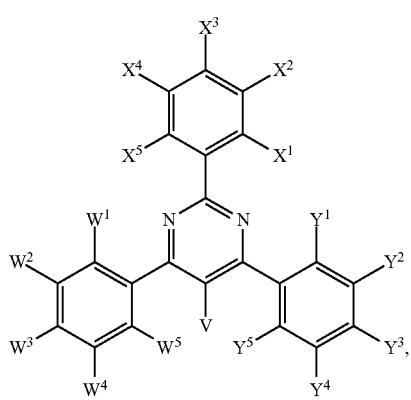
(IV)

wherein V, $W^1$ to $W^5$, $X^1$ to $X^5$ and $Y^1$ to $Y^5$ are as defined above, preferably $W^3$, $X^3$ and $Y^3$ are selected from the group consisting of $C_6$-$C_{24}$aryl; $C_6$-$C_{24}$aryl which is substituted by G; $C_2$-$C_{24}$heteroaryl; $C_2$-$C_{24}$heteroaryl which is substituted by L, $C_1$-$C_{18}$alkoxy, —$SR^5$; —$NR^5R^6$, wherein G, L, $R^5$ and $R^6$ are as defined above, V is H and/or $W^1$ and $W^5$, $Y^1$ and $Y^5$ as well as $X^1$ and $X^5$ are independently of each other H; $C_1$-$C_{18}$alkyl; or $C_1$-$C_{18}$alkyl which is substituted by E and/or interrupted by D, wherein E and D are as defined above; or (VI)

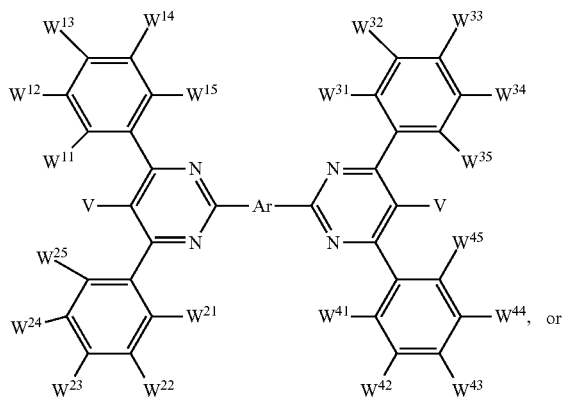

(VII)

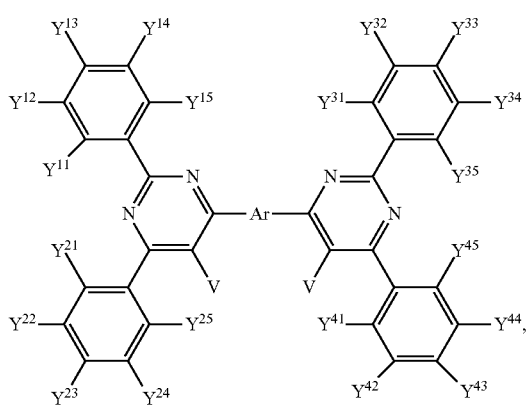

wherein
Ar is a group of formula

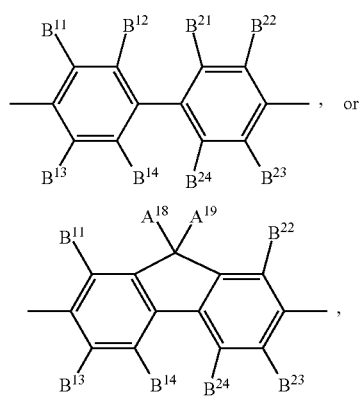

especially

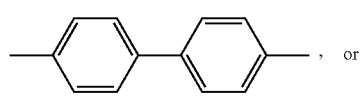, or

-continued

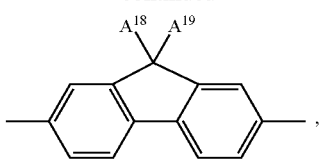, $W^{11}$ to $W^{15}$, $W^{21}$ to $W^{25}$, $W^{31}$ to $W^{35}$, $W^{41}$ to $W^{45}$, $Y^{11}$ to $Y^{15}$, $Y^{21}$ to $Y^{25}$, $Y^{31}$ to $Y^{35}$ and $Y^{41}$ to $Y^{45}$ are independently of each other H; $C_6$-$C_{24}$aryl; $C_6$-$C_{24}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; —$NR^5R^6$; $C_2$-$C_{24}$heteroaryl; $C_2$-$C_{24}$heteroaryl which is substituted by L; —$SOR^4$; —$SO_2R^4$; —$COR^8$; —$COOR^7$; —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D;

V is H; $C_6$-$C_{24}$aryl; $C_6$-$C_{24}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; or —$NR^5R^6$; $C_2$-$C_{24}$heteroaryl; $C_2$-$C_{24}$heteroaryl which is substituted by L; —$SOR^4$; —$SO_2R^4$; —$COR^B$; —$COOR^7$; —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D;

$A^{18}$ and $A^{19}$ are independently of each other H, $C_1$-$C_{18}$alkyl; $C_1$-$C_{18}$alkyl which is substituted by E and/or interrupted by D; $C_6$-$C_{18}$aryl; $C_6$-$C_{18}$aryl which is substituted by E, $B^{11}$ to $B^{14}$ and $B^{21}$ to $B^{24}$ are independently of each other H; $C_6$-$C_{18}$aryl; $C_6$-$C_{18}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; —$NR^5R^6$; $C_2$-$C_{18}$heteroaryl; $C_2$-$C_{18}$heteroaryl which is substituted by L; —$SOR^4$; —$SO_2R^4$; —$COR^B$; —$COOR^7$; or —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D; wherein D, E, G, L, $R^4$, $R^5$, $R^6$, $R^7$ and $R^8$ are as defined above, and V in formula VI or VII is preferably H.

Moreover, pyrimidine compounds of formula I are preferred, wherein V is a group of the formula

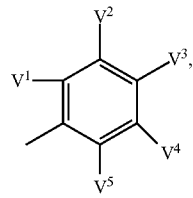

H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; or —$NR^5R^6$; and/or W is a group of the formula

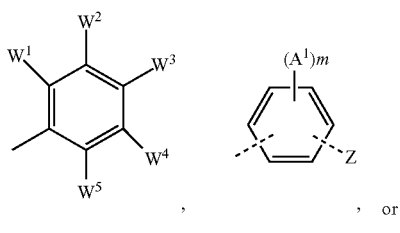

in particular

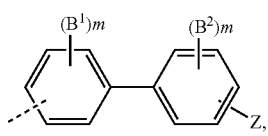

H, $C_1$-$C_{18}$alkyl; $C_1$-$C_{18}$alkyl which is substituted by E and/or interrupted by D; $C_2$-$C_{18}$alkenyl, $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy; $C_1$-$C_{18}$alkoxy which is substituted by E and/or interrupted by D; —$SR^5$; or —$NR^5R^6$; wherein $W^1$ to $W^5$, D, $V^1$ to $V^5$, E, $A^1$, $B^1$, $B^2$, $R^5$, $R^6$, m and Z are as defined above and $R^{101}$ and $R^{102}$ are independently of each other H, $C_1$-$C_8$alkyl, $C_6$-$C_{24}$aryl, or $C_5$-$C_7$cycloalkyl, in particular H or $C_{1-4}$-alkyl.

The compounds of general formula IV, VI and VII are novel and form a further subject of the present application.

In one preferred embodiment the present invention is directed to pyrimidine compounds of formula

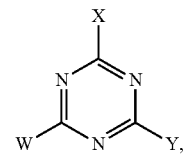

(I)

wherein
at least one of the groups W, X and Y is a group of formula

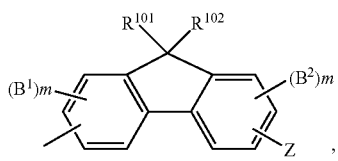

and the other groups are independently of each other an aryl group or a heteroaryl group, especially a group of formula

[structure with $R^{41}$, $R^{41'}$, $R^{42}$, $R^{42'}$, $R^{43}$]

[structure with $R^{44}$, $R^{44'}$, $R^{46}$, $R^{46'}$, $R^{45}$, $R^{45'}$, $R^{47}$, $R^{47'}$, $R^{48}$], or

[structure with $R^{11}$, $R^{11'}$, $R^{12}$, $R^{12'}$, $R^{13}$, $R^{13'}$, $R^{14}$, $R^{17'}$, $R^{17}$, $R^{16'}$, $R^{16}$, $R^{15'}$, $R^{15}$], wherein
$R^{11}$, $R^{11'}$, $R^{12}$, $R^{12'}$, $R^{13}$, $R^{13'}$, $R^{15}$, $R^{15'}$, $R^{16}$, $R^{16'}$, $R^{17}$, $R^{17'}$, $R^{41}$, $R^{41'}$, $R^{42}$, $R^{42'}$, $R^{44}$, $R^{44'}$, $R^{45}$, $R^{45'}$, $R^{46}$, $R^{46'}$, $R^{47}$ and $R^{47'}$ are independently of each other H, E, $C_6$-$C_{18}$aryl; $C_6$-$C_{18}$aryl which is substituted by E; $C_1$-$C_{18}$alkyl; $C_1$-$C_{18}$alkyl which is substituted by E and/or interrupted by D; $C_7$-$C_{18}$aralkyl; or $C_7$-$C_{18}$aralkyl which is substituted by E; or
$R^{11'}$ and $R^{12}$, $R^{12'}$ and $R^{13}$, $R^{15'}$ and $R^{16}$, $R^{16'}$ and $R^{17}$, $R^{44'}$ and $R^{46}$ and/or $R^{45'}$ and $R^{47}$ are each a divalent group $L^1$ selected from an oxygen atom, an sulfur atom, >$CR^{118}R^{119}$>$SiR^{118}R^{119}$, or

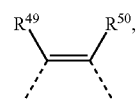

wherein
$R^{118}$ and $R^{119}$ are independently of each other $C_1$-$C_{18}$alkyl; $C_1$-$C_{18}$alkoxy, $C_6$-$C_{18}$aryl; $C_7$-$C_{18}$aralkyl;

$R^{11}$ and $R^{11'}$, $R^{12}$ and $R^{12'}$, $R^{13}$ and $R^{13'}$, $R^{13'}$ and $R^{14}$, $R^{14}$ and $R^{15}$, $R^{15}$ and $R^{15'}$, $R^{16}$ and $R^{16'}$, $R^{17'}$ and $R^{17}$, $R^{41}$ and $R^{41'}$, $R^{42}$ and $R^{42'}$, $R^{42'}$ and $R^{43}$, $R^{41'}$ and $R^{43}$, $R^{44}$ and $R^{44'}$, $R^{45}$ and $R^{45'}$, $R^{46}$ and $R^{46'}$, $R^{47}$ and $R^{47'}$, $R^{46'}$ and $R^{48}$ and/or $R^{47'}$ and $R^{48}$ are each a divalent group

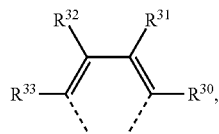

wherein
$R^{30}$, $R^{31}$, $R^{32}$, $R^{33}$, $R^{49}$ and $R^{50}$ are independently of each other H, $C_1$-$C_{18}$alkyl; $C_1$-$C_{18}$alkyl, which is substituted by E and/or interrupted by D; E; $C_6$-$C_{18}$aryl; $C_6$-$C_{18}$aryl, which is substituted by E;

$R^{14}$ is H, $C_2$-$C_{30}$heteroaryl, $C_6$-$C_{30}$aryl, or $C_6$-$C_{30}$aryl which is substituted by E, $C_1$-$C_{18}$alkyl; or $C_1$-$C_{18}$alkyl which is substituted by E and/or interrupted by D; especially

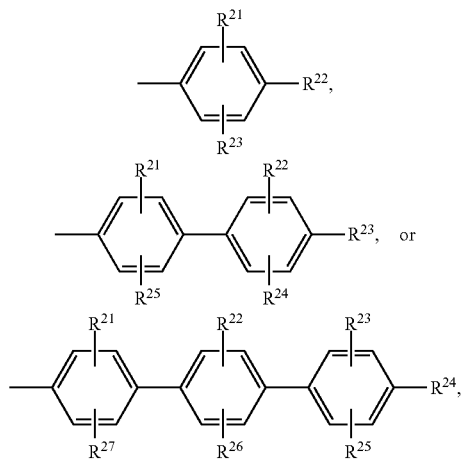

wherein $R^{21}$, $R^{22}$, $R^{23}$, $R^{24}$, $R^{25}$, $R^{26}$ and $R^{27}$ are independently of each other H, E, $C_1$-$C_{18}$alkyl; $C_1$-$C_{18}$alkyl which is substituted by E and/or interrupted by D; E; $C_7$-$C_{18}$aralkyl; $C_7$-$C_{18}$aralkyl which is substituted by E;

$R^{43}$ and $R^{48}$ are independently of each other H, E; $C_1$-$C_{18}$alkyl; $C_1$-$C_{18}$alkyl, which is substituted by E and/or interrupted by D; $C_2$-$C_{30}$heteroaryl; $C_7$-$C_{18}$aralkyl; $C_7$-$C_{18}$aralkyl which is substituted by E;

D is —CO—; —COO—; —OCOO—; —S—; —SO—; —SO$_2$—; —O—; —NR$^5$—; SiR$^5$R$^6$—; —POR$^5$—; —CR$^9$=CR$^{10}$—; or —C≡C—;

E is —OR$^5$; —SR$^5$; —NR$^5$R$^6$; —COR$^B$; —COOR$^7$; —CONR$^5$R$^6$; —CN; or halogen, especially F, or Cl;

wherein $R^5$ and $R^6$ are independently of each other $C_6$-$C_{18}$aryl; $C_6$-$C_{18}$aryl which is substituted by $C_1$-$C_{18}$alkyl, $C_1$-$C_{18}$alkyl; or $C_1$-$C_{18}$alkyl which is interrupted by —O—; or $R^5$ and $R^6$ together form a five or six membered ring, in particular

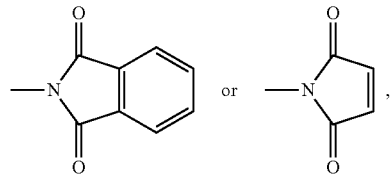

$R^7$ is $C_6$-$C_{18}$aryl; $C_6$-$C_{18}$aryl which is substituted by $C_1$-$C_{18}$alkyl, $C_1$-$C_{18}$alkyl; or $C_1$-$C_{18}$alkyl which is interrupted by —O—;
$R^8$ is $C_7$-$C_{12}$alkylaryl; $C_1$-$C_{18}$alkyl; or $C_1$-$C_{18}$alkyl which is interrupted by —O—; and
$R^9$ and $R^{10}$ are independently of each other H, $C_6$-$C_{18}$aryl; $C_6$-$C_{18}$aryl which is substituted by $C_1$-$C_{18}$alkyl, $C_1$-$C_{18}$alkyl; or $C_1$-$C_{18}$alkyl which is interrupted by —O—.

W is preferably a group of formula

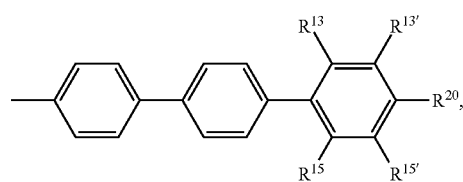

wherein
$R^{13}$, $R^{13'}$, $R^{15}$ and $R^{15'}$ are H and $R^{20}$ is H, especially

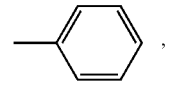

or
$R^{13}$ and $R^{15}$ are H, $R^{13'}$ and $R^{15'}$ are independently of each other H, $C_1$-$C_8$alkyl, or $C_1$-$C_8$alkoxy, and $R^{20}$ is H, $C_1$-$C_8$alkyl, or $C_1$-$C_8$alkoxy; or
$R^{13}$, $R^{15}$ and $R^{15'}$ are H, and $R^{13'}$ and $R^{20}$ are

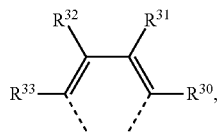

$R^{20}$, $R^{15}$ and $R^{15'}$ are H, and $R^{13}$ and $R^{13'}$ are

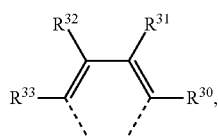

wherein
$R^{30}$, $R^{31}$, $R^{32}$ and $R^{33}$ are H, $C_1$-$C_8$alkyl, or $C_1$-$C_8$alkoxy, and
X and Y are as defined above.

According to the present invention at least one of the groups W, X and Y, preferably two of the groups W, X and Y, most preferred all three groups W, X and Y are a group of formula

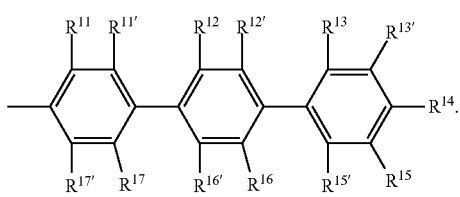

Accordingly, in one preferred embodiment of the present invention the pyrimidine compound is a compound of formula I, wherein W and Y or W and X (=X and Y) are independently of each other a group of formula

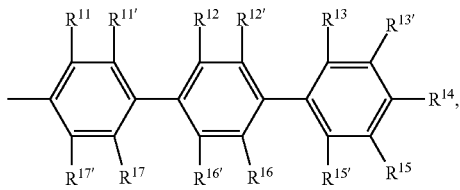

especially

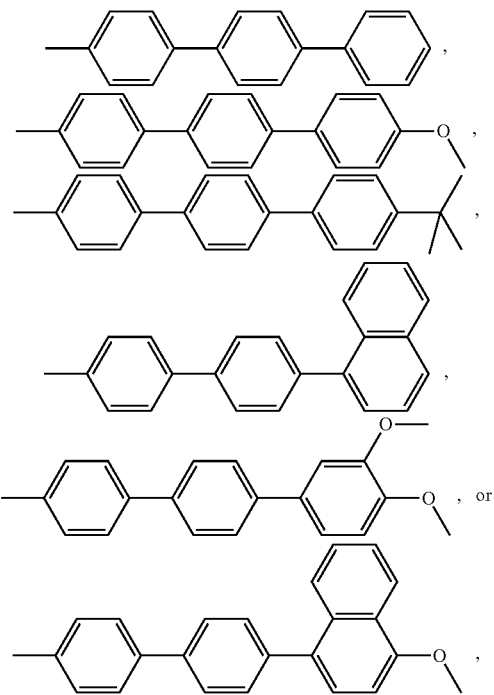

and
X is a group of formula

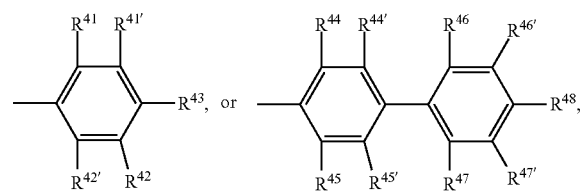

especially,

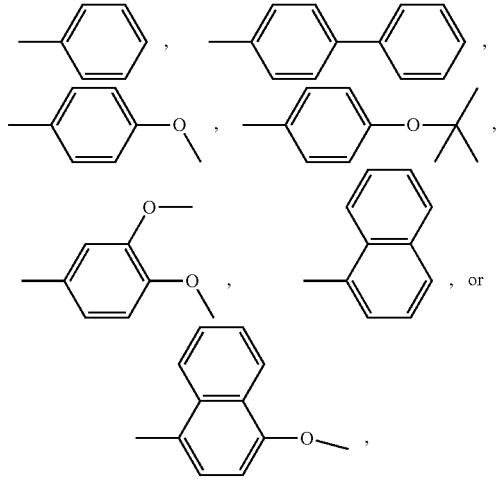

wherein $R^{11}$, $R^{11'}$, $R^{12}$, $R^{12'}$, $R^{13}$, $R^{13'}$, $R^{14}$, $R^{15}$, $R^{15'}$, $R^{16}$, $R^{16'}$, $R^{17}$, $R^{17'}$, $R^{41}$, $R^{41'}$, $R^{42}$, $R^{42'}$, $R^{44}$, $R^{44'}$, $R^{45}$, $R^{45'}$, $R^{46}$, $R^{46'}$, $R^{47}$, $R^{47'}$, $R^{43}$ and $R^{48}$ are as defined above, especially H, $C_1$-$C_8$alkyl, $C_1$-$C_8$alkoxy, or phenyl.

$R^{11}$, $R^{11'}$, $R^{12}$, $R^{12'}$, $R^{13}$, $R^{13'}$, $R^{15}$, $R^{15'}$, $R^{16}$, $R^{16'}$, $R^{17}$ and $R^{17'}$, $R^{41}$, $R^{41'}$, $R^{42}$, $R^{42'}$, $R^{44}$, $R^{44'}$, $R^{45}$, $R^{45'}$, $R^{46}$, $R^{46'}$, $R^{47}$, and $R^{47'}$ as well as $R^{14}$, $R^{43}$, and $R^{48}$ are preferably independently of each other H, E; or $C_1$-$C_8$alkyl, especially H, $C_1$-$C_4$alkyl, $C_1$-$C_4$alkoxy, or phenyl; wherein E is —$OR^5$; —$SR^5$; —$NR^5R^6$; —$COR^8$; —$COOR^7$; —$CONR^5R^6$; —CN; —$OCOOR^7$; or halogen, especially F; wherein $R^5$ and $R^6$ are independently of each other $C_6$-$C_{12}$ary, or $C_1$-$C_8$alkyl;
$R^7$ is $C_7$-$C_{12}$ alkylaryl, or $C_1$-$C_8$alkyl; and
$R^8$ is $C_6$-$C_{12}$aryl; or $C_1$-$C_8$alkyl, or
$R^{11}$ and $R^{11'}$, $R^{12}$ and $R^{12'}$, $R^{13}$ and $R^{13'}$, $R^{13}$ and $R^{14}$, $R^{41}$ and $R^{41'}$, $R^{41'}$ and $R^{43}$, $R^{44}$ and $R^{44'}$, $R^{46}$ and $R^{46'}$, $R^{46'}$ and $R^{48}$ and/or $R^{47'}$ and $R^{48}$ are each a divalent group

In one more preferred embodiment of the present invention W, X and Y are independently of each other a group of formula

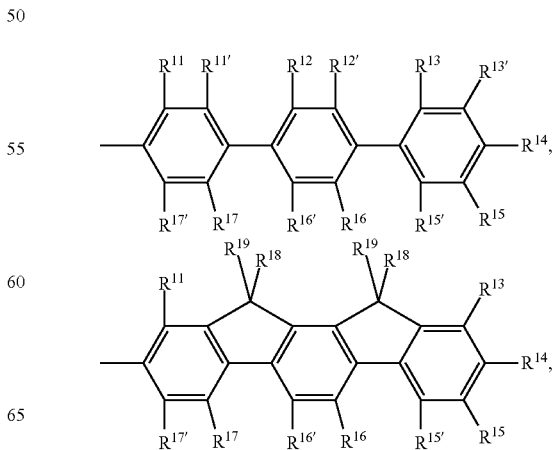

-continued

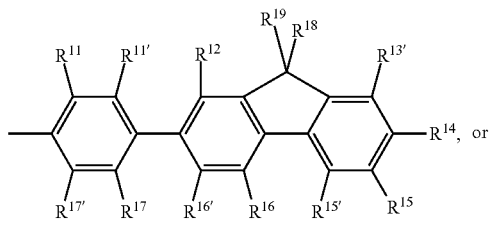

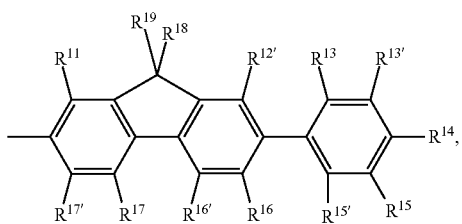

wherein
$R^{11}$, $R^{11'}$, $R^{12}$, $R^{12'}$, $R^{13}$, $R^{13'}$, $R^{15}$, $R^{15'}$, $R^{16}$, $R^{16'}$, $R^{17}$ and $R^{17'}$ are independently of each other H, $C_6$-$C_{18}$aryl; $C_6$-$C_{18}$aryl which is substituted by E; E, $C_1$-$C_1$-$C_{18}$alkyl; $C_1$-$C_{18}$alkyl which is substituted by E and/or interrupted by D; $C_7$-$C_{18}$aralkyl; $C_7$-$C_{18}$aralkyl which is substituted by E; and $R^{14}$, $R^{18}$ and $R^{19}$ are as defined above, or W is a group of the formula —$W^1$—$W^2$—$W^3$ X is a group of the formula —$X^1$—$X^2$—$X^3$ and/or Y is a group of the formula —$Y^1$—$Y^2$—$Y^3$, wherein $W^1$, $W^2$, $X^1$, $X^2$, $Y^1$ and $Y^2$ are independently of each other a group of formula

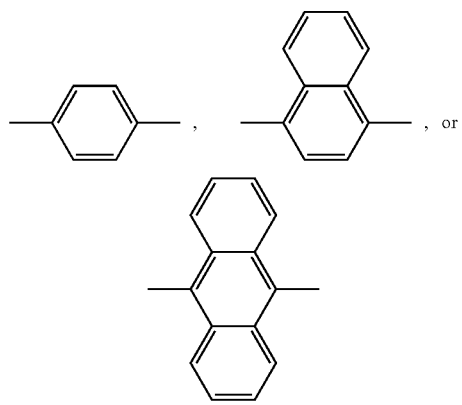

and $W^3$, $X^3$ and $Y^3$ are independently of each other a group of formula

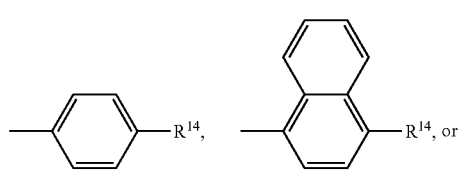

-continued

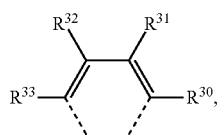

wherein $R^{14}$ is as defined above.

W, X and Y can be different, but have preferably the same meaning.

Pyrimidine compounds of formula I are preferred, wherein $R^{11}$, $R^{11'}$, $R^{12}$, $R^{12'}$, $R^{13}$, $R^{13'}$, $R^{15}$, $R^{15'}$, $R^{16}$, $R^{16'}$, $R^{17}$ and $R^{17'}$, $R^{41}$, $R^{41'}$, $R^{42}$, $R^{42'}$, $R^{44}$, $R^{44'}$, $R^{45}$, $R^{45'}$, $R^{46}$, $R^{46'}$, $R^{47}$, and $R^{47'}$ are independently of each other H, E; or $C_1$-$C_8$alkyl; wherein E is —$OR^5$; —$SR^5$; —$NR^5R^6$; —$COR^8$; —$COOR^7$; —$CONR^5R^6$; —CN; —$OCOOR^7$; or halogen; wherein $R^5$ and $R^6$ are independently of each other $C_6$-$C_{12}$aryl; or $C_1$-$C_8$alkyl;

$R^7$ is $C_7$-$C_{12}$ alkylaryl, or $C_1$-$C_8$alkyl; and $R^8$ is $C_6$-$C_{12}$aryl, or $C_1$-$C_8$alkyl.

Especially preferred are pyrimidine compounds of formula I, wherein

W, X and Y are independently of each other a group of formula

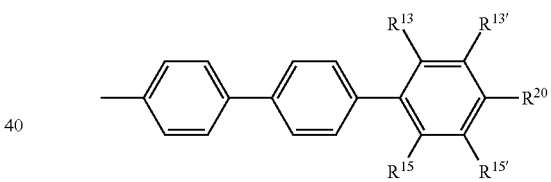

wherein $R^{13}$, $R^{13'}$, $R^{15}$ and $R^{15'}$ are H and $R^{20}$ is H, especially

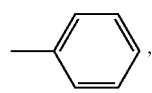

or $R^{13}$ and $R^{15}$ are H, $R^{13'}$ and $R^{15'}$ are independently of each other H, $C_1$-$C_8$alkyl, or $C_1$-$C_8$alkoxy, and $R^{20}$ is H, $C_1$-$C_8$alkyl, or $C_1$-$C_8$alkoxy; or $R^{13}$, $R^{15}$ and $R^{15'}$ are H, and $R^{13'}$ and $R^{20}$ are or $R^{20}$, $R^{15'}$ and $R^{15'}$ are H, and $R^{13}$ and $R^{13'}$ are

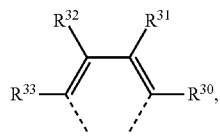

wherein
$R^{30}$, $R^{31}$, $R^{32}$ and $R^{33}$ are H, $C_1$-$C_8$alkyl, or $C_1$-$C_8$alkoxy; or
wherein
W, X and Y are independently of each other a group of formula

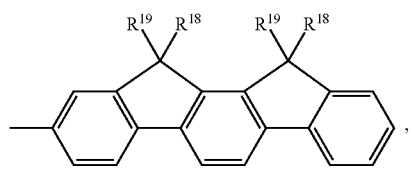

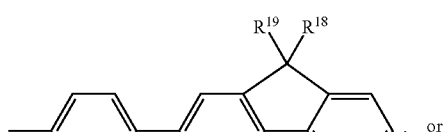

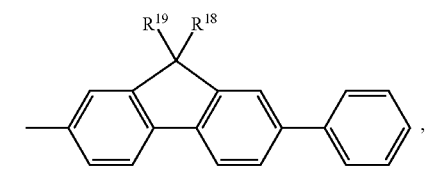

wherein $R^{18}$ and $R^{19}$ are independently of each other $C_1$-$C_8$alkyl.

In a further preferred embodiment the present invention is directed to pyrimidine compounds of formula

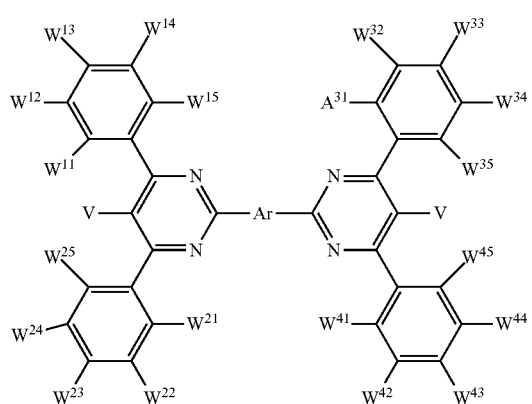

(VI)

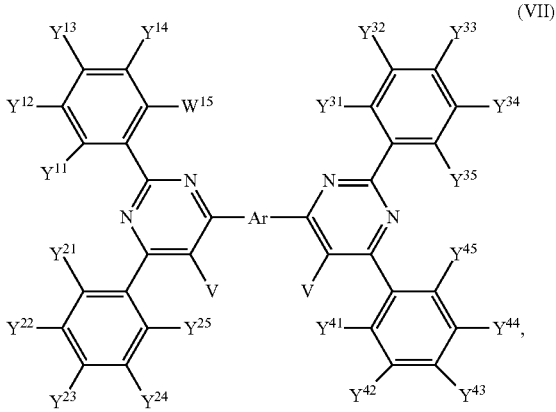

(VII)

wherein
Ar is a group of formula

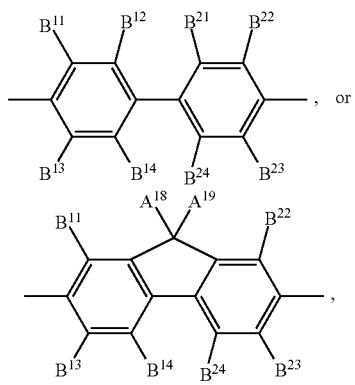

, or especially

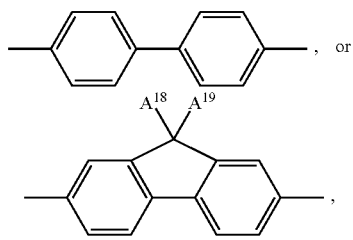

, or $W^{11}$ to $W^{15}$, $W^{21}$ to $W^{25}$, $W^{31}$ to $W^{35}$, $W^{41}$ to $W^{45}$, $Y^{11}$ to $Y^{15}$, $Y^{21}$ to $Y^{25}$, $Y^{31}$ to $Y^{35}$ and $Y^{41}$ to $Y^{45}$ are independently of each other H; $C_6$-$C_{24}$aryl; $C_6$-$C_{24}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; —$NR^5R^6$; $C_2$-$C_{24}$heteroaryl; $C_2$-$C_{24}$heteroaryl which is substituted by L; —$SOR^4$; —$SO_2R^4$; —$COR^8$; —$COOR^7$; —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D;

V is H; $C_6$-$C_{24}$aryl; $C_6$-$C_{24}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; or —$NR^5R^6$; $C_2$-$C_{24}$heteroaryl; $C_2$-$C_{24}$heteroaryl which is substituted by L; —$SOR^4$; —$SO_2R^4$; —$COR^B$; —$COOR^7$; —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D;

$A^{18}$ and $A^{19}$ are independently of each other H, $C_1$-$C_{18}$alkyl; $C_1$-$C_{18}$alkyl which is substituted by E and/or interrupted by D; $C_6$-$C_{18}$aryl; $C_6$-$C_{18}$aryl which is substituted by E, $B^{11}$ to $B^{14}$, $B^{21}$ to $B^{24}$, $B^{31}$ to $B^{34}$ and $B^{41}$ to $B^{44}$ are independently of each other H; $C_6$-$C_{18}$aryl; $C_6$-$C_{18}$aryl which is substituted by G; $C_1$-$C_{18}$alkyl; $C_1$-$C_{18}$alkyl which is substituted by E and/or interrupted by D; $C_7$-$C_{18}$alkylaryl; $C_7$-$C_{18}$alkylaryl which is substituted by E and/or interrupted by D; $C_2$-$C_{18}$alkenyl; $C_2$-$C_{18}$alkenyl which is substituted by E and/or interrupted by D; $C_2$-$C_{18}$alkynyl; $C_2$-$C_{18}$alkynyl which is substituted by E and/or interrupted by D; $C_1$-$C_{18}$alkoxy, $C_1$-$C_{18}$alkoxy which is substituted by E and/or interrupted by D; —$SR^5$; —$NR^5R^6$; $C_2$-$C_1$heteroaryl; $C_2$-$C_{18}$heteroaryl which is substituted by L; —$SOR^4$; —$SO_2R^4$; —$COR^B$; —$COOR^7$; or —$CONR^5R^6$; $C_4$-$C_{18}$cycloalkyl; $C_4$-$C_{18}$cycloalkyl which is substituted by E and/or interrupted by D; $C_4$-$C_{18}$cycloalkenyl; $C_4$-$C_{18}$cycloalkenyl which is substituted by E and/or interrupted by D; wherein D, E, G, L, $R^4$, $R^5$, $R^6$, $R^7$ and $R^3$ are as defined above.

In a preferred embodiment W and Y are groups of the formula

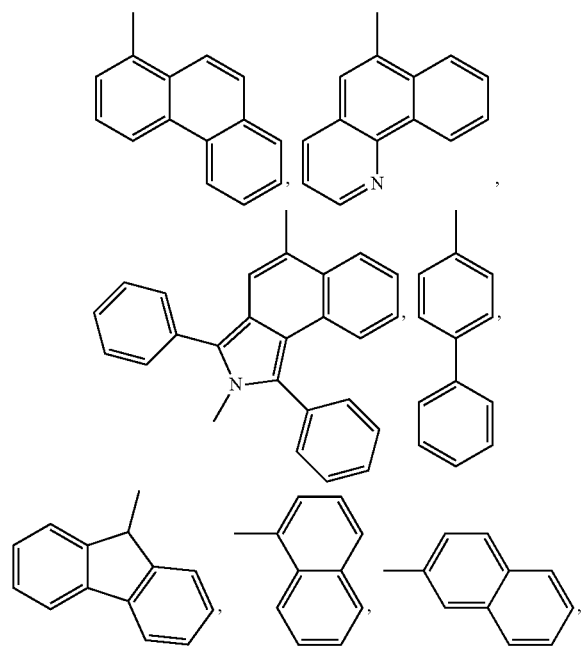

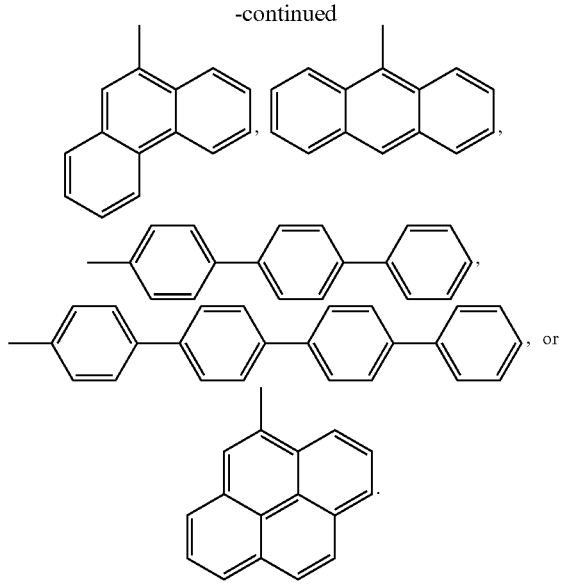

Particularly preferred are pyrimidine compounds of the following formula:

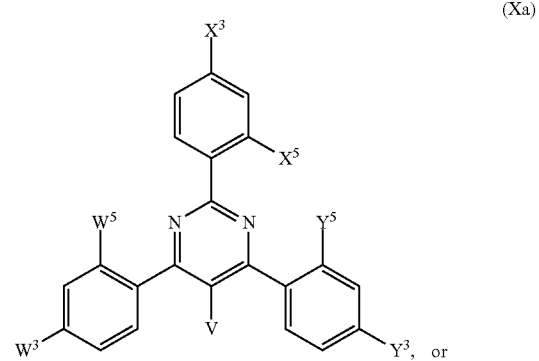

(Xa)

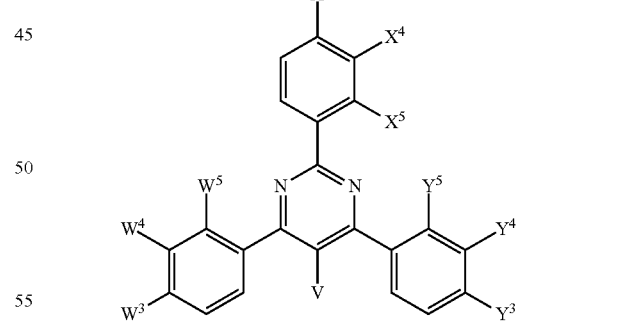

(Xb)

wherein V is H, or $C_1$-$C_8$-alkyl, $X^3$ and $X^4$ are independently of each other H, $C_1$-$C_8$alkyl, $C_1$-$C_8$alkoxy, $C_1$-$C_8$thioalkyl, or phenyl, $X^5$ is H, or $C_1$-$C_8$alkoxy, $W^5$ is H, $C_1$-$C_8$alkyl, or $O(CH_2)_{n1}$—X, $Y^5$ is H, $C_1$-$C_8$alkyl, or $O(CH_2)_{n1}$—X, $Y^3$, $Y^4$, $W^3$ and $W^4$ are independently of each other $C_1$-$C_8$alkyl, $C_1$-$C_8$alkoxy, $C_1$-$C_8$thioalkyl, halogen, in particular Br, phenyl, or $O(CH_2)_{n1}$—X, wherein n1 is an integer of 1 to 5 and X is —O—$(CH_2)_{m1}CH_3$, —OC(O)—(CH$_2$)$_{m1}$CH$_3$, —C(O)—O—C$_1$-C$_8$alkyl, —NR$^{103}$R$^{104}$, wherein m1 is an integer of 0 to 5 and R$^{103}$ and R$^{104}$ are independently of each other H, or C$_1$-C$_8$-alkyl, or R$^{103}$ and R$^{104}$ together form a five or six membered heterocyclic ring, in particular

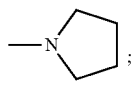

(XI)

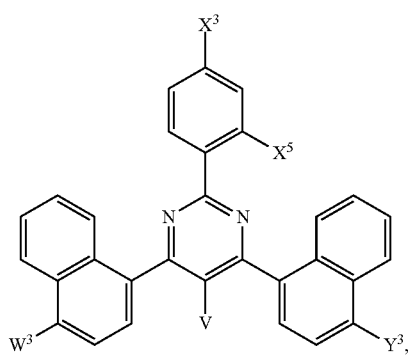

wherein V is H, or C$_1$-C$_8$alkyl,
W$^3$ is H, C$_1$-C$_8$alkyl, or C$_1$-C$_8$alkoxy,
X$^3$ is H, C$_1$-C$_8$alkoxy, phenyl or O(CH$_2$)$_{n1}$—X,
X$^5$ is H, C$_1$-C$_8$alkoxy, phenyl or O(CH$_2$)$_{n1}$—X,
Y$^3$ is H, C$_1$-C$_8$alkyl, or C$_1$-C$_8$alkoxy, wherein n1 is an integer of 1 to 4 and X is —O—(CH$_2$)$_{m1}$CH$_3$, —OC(O)—(CH$_2$)$_{m1}$CH$_3$, —C(O)—O—C$_1$-C$_8$alkyl, wherein m1 is an integer of 0 to 5;

(XIIa)

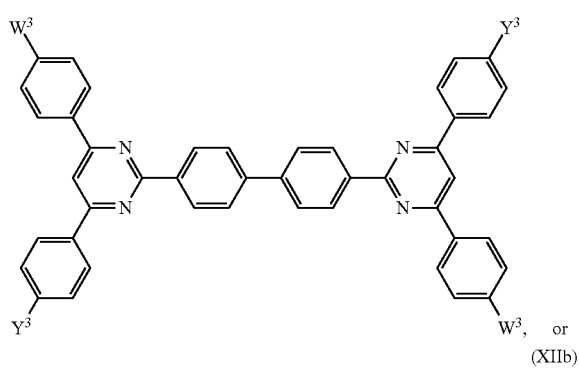

or (XIIb)

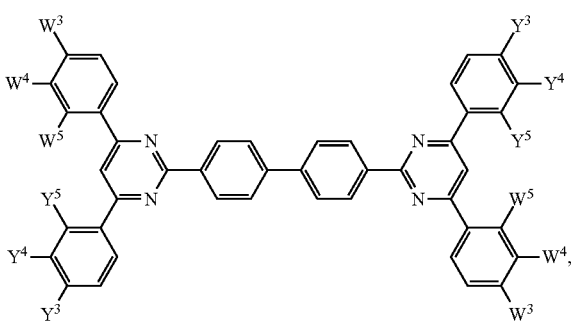

wherein W$^3$ and W$^4$ are independently of each other H, —NR$^{103}$R$^{104}$, C$_1$-C$_8$thioalkyl, or C$_1$-C$_8$alkoxy,
Y$^3$ and Y$^4$ are independently of each other H, —NR$^{103}$R$^{104}$, C$_1$-C$_8$thioalkyl, or C$_1$-C$_8$alkoxy, wherein R$^{103}$ and R$^{104}$ are independently of each other H, or C$_1$-C$_8$alkyl.
W$^5$ is H, C$_1$-C$_8$alkyl, or O(CH$_2$)$_{n1}$—X,
Y$^5$ is H, C$_1$-C$_8$alkyl, or O(CH$_2$)$_{n1}$—X,
wherein n1 is an integer of 1 to 5 and X is —O—(CH$_2$)$_{m1}$CH$_3$, —OC(O)—(CH$_2$)$_{m1}$CH$_3$, —C(O)—O—C$_1$-C$_8$alkyl, —NR$^{103}$R$^{104}$, wherein m1 is an integer of 0 to 5 and R$^{103}$ and R$^{104}$ are independently of each other H, or C$_1$-C$_8$-alkyl, or R$^{103}$ and R$^{104}$ together form a five or six membered heterocyclic ring, in particular

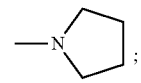

(XIII)

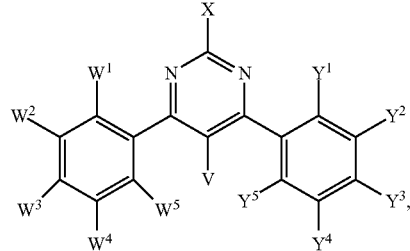

wherein V, W$^1$ to W$^5$, X, Y$^1$ to Y$^5$ are as defined above, wherein V is preferably

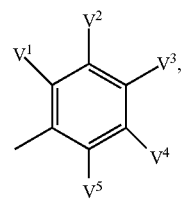

with the proviso that at least one substituent V$^1$ to V$^5$ is different from hydrogen;

(XIVa)

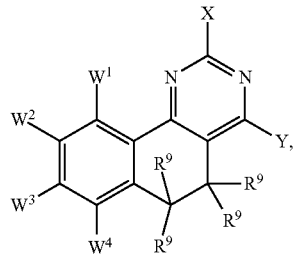

(XIVb)

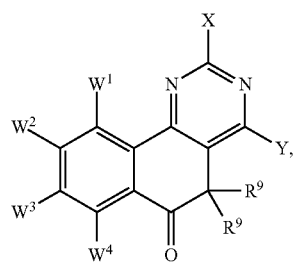

(XIVc)

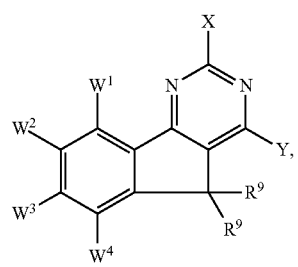

(XIVd)

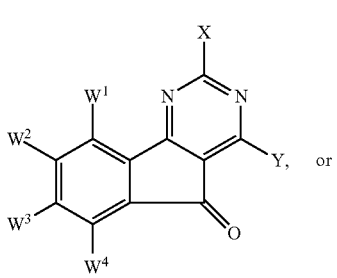

(XIVe)

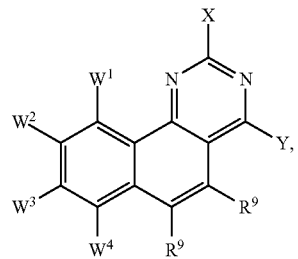

wherein X, Y, $W^1$ to $W^4$, and $R^9$ are as defined above;

(XV)

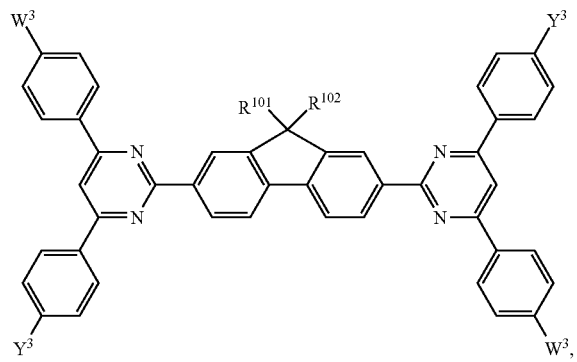

wherein $W^3$ is H, $-NR^{103}R^{104}$, $C_1$-$C_8$thioalkyl, or $C_1$-$C_8$alkoxy, $Y^3$ is H, $-NR^{103}R^{104}$, $C_1$-$C_8$thioalkyl, or $C_1$-$C_8$alkoxy, wherein $R^{103}$ and $R^{104}$ are independently of each other H, or $C_1$-$C_8$alkyl, $R^{101}$ and $R^{102}$ are independently of each other H, $C_1$-$C_8$alkyl, phenyl, or $C_5$-$C_7$cycloalkyl, in particular cyclohexyl;

(XVI)

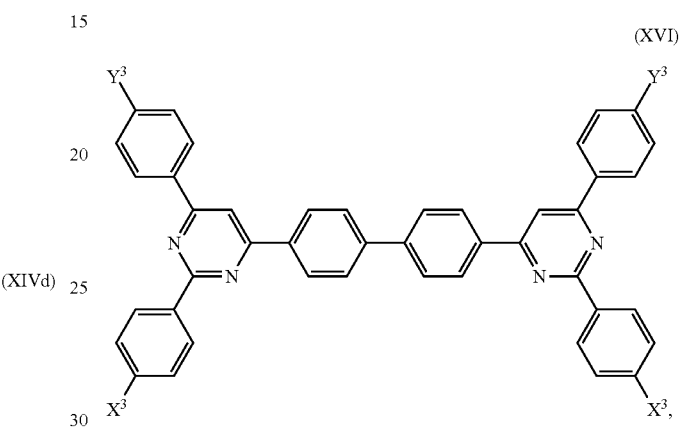

wherein $Y^3$ is H, $-NR^{103}R^{104}$, $C_1$-$C_8$thioalkyl, or $C_1$-$C_8$alkoxy, $X^3$ is H, $-NR^{103}R^{104}$, $C_1$-$C_8$thioalkyl, or $C_1$-$C_8$alkoxy, wherein $R^{103}$ and $R^{104}$ are independently of each other H, or $C_1$-$C_8$alkyl;

(XVII)

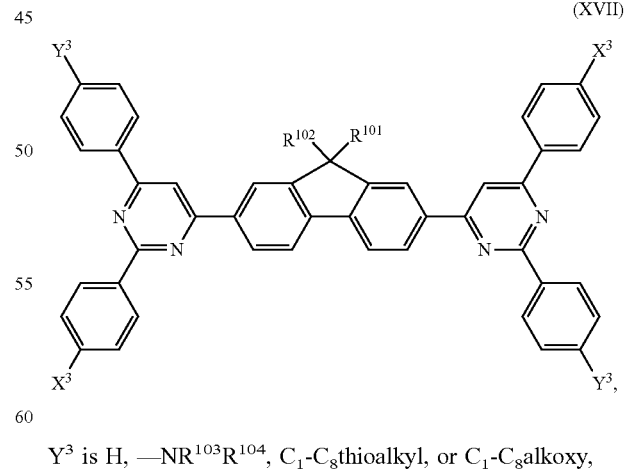

$Y^3$ is H, $-NR^{103}R^{104}$, $C_1$-$C_8$thioalkyl, or $C_1$-$C_8$alkoxy, $X^3$ is H, $-NR^{103}R^{104}$, $C_1$-$C_8$thioalkyl, or $C_1$-$C_8$alkoxy, wherein $R^{103}$ and $R^{104}$ are independently of each other H, or $C_1$-$C_8$alkyl, $R^{101}$ and $R^{102}$ are independently of each other H, $C_1$-$C_8$alkyl, phenyl, or $C_5$-$C_7$cycloalkyl, in particular cyclohexyl;

pyrimidine compounds of formula

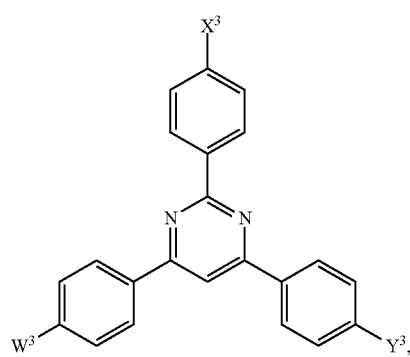
(XVIII)

wherein $W^3$ and $Y^3$ are a group of formula

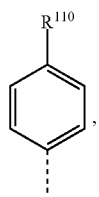

wherein $R^{110}$ is $C_6$-$C_{10}$-aryl, such as phenyl, 1-naphthyl, 2-naphthyl, 3- or 4-biphenyl, 9-phenanthryl, 2- or 9-fluorenyl, which is optionally substituted by $C_1$-$C_6$-alkyl, or $C_1$-$C_4$-alkoxy, especially

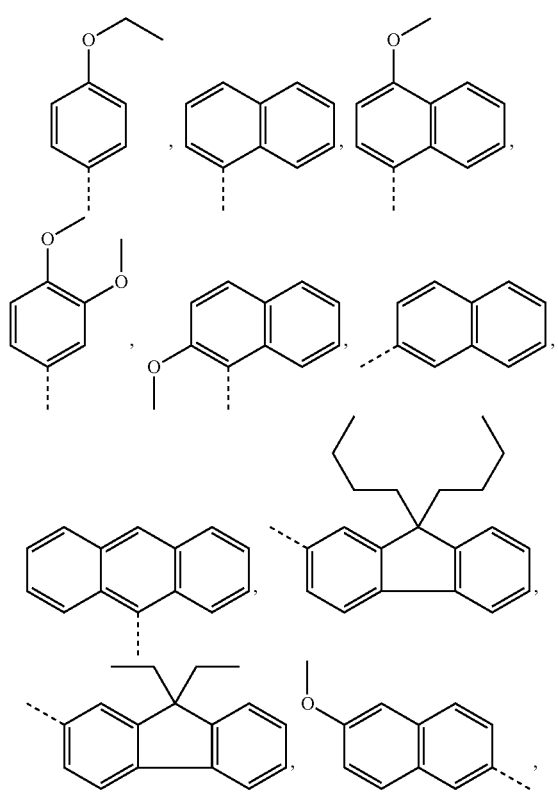

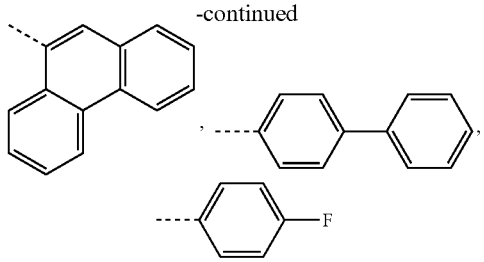

or $C_4$-$C_{10}$ heteroaryl, especially

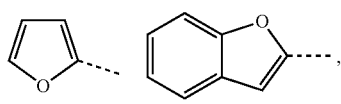

and
$X^3$ is H, $C_1$-$C_6$-alkyl, $C_1$-$C_4$-alkoxy, Ph, or

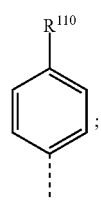

and
pyrimidine compounds of formula I, wherein
V is hydrogen,
W and Y are independently of each other a group of formula

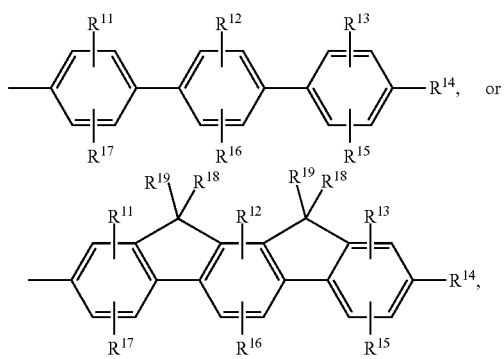

and
X is a group of formula

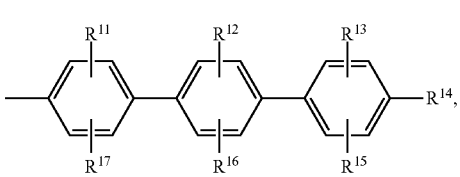

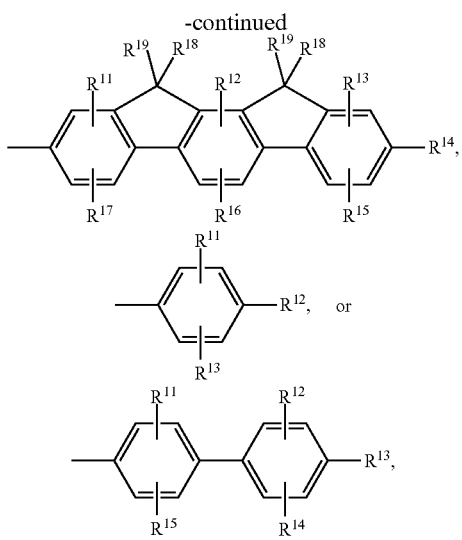

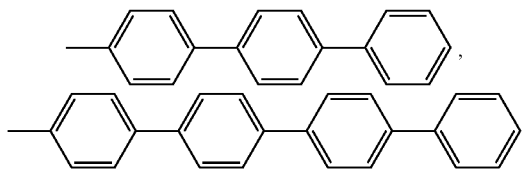

wherein
$R^{11}$, $R^{12}$, $R^{13}$, $R^{14}$, $R^{15}$, $R^{16}$ and $R^{17}$ are independently of each other H, $C_6$-$C_{18}$aryl; $C_6$-$C_{18}$aryl which is substituted by E; E, $C_1$-$C_{18}$alkyl; $C_1$-$C_{18}$alkyl which is substituted by E and/or interrupted by D; $C_6$-$C_{18}$aryl; $C_6$-$C_{18}$aryl which is substituted by E;

$R^{18}$ and $R^{19}$ are independently of each other H, $C_1$-$C_{18}$alkyl; $C_1$-$C_{18}$alkyl which is substituted by E and/or interrupted by D; $C_6$-$C_{18}$aryl; $C_6$-$C_{18}$aryl which is substituted by E;

D is —CO—; —COO—; —OCOO—; —S—; —SO—; —$SO_2$—; —O—; —$NR^5$—; —$SiR^5R^6$—; —$POR^5$—; —$CR^5$=$CR^6$—; or —C≡C—;

E is —$OR^5$; —$SR^5$; —$NR^5R^6$; —$COR^8$; —$COOR^7$; —$CONR^5R^6$; —CN; —$OCOOR^7$; or halogen; wherein $R^5$, $R^6$, $R^7$ and $R^8$ are as defined above, wherein pyrimidine compounds of formula I, wherein
V is hydrogen,
W and Y are a group of formula

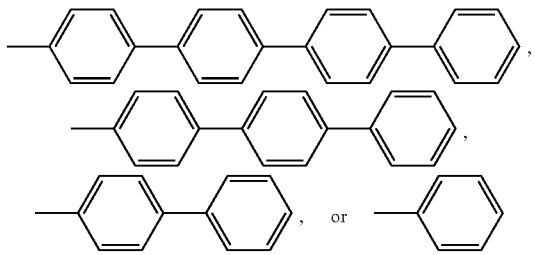

and
X is a group of formula or are most preferred.

The present pyrimidine compounds are known or can be prepared according to or analogous to known procedures. The present pyrimidine compounds are for instance derivatives of known hydroxyphenyl pyrimidine compounds: U.S. Pat. Nos. 3,442,898, 5,597,854 and 5,753,729, the relevant parts of which are hereby incorporated by reference. The present pyrimidine compounds can for instance be prepared according to or analogous to the following procedures (Suzuki aryl-aryl cross coupling reaction: Chem. Commun., 2002, 874-875; DE-A-3001188, J. Org. Chem. Vol. 36, 1971, 3382-3385):

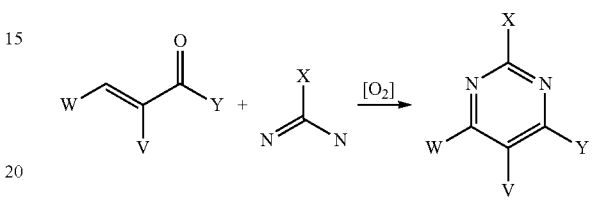

An amidine hydrochloride is added to a 2-propen-1-one derivative in a $C_1$-$C_4$-alcohol, like methanol, ethanol, propanol or butanol. A base, for example, an alkali metal hydroxide or alkoxide, such as sodium methoxide or potassium hydroxide is added and the solution is stirred in the presence of oxygen, for example dry air.

The pyrimidine compounds of the present invention, comprising the following units:

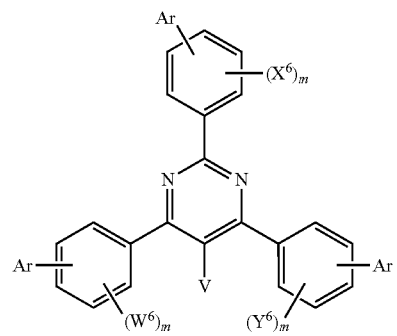

can be prepared according to a process, which comprises reacting a derivative of formula

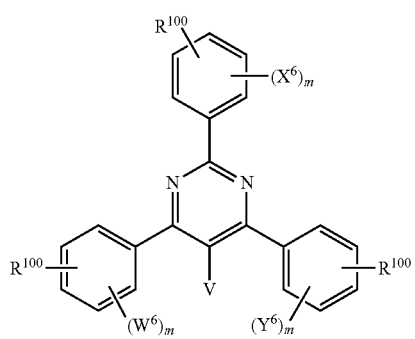

wherein $X^6$, V, $W^6$, $Y^6$ and m are as defined above,
$R^{100}$ stands for halogen such as chloro or bromo, preferably bromo, or E having the meaning of

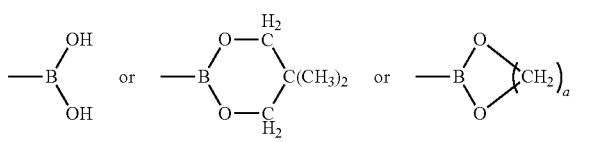

wherein a is 2 or 3,
with boronic acid derivative

E-Ar, or—in case R$^{100}$ is not halogen—

Hal-Ar, wherein Hal stands for halogen, preferably for bromo, wherein Ar is C$_6$-C$_{30}$-aryl or C$_2$-C$_{30}$-heteroaryl, which can be substituted, in the presence of an allylpalladium catalyst of the p-halo(triisopropylphosphine)(η$^3$-allyl)palladium(II) type (see for example WO99/47474).

Preferably, the reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, Na$_2$CO$_3$, K$_2$CO$_3$, Cs$_2$CO$_3$ and the like, preferably an aqueous K$_2$CO$_3$ solution is chosen. Usually, the molar ratio of the base to compound III is chosen in the range of from 0.5:1 to 50:1.

Generally, the reaction temperature is chosen in the range of from 40 to 180° C., preferably under reflux conditions.

Preferred, the reaction time is chosen in the range of from 1 to 80 hours, more preferably from 20 to 72 hours.

In a preferred embodiment a usual catalyst for coupling reactions or for polycondensation reactions is used, preferably Pd-based catalyst such as known tetrakis(triarylphosphonium)-palladium, preferably (Ph$_3$P)$_4$Pd and derivatives thereof. Usually, the catalyst is added in a molar ratio from inventive DPP polymer to the catalyst in the range of from 100:1 to 10:1, preferably from 50:1 to 30:1.

Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative.

The obtained inventive polymer can be isolated by well-known methods. Preferably, after cooling down the reaction mixture to room temperature, it is poured into acetone and the obtained precipitation is filtered off, washed and dried.

C$_1$-C$_{18}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, or octadecyl.

C$_1$-C$_{18}$Alkoxy radicals are straight-chain or branched alkoxy radicals, e.g. methoxy, ethoxy, n-propoxy, iso-propoxy, n-butoxy, sec-butoxy, tert-butoxy, amyloxy, iso-amyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

C$_2$-C$_{18}$Alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

C$_{2-24}$Alkynyl is straight-chain or branched and preferably C$_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl or 1-tetracosyn-24-yl, C$_4$-C$_{18}$cycloalkyl is preferably C$_5$-C$_{12}$cycloalkyl, such as, for example, cyclopentyl, cyclohexyl, cycloheptyl, cyclooctyl, cyclononyl, cyclodecyl, cyclododecyl. Cyclohexyl and cyclododecyl are most preferred.

The term "aryl group" is typically C$_6$-C$_{30}$aryl, such as phenyl, indenyl, azulenyl, naphthyl, biphenyl, terphenylyl or quadphenylyl, as-indacenyl, s-indacenyl, acenaphthylenyl, phenanthryl, fluoranthenyl, triphenlenyl, chrysenyl, naphthacen, picenyl, perylenyl, pentaphenyl, hexacenyl, pyrenyl, anthracenyl, terphenylyl or quadphenylyl, which can be substituted or unsubstituted, preferably phenyl, 1-naphthyl, 2-naphthyl, 9-phenanthryl, 2- or 9-fluorenyl, 3- or 4-biphenyl, which may be unsubstituted or substituted. Examples of C$_6$-C$_{18}$aryl are phenyl, 4-methylphenyl, 4-methoxyphenyl, 1-naphthyl, 2-naphthyl, 3- or 4-biphenyl, 9-phenanthryl, 2- or 9-fluorenyl, which may be unsubstituted or substituted.

C$_7$-C$_{24}$aralkyl radicals are preferably C$_7$-C$_{15}$aralkyl radicals, which may be substituted, such as, for example, benzyl, 2-benzyl-2-propyl, β-phenethyl, α,α-dimethylbenzyl, ω-phenyl-butyl, ω-phenyl-octyl, ω-phenyl-dodecyl or 3-methyl-5-(1',1',3',3'-tetramethyl-butyl)-benzyl, The term "heteroaryl group", especially C$_2$-C$_{30}$heteroaryl, is a ring, wherein nitrogen, oxygen or sulfur are the possible hetero atoms, and is typically an unsaturated heterocyclic radical with five to 18 atoms having at least six conjugated t-electrons such as thienyl, benzo[b]thienyl, dibenzo[b,d]thienyl, thianthrenyl, furyl, furfuryl, 2H-pyranyl, benzofuranyl, isobenzofuranyl, 2H-chromenyl, xanthenyl, dibenzofuranyl, phenoxythienyl, pyrrolyl, imidazolyl, pyrazolyl, pyridyl, bipyridyl, triazinyl, pyrimidinyl, pyrazinyl, 1H-pyrrolizinyl, isoindolyl, pyridazinyl, indolizinyl, isoindolyl, indolyl, 3H-indolyl, phthalazinyl, naphthyridinyl, quinoxalinyl, quinazolinyl, cinnolinyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, 4aH-carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the above-mentioned mono- or bicyclic heterocyclic radicals, which may be unsubstituted or substituted.

Examples of a five or six membered ring formed by R$^5$ and R$^6$ and R$^{103}$ and R$^{104}$, respectively are heterocycloalkanes or heterocycloalkenes having from 3 to 5 carbon atoms which can have one additional hetero atom selected from nitrogen, oxygen and sulfur, for example

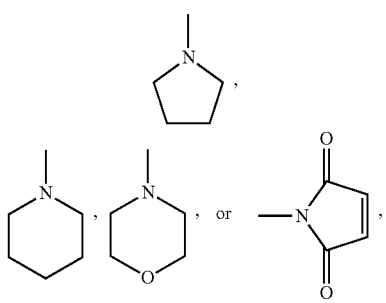

which can be part of a bicyclic system, for example

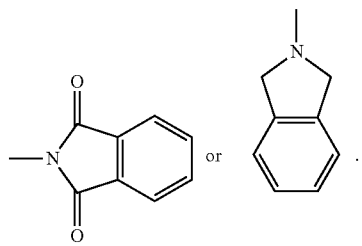

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

As described above, the aforementioned radicals may be substituted by E and/or, if desired, interrupted by D. Interruptions are of course possible only in the case of radicals containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_n$—$R^x$, where n is a number from the range 1-9 and $R^x$ is H or $C_1$-$C_{10}$alkyl or $C_2$-$C_{10}$alkanoyl (e.g. CO—CH($C_2H_5$)$C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR_z$, $CH(CH_3)$COOR$^z$, $C(CH_3)_2COOR^z$, where $R^z$ is H, $C_1$-$C_{18}$alkyl, $(CH_2CH_2O)_{1-9}$—$R^x$, and $R^x$embraces the definitions indicated above;

$CH_2CH_2$—O—CO—CH=$CH_2$; $CH_2CH(OH)CH_2$—O—CO—C($CH_3$)=$CH_2$.

To obtain organic layers of this invention with the proper $T_g$, or glass transition temperature, it is advantageous that the present organic compounds have a melting point greater than about 150° C., for example greater than about 200° C., for example greater than about 250° C., for instance greater than about 300° C.

The electroluminescent devices of the present invention are otherwise designed as is known in the art, for example as described in U.S. Pat. Nos. 5,518,824, 6,225,467, 6,280,859, 5,629,389, 5,486,406, 5,104,740, 5,116,708 and 6,057,048, the relevant disclosures of which are hereby incorporated by reference.

For example, organic EL devices contain one or more layers such as:

substrate; base electrode; hole-injecting layer; hole transporting layer; emitter layer; electron-transporting layer; electron-injecting layer; top electrode; contacts and encapsulation.

This structure is a general case and may have additional layers or may be simplified by omitting layers so that one layer performs a plurality of tasks. For instance, the simplest organic EL device consists of two electrodes which sandwich an organic layer that performs all functions, including the function of light emission.

A preferred EL device comprises in this order:
(a) an anode,
(b) a hole injecting layer and/or a hole transporting layer,
(c) a light-emitting layer,
(d) optionally an electron transporting layer and
(e) a cathode.

In particular, the present organic compounds function as light emitters and are contained in the light emission layer or form the light-emitting layer.

The light emitting compounds of this invention exhibit intense fluorescence in the solid state and have excellent electric-field-applied light emission characteristics. Further, the light emitting compounds of this invention are excellent in the injection of holes from a metal electrode and the transportation of holes; as well as being excellent in the injection of electrons from a metal electrode and the transportation of electrons. They are effectively used as light emitting materials and may be used in combination with other hole transporting materials, other electron transporting materials or other dopants.

The organic compounds of the present invention form uniform thin films. The light emitting layers may therefore be formed of the present organic compounds alone.

Alternatively, the light-emitting layer may contain a known light-emitting material, a known dopant, a known hole transporting material or a known electron transporting material as required. In the organic EL device, a decrease in the brightness and life caused by quenching can be prevented by forming it as a multi-layered structure. The light-emitting material, a dopant, a hole-injecting material and an electron-injecting material may be used in combination as required. Further, a dopant can improve the light emission brightness and the light emission efficiency, and can attain the red or blue light emission. Further, each of the hole transporting zone, the light-emitting layer and the electron transporting zone may have the layer structure of at least two layers. In the hole transporting zone in this case, a layer to which holes are injected from an electrode is called "hole-injecting layer", and a layer which receives holes from the hole-injecting layer and transport the holes to a light-emitting layer is called "hole transporting layer". In the electron transporting zone, a layer to which electrons are injected from an electrode is called "electron-injecting layer", and a layer which receives electrons from the electron-injecting layer and transports the electrons to a light-emitting layer is called "electron transporting layer". These layers are selected and used depending upon factors such as the energy level and heat resistance of materials and adhesion to an organic layer or metal electrode.

The light-emitting material or the dopant which may be used in the light-emitting layer together with the organic compounds of the present invention includes for example anthracene, naphthalene, phenanthrene, pyrene, tetracene, coronene, chrysene, fluorescein, perylene, phthaloperylene, naphthaloperylene, perinone, phthaoperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, and fluorescent dyestuffs for a dyestuff laser or for brightening.

If the pyrimidine compounds of the formula I are used as host, the weight ratio of the pyrimidine compound (host) to the guest compound is in general 50:50 to 99.99:0.01, preferably 90:10 to 99.99:0.01, more preferably 95:5 to 99.9:0.1 most preferably 98:2 to 99.9:0.1.

The pyrimidine compounds of the present invention and the above compound or compounds that can be used in a light-emitting layer may be used in any mixing ratio for forming a light-emitting layer. That is, the organic compounds of the present invention may provide a main component for forming a light-emitting layer, or they may be a doping material in another main material, depending upon a combination of the above compounds with the organic compounds of the present invention.

The hole-injecting material is selected from compounds which are capable of transporting holes, are capable of receiving holes from the anode, have an excellent effect of injecting holes to a light-emitting layer or a light-emitting material, prevent the movement of excitons generated in a light-emitting layer to an electron-injecting zone or an electron-injecting material and have the excellent capability of forming a thin film. Suitable hole-injecting materials include for example a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electroconducting polymer.

In the organic EL device of the present invention, the hole-injecting material which is more effective is an aromatic tertiary amine derivative or a phthalocyanine derivative. Although not specially limited, specific examples of the tertiary amine derivative include triphenylamine, tritolylamine, tolyldiphenylamine, N,N'-diphenyl-N,N'-(3-methylphenyl)-1,1-biphenyl-4,4'-diamine, N,N,N',N'-tetra(4-methylphenyl)-1,1'-phenyl-4,4'-diamine, N,N,N',N'-tetra(4-methylphenyl)-1,1'-biphenyl-4,4'-diamine, N,N'-diphenyl-N,N'-di(1-naphthyl)-1,1'-biphenyl-4,4'-diamine, N,N'-di(methylphenyl)-N,N'-di(4-n-butylphenyl)-phenanthrene-9,10-diamine, 4,4', 4"-tris(3-methylphenyl)-N-phenylamino)triphenylamine, 1,1-bis(4-di-p-tolylaminophenyl)cyclohexane, and oligomers or polymers having aromatic tertiary amine structures of these.

Although not specially limited, specific examples of the phthalocyanine (Pc) derivative include phthalocyanine derivatives or naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc.

The hole transporting layer can reduce the driving voltage of the device and improve the confinement of the injected charge recombination within the pyrimidin light emitting layer. Any conventional suitable aromatic amine hole transporting materials described for the hole-injecting layer may be selected for forming this layer.

A preferred class of hole transporting materials is comprised of 4,4'-bis(9-carbazolyl)-1,1'-biphenyl compounds of the formula

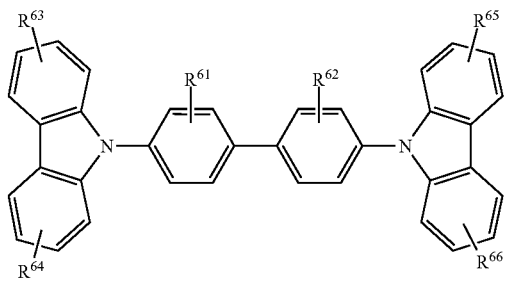

wherein $R^{61}$ and $R^{62}$ is a hydrogen atom or an $C_1$-$C_3$alkyl group; $R^{63}$ through $R^{66}$ are substituents independently selected from the group consisting of hydrogen, a $C_1$-$C_6$alkyl group, a $C_1$-$C_6$alkoxy group, a halogen atom, a dialkylamino group, a $C_6$-$C_{30}$aryl group, and the like. Illustrative examples of 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like.

The electron transporting layer is not necessarily required for the present device, but is optionally and preferably used for the primary purpose of improving the electron injection characteristics of the EL devices and the emission uniformity. Illustrative examples of electron transporting compounds, which can be utilized in this layer, include the metal chelates of 8-hydroxyquinoline as disclosed in U.S. Pat. Nos. 4,539,507, 5,151,629, and 5,150,006, the disclosures of which are totally incorporated herein by reference.

Although not specially limited, specific examples of the metal complex compound include lithium 8-hydroxyquinolinate, zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), gallium bis(2-methyl-8-quinolinate)(2-naphtholate), gallium bis(2-methyl-8-quinolinate)phenolate, zinc bis(o-(2-benzooxazolyl)phenolate), zinc bis(o-(2-benzothiazolyl)phenolate) and zinc bis(o-(2-benzotrizolyl)phenolate). The nitrogen-containing five-membered derivative is preferably an oxazole, thiazole, thiadiazole, or triazole derivative.

Although not specially limited, specific examples of the above nitrogen-containing five-membered derivative include 2,5-bis(1-phenyl)-1,3,4-oxazole, 1,4-bis(2-(4-methyl-5-phenyloxazolyl)benzene, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene. Another class of electron transport materials are oxadiazole metal chelates, such as bis[2-(2-hydroxyphenyl)-5-phenyl-1,3,4-oxadiazolato]zinc;

bis[2-(2-hydroxyphenyl)-5-phenyl-1,3,4-oxadiazolato]beryllium; bis[2-(2-hydroxyphenyl)-5-(1-naphthyl)-1,3,4-oxadiazolato]zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis(2-hydroxyphenyl)-5-phenyl-1,3,4-oxadiazolato]lithium; bis[2-(2-hydroxyphenyl)-5-p-tolyl-1,3,4-oxadiazolato]zinc; bis 2-(2-hydroxyphenyl)-5-p-tolyl-1,3,4-oxadiazolato]beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato]zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato]zinc; bis[2-(2-hydroxy phenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-.alpha.-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis[2-(2-hydroxyphenyl)-5-p-pyridyl-1,3,4-oxadiazolato]beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato]beryllium, and the like.

In the organic EL device of the present invention, the light-emitting layer may contain, in addition to the light-emitting organic material of the present invention, at least one of other light-emitting material, other dopant, other hole-injecting material and other electron-injecting material. For improving the organic EL device of the present invention in the stability against temperature, humidity and ambient atmosphere, a protective layer may be formed on the surface of the device, or the device as a whole may be sealed with a silicone oil, or the like.

The electrically conductive material used for the anode of the organic EL device is suitably selected from those materials having a work function of greater than 4 eV. The electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electroconducting polymers such as polythiophene and polypyrrole.

The electrically conductive material used for the cathode is suitably selected from those having a work function of smaller than 4 eV. The electrically conductive material includes magnesium, calcium, tin, lead, titanium, yttrium, lithium, ruthenium, manganese, aluminum and alloys of these, while the electrically conductive material shall not be limited to these. Examples of the alloys include magnesium/silver, magnesium/indium and lithium/aluminum, while the alloys shall not be limited to these. Each of the anode and the cathode may have a layer structure formed of two layers or more as required.

For the effective light emission of the organic EL device, at least one of the electrodes is desirably sufficiently transparent in the light emission wavelength region of the device. Further, the substrate is desirably transparent as well. The transparent electrode is produced from the above electrically conductive material by a deposition method or a sputtering method such that a predetermined light transmittance is secured. The electrode on the light emission surface side has for instance a light transmittance of at least 10%. The substrate is not specially limited so long as it has adequate mechanical and thermal strength and has transparency. For example, it is selected from glass substrates and substrates of transparent resins such as a polyethylene substrate, a polyethylene terephthalate substrate, a polyether sulfone substrate and a polypropylene substrate.

In the organic EL device of the present invention, each layer can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. The thickness of each layer is for example in the range of from about 5 nm to about 10 μm, for instance about 10 nm to about 0.2 μm.

In the wet film forming method, a material for forming an intended layer is dissolved or dispersed in a proper solvent such as ethanol, chloroform, tetrahydrofuran and dioxane, and a thin film is formed from the solution or dispersion. The solvent shall not be limited to the above solvents. For improving the film formability and preventing the occurrence of pinholes in any layer, the above solution or dispersion for forming the layer may contain a proper resin and a proper additive. The resin that can be used includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electroconducting polymers such as polythiophene and polypyrrole. The above additive includes an antioxidant, an ultraviolet absorbent and a plasticizer.

When the light-emitting organic material of the present invention is used in a light-emitting layer of an organic EL device, an organic EL device can be improved in organic EL device characteristics such as light emission efficiency and maximum light emission brightness. Further, the organic EL device of the present invention is remarkably stable against heat and electric current and gives a usable light emission brightness at a low actuation voltage. The problematic deterioration of conventional devices can be remarkably decreased.

The organic EL device of the present invention has significant industrial values since it can be adapted for a flat panel display of an on-wall television set, a flat light-emitting device, a light source for a copying machine or a printer, a light source for a liquid crystal display or counter, a display signboard and a signal light.

The material of the present invention can be used in the fields of an organic EL device, an electrophotographic photoreceptor, a photoelectric converter, a solar cell, an image sensor, dye lasers and the like.

The following Examples illustrate the invention. In the Examples and throughout this application, the term light emitting material means the present pyrimidine compounds.

EXAMPLES

Example 1 (A-1)

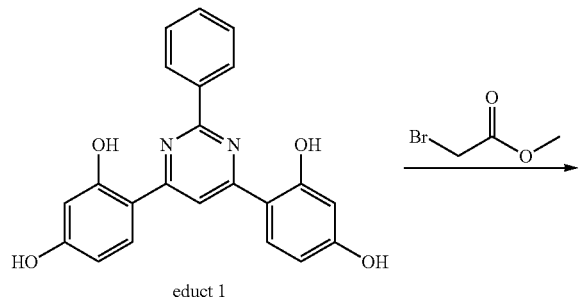

To 1.00 g (2.69 mmol) of educt 1 (prepared according to U.S. Pat. No. 3,442,898 from resorcinol and 4,6-dichloro-2-phenyl-pyrimidine; J. Org. Chem. 1988, 53, 4137) in 20 ml water free DMF 3.29 g (21.5 mmol) methyl-bromoacetate and 2.97 g (21.5 mmol) potassium carbonate are added. The reaction mixture is stirred at 100° C. under nitrogen for 2 h. The reaction mixture is diluted with water. The organic phase is extracted with dichloromethane und dried with magnesium sulfate. The solvent is removed. After chromatography of the crude product on silica gel with toluene/ethyl acetate 8/2 the desired product is obtained. Melting point: 178.0-179.0° C.

Example 2 (A-2)

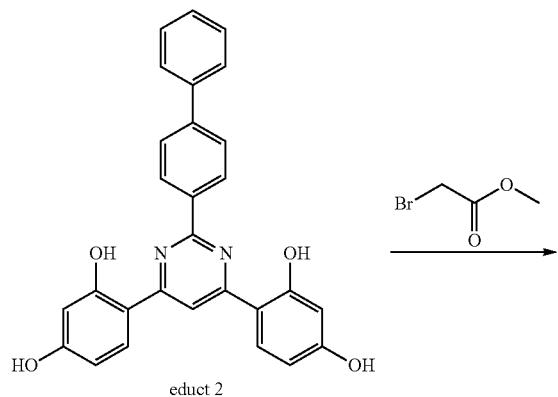

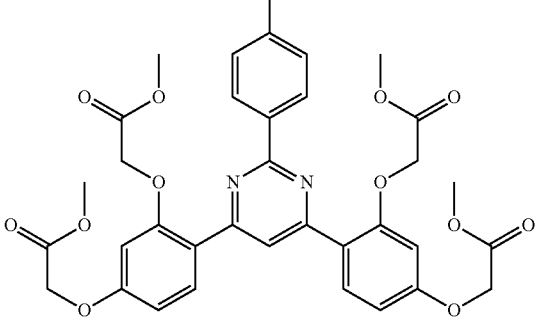

To 520 mg (1.16 mmol) of educt 2 (prepared according to U.S. Pat. No. 3,442,898 from resorcinol and 4,6-dichloro-2-biphenyl-pyrimidine; EP-A-96657) in 20 ml water free DMF 1.42 g (9.28 mmol) methyl-bromoacetate and 1.28 g (9.28 mmol) potassium carbonate are added. The reaction mixture is stirred at 100° C. under nitrogen for 2 h. The reaction mixture is diluted with water. The organic phase is extracted with dichloromethane und dried with magnesium sulfate. The solvent is removed. After chromatography of the crude product on silica gel with toluene/ethyl acetate 9/1 and later 7/3 the desired product is obtained. Melting point: 119.5-121.5° C.

Example 3 (A-3)

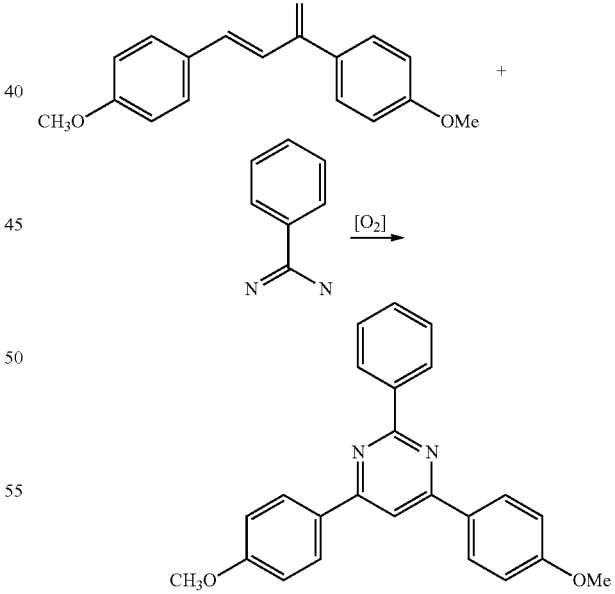

To 4.31 g (16.1 mmol) of 1,3-bis(4-methoxyphenyl)-2-propen-1-one in 25 ml water free ethanol 1.89 g (8.11 mmol) biphenylbenzamidine hydrochlorid are added. A solution of 1.07 g (19.08 mmol) potassium hydroxide is added during 15 min. Dry air is bubbled through the reaction mixture. The reaction mixture is refluxed for 24 h. The reaction mixture is poured into water. The solid is filtered off and washed with water. The product is crystallized 2 times from acetic acid (96-98%). Melting point: 168-169° C.

Compounds A-4 to A-54 can be obtained in a manner analogous to Examples 1 to 5.

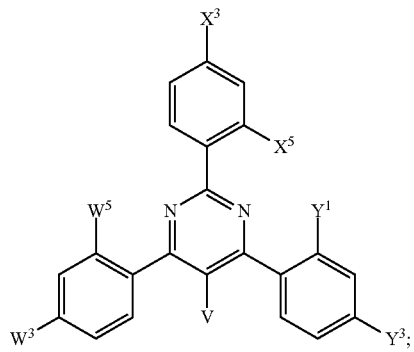

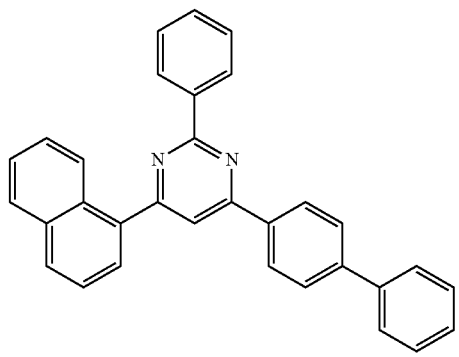

(A-54; melting point: 162-164° C.)

| Cpd. | X³ | Y³ | W³ | X⁵ | Y¹ | W⁵ | V |
|---|---|---|---|---|---|---|---|
| A-1 | H | OCH₂COOMe | OCH₂COOMe | H | OCH₂COOMe | OCH₂COOMe | H |
| A-2 | Ph | OCH₂COOMe | OCH₂COOMe | H | OCH₂COOMe | OCH₂COOMe | H |
| A-3 | H | OMe | OMe | H | H | H | H |
| A-4[1) | H | Ph | Ph | H | H | H | H |
| A-5 | H | OMe | OMe | H | OMe | OMe | H |
| A-6 | H | OBu | OBu | H | H | H | H |
| A-7 | H | OBu | OBu | H | OBu | OBu | H |
| A-8 | OMe | OMe | OMe | OMe | OMe | OMe | H |
| A-9 | OMe | Br | Br | OMe | H | H | H |
| A-10 | Ph | Br | Br | H | H | H | H |
| A-11 | OMe | Ph | Ph | OMe | H | H | H |
| A-12 | Ph | Ph | Ph | H | H | H | H |
| A-13 | SMe | SMe | SMe | H | H | H | H |
| A-14 | H | SMe | SMe | H | H | H | H |
| A-15 | H | OCH₂CH₂OAc | OCH₂CH₂OAc | H | H | H | H |
| A-16 | H | OCH₂CH₂OAc | OCH₂CH₂OAc | H | OCH₂CH₂OAc | OCH₂CH₂OAc | H |
| A-17 | H | OCH₂CH₂OCH₂Et | OCH₂CH₂OCH₂Et | H | H | H | H |
| A-18 | H | OCH₂CH₂OCH₂Et | OCH₂CH₂OCH₂Et | H | OCH₂CH₂OCH₂Et | OCH₂CH₂OCH₂Et | H |
| A-19 | H | N(CH₃)₂ | N(CH₃)₂ | H | H | H | H |
| A-20 | H | —N(pyrrolidine) | —N(pyrrolidine) | H | H | H | H |
| A-21 | Ph | N(CH₃)₂ | N(CH₃)₂ | H | H | H | H |
| A-22 | Ph | —N(pyrrolidine) | —N(pyrrolidine) | H | H | H | H |
| A-23 | H | CH₃ | CH₃ | H | H | H | H |
| A-24 | Ph | CH₃ | CH₃ | H | H | H | H |
| A-25 | Ph | Ph | Ph | H | H | H | CH₃ |
| A-26 | OMe | OMe | OMe | H | H | H | CH₃ |
| A-27 | H | Ph | Ph | H | H | H | CH₃ |

[1)]melting point: 244-245° C.

| Cpd. | X³ | Y³ | W³ | X⁵ | Y¹ | W⁵ | V |
|---|---|---|---|---|---|---|---|
| A-28 | H | OMe | OMe | H | H | H | $CH_3$ |
| A-29 | H | OMe | OMe | H | OMe | OMe | $CH_3$ |
| A-30 | H | OBu | OBu | H | H | H | $CH_3$ |
| A-31 | H | OBu | OBu | H | OBu | OBu | $CH_3$ |
| A-32 | OMe | OMe | OMe | OMe | OMe | OMe | $CH_3$ |
| A-33 | OMe | Br | Br | OMe | H | H | $CH_3$ |
| A-34 | Ph | Br | Br | H | H | H | $CH_3$ |
| A-35 | OMe | Ph | Ph | OMe | H | H | $CH_3$ |
| A-36 | H | $OCH_2COOMe$ | $OCH_2COOMe$ | H | $OCH_2COOMe$ | $OCH_2COOMe$ | $CH_3$ |
| A-37 | SMe | SMe | SMe | H | H | H | $CH_3$ |
| A-38 | H | SMe | SMe | H | H | H | $CH_3$ |
| A-39 | H | $OCH_2CH_2Oac$ | $OCH_2CH_2Oac$ | H | H | H | $CH_3$ |
| A-40 | H | $OCH_2CH_2Oac$ | $OCH_2CH_2Oac$ | H | $OCH_2CH_2Oac$ | $OCH_2CH_2Oac$ | $CH_3$ |
| A-41 | H | $OCH_2CH_2OCH_2Et$ | $OCH_2CH_2OCH_2Et$ | H | H | H | $CH_3$ |
| A-42 | H | $OCH_2CH_2OCH_2Et$ | $OCH_2CH_2OCH_2Et$ | H | $OCH_2CH_2OCH_2Et$ | $OCH_2CH_2OCH_2Et$ | $CH_3$ |
| A-43 | OBu | Ph | Ph | OBu | H | H | $CH_3$ |
| A-44 | H | $N(CH_3)_2$ | $N(CH_3)_2$ | H | H | H | $CH_3$ |
| A-45 | H | —N(pyrrolidine) | —N(pyrrolidine) | H | H | H | $CH_3$ |
| A-46 | Ph | $N(CH_3)_2$ | $N(CH_3)_2$ | H | H | H | $CH_3$ |
| A-47 | Ph | —N(pyrrolidine) | —N(pyrrolidine) | H | H | H | $CH_3$ |
| A-48 | Ph | $CH_3$ | $CH_3$ | H | H | H | $CH_3$ |
| A-49 | Ph | $CH_3$ | $CH_3$ | H | H | H | $CH_3$ |
| A-50 | OMe | OMe | OMe | H | H | H | H |
| A-51[1] | H | H | H | H | H | H | H |
| A-52[2] | Ph | H | H | H | H | H | H |

[1] melting point: 188-189° C.
[2] melting point: 196-198° C.

Example 4 (B-1)

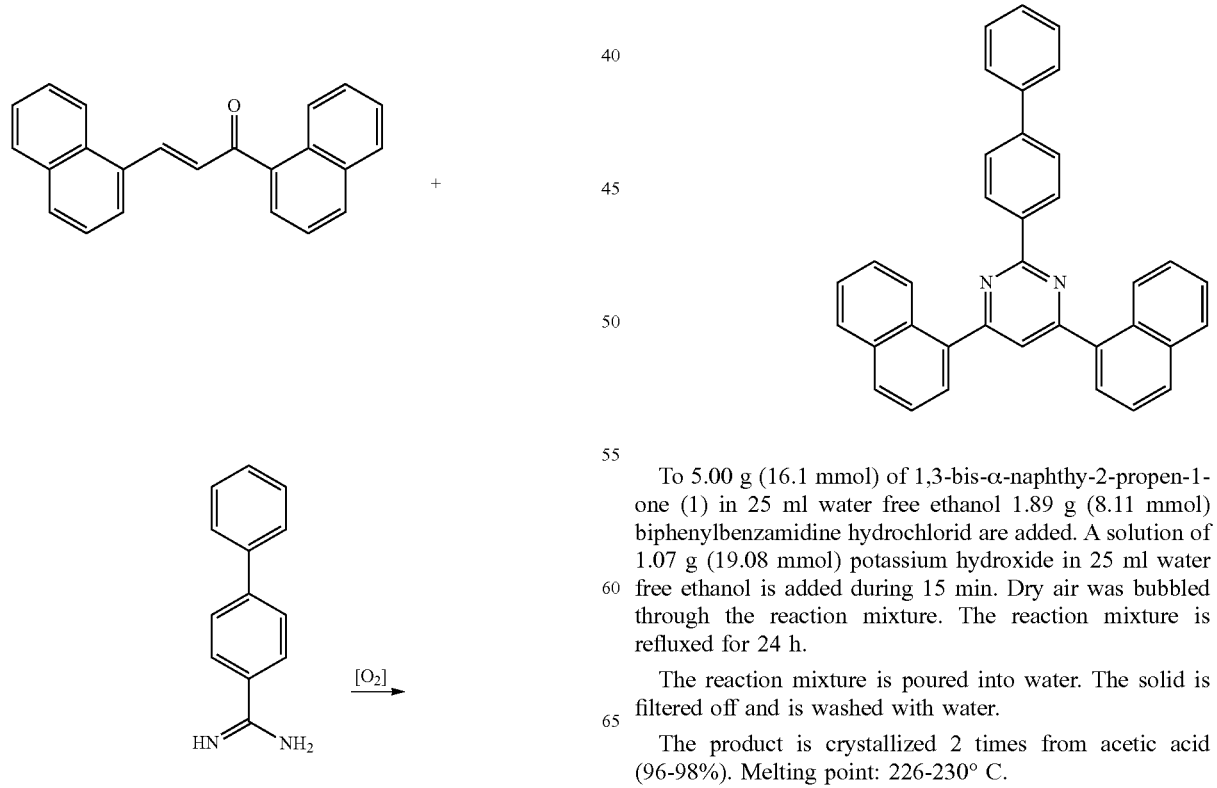

To 5.00 g (16.1 mmol) of 1,3-bis-α-naphthy-2-propen-1-one (1) in 25 ml water free ethanol 1.89 g (8.11 mmol) biphenylbenzamidine hydrochlorid are added. A solution of 1.07 g (19.08 mmol) potassium hydroxide in 25 ml water free ethanol is added during 15 min. Dry air was bubbled through the reaction mixture. The reaction mixture is refluxed for 24 h.

The reaction mixture is poured into water. The solid is filtered off and is washed with water.

The product is crystallized 2 times from acetic acid (96-98%). Melting point: 226-230° C.

Example 5 (B-2)

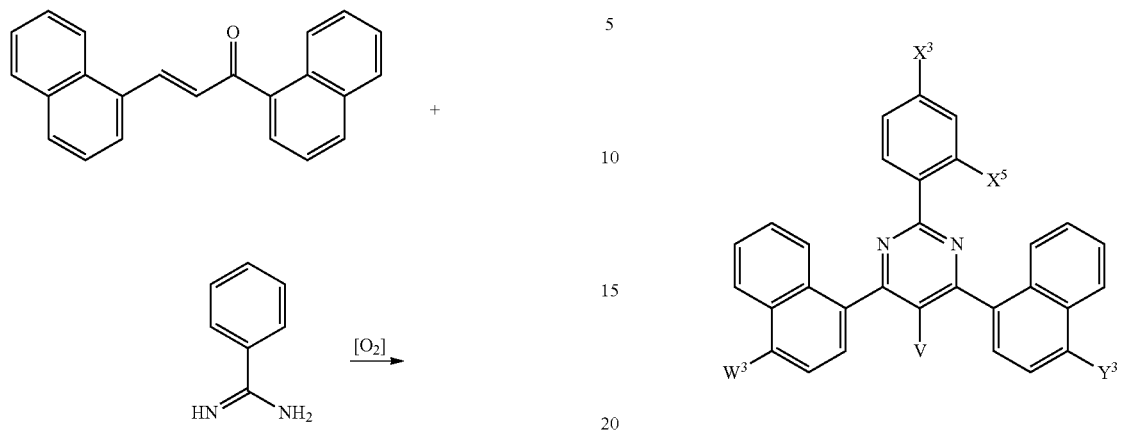

To 5.00 g (16.1 mmol) of 1,3-bis-α-naphthy-2-propen-1-one (1) in 25 ml water free ethanol 1.27 g (8.11 mmol) benzamidine hydrochlorid are added. A solution of 1.07 g (19.08 mmol) potassium hydroxide in 25 ml water free ethanol is added during 15 min. Dry air is bubbled through the reaction mixture. The reaction mixture is refluxed for 24 h. The reaction mixture is poured into water. The solid is filtered off and is washed with water. The product is crystallized from acetic acid (96-98%). Melting point: 179-180° C.

Compounds B-3 to B-23 can be obtained in a manner analogous to Examples 4 and 5.

| Cpd. | $X^3$ | $Y^3$ | $W^3$ | $X^5$ | V |
|---|---|---|---|---|---|
| B-1 | Ph | H | H | H | H |
| B-2 | H | H | H | H | H |
| B-3 | OBu | H | H | OBu | H |
| B-4 | OMe | H | H | OMe | H |
| B-5 | $OCH_2COOMe$ | H | H | $OCH_2COOMe$ | H |
| B-6 | H | OMe | OMe | H | H |
| B-7 | $OCH_2CH_2OCH_2Et$ | H | H | $OCH_2CH_2OCH_2Et$ | H |
| B-8 | $OCH_2CH_2OAc$ | H | H | $OCH_2CH_2OAc$ | H |
| B-9 | OMe | OMe | OMe | OMe | H |
| B-10 | OMe | OMe | OMe | OMe | H |
| B-11 | H | $CH_3$ | $CH_3$ | H | H |
| B-12 | Ph | $CH_3$ | $CH_3$ | H | H |
| B-13 | Ph | H | H | H | $CH_3$ |
| B-14 | OMe | H | H | OMe | $CH_3$ |
| B-15 | OBu | H | H | OBu | $CH_3$ |
| B-16 | H | H | H | H | $CH_3$ |
| B-17 | $OCH_2COOMe$ | H | H | $OCH_2COOMe$ | $CH_3$ |
| B-18 | H | OMe | OMe | H | $CH_3$ |
| B-19 | $OCH_2CH_2OCH_2Et$ | H | H | $OCH_2CH_2OCH_2Et$ | $CH_3$ |
| B-20 | $OCH_2CH_2OAc$ | H | H | $OCH_2CH_2OAc$ | $CH_3$ |
| B-21 | H | $CH_3$ | $CH_3$ | H | $CH_3$ |
| B-22 | Ph | $CH_3$ | $CH_3$ | H | $CH_3$ |

Example 6 (C-1)

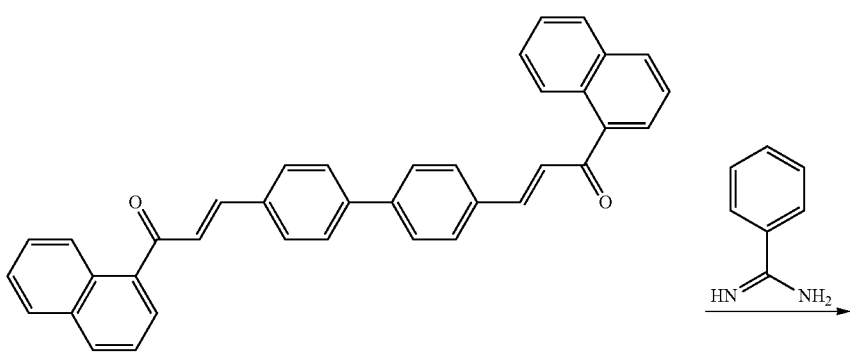

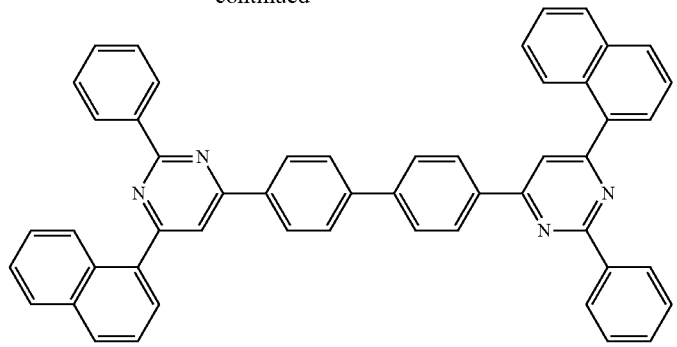

To 4.50 g (8.74 mmol) of the 2-propen-1-one derivative shown above in 50 ml water free ethanol 1.37 g (8.74 mmol) benzamidine hydrochloride are added. A solution of 1.15 g (20.6 mmol) potassium hydroxide in 50 ml water free ethanol is added during 15 min. Dry air is bubbled through the reaction mixture. The reaction mixture is refluxed for 24 h, poured into water and the water phase is extracted with dichloromethane. The organic phase is dried with magnesium sulfate, the solvent is removed by distillation and the remaining residue is purified by column chromatography (toluene/hexane 2/1).

$^1$H-NMR (300 MHz, CDCl$_3$): δ=8.75-8.72 (m, 4H); 8.45-8.37 (m, 12H); 8.04-7.82 (m, 6H); 7.67-7.50 (m, 12h).

Compounds C-2 to C-24 can be obtained in a manner analogous to Example 6.

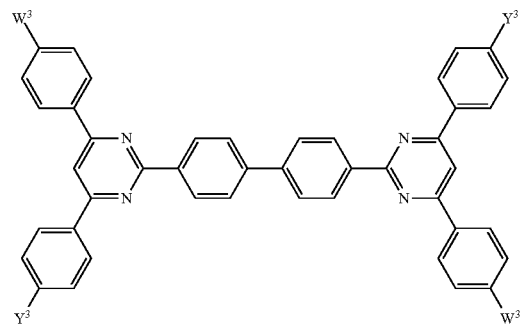

| Cpd. | W$^3$ | Y$^3$ |
|---|---|---|
| C-2 | H | H |
| C-3 | H | H |
| C-4 | H | H |
| C-5 | H | H |
| C-6 | H | H |
| C-7 | OCH$_3$ | OCH$_3$ |
| C-8 | OCH$_3$ | OCH$_3$ |
| C-9 | OCH$_3$ | OCH$_3$ |
| C-10 | OCH$_3$ | OCH$_3$ |
| C-11 | OCH$_3$ | OCH$_3$ |
| C-12 | SCH$_3$ | SCH$_3$ |
| C-13 | SCH$_3$ | SCH$_3$ |
| C-14 | SCH$_3$ | SCH$_3$ |
| C-15 | SCH$_3$ | SCH$_3$ |
| C-16 | SCH$_3$ | SCH$_3$ |
| C-17 | SCH$_3$ | SCH$_3$ |
| C-18 | N(CH$_3$)$_2$ | N(CH$_3$)$_2$ |
| C-19 | N(CH$_3$)$_2$ | N(CH$_3$)$_2$ |
| C-20 | N(CH$_3$)$_2$ | N(CH$_3$)$_2$ |
| C-21 | N(CH$_3$)$_2$ | N(CH$_3$)$_2$ |
| C-22 | N(CH$_3$)$_2$ | N(CH$_3$)$_2$ |
| C-23 | N(CH$_3$)$_2$ | N(CH$_3$)$_2$ |
| C-24 | N(CH$_3$)$_2$ | N(CH$_3$)$_2$ |

Compounds D-1 to D-23 can be obtained in a manner analogous to Example 6.

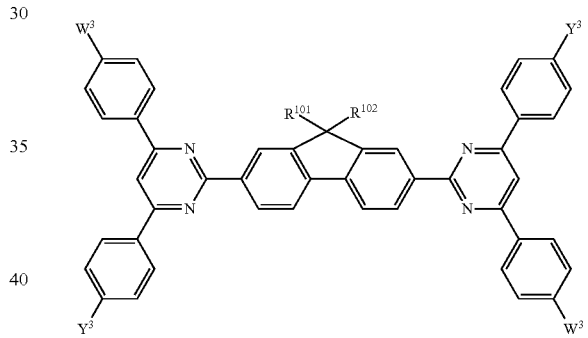

| Cpd. | R$^{101}$ | R$^{102}$ | W$^3$ | Y$^3$ |
|---|---|---|---|---|
| D-1 | C$_6$H$_{13}$ | C$_6$H$_{13}$ | H | H |
| D-2 | Bu | Bu | H | H |
| D-3 | Et | Et | H | H |
| D-4 | H | H | H | H |
| D-5 | Ph | Ph | H | H |
| D-6 | C$_6$H$_{13}$ | C$_6$H$_{13}$ | OCH$_3$ | OCH$_3$ |
| D-7 | Bu | Bu | OCH$_3$ | OCH$_3$ |
| D-8 | Et | Et | OCH$_3$ | OCH$_3$ |
| D-9 | H | H | OCH$_3$ | OCH$_3$ |
| D-10 | Ph | Ph | OCH$_3$ | OCH$_3$ |
| D-11 | C$_6$H$_{13}$ | C$_6$H$_{13}$ | SCH$_3$ | SCH$_3$ |
| D-12 | Bu | Bu | SCH$_3$ | SCH$_3$ |
| D-13 | Et | Et | SCH$_3$ | SCH$_3$ |
| D-14 | H | H | SCH$_3$ | SCH$_3$ |
| D-15 | Ph | Ph | SCH$_3$ | SCH$_3$ |
| D-16 | C$_6$H$_{13}$ | C$_6$H$_{13}$ | SCH$_3$ | SCH$_3$ |
| D-17 | C$_6$H$_{13}$ | C$_6$H$_{13}$ | N(CH$_3$)$_2$ | N(CH$_3$)$_2$ |
| D-18 | Bu | Bu | N(CH$_3$)$_2$ | N(CH$_3$)$_2$ |
| D-19 | Et | Et | N(CH$_3$)$_2$ | N(CH$_3$)$_2$ |
| D-20 | H | H | N(CH$_3$)$_2$ | N(CH$_3$)$_2$ |
| D-21 | Ph | Ph | N(CH$_3$)$_2$ | N(CH$_3$)$_2$ |
| D-22 | C$_6$H$_{13}$ | C$_6$H$_{13}$ | N(CH$_3$)$_2$ | N(CH$_3$)$_2$ |
| D-23 | Bu | Bu | N(CH$_3$)$_2$ | N(CH$_3$)$_2$ |

Compounds E-1 to E-35 can be obtained in a manner analogous to Example 6.

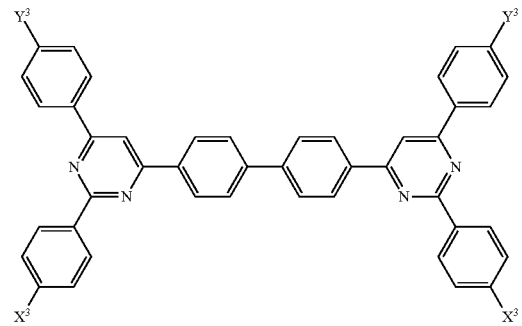

| Cpd. | Y³ | X³ |
| --- | --- | --- |
| E-1 | H | H |
| E-2 | H | H |
| E-3 | H | H |
| E-4 | H | H |
| E-5 | H | H |
| E-6 | OCH₃ | OCH₃ |
| E-7 | OCH₃ | OCH₃ |
| E-8 | OCH₃ | OCH₃ |
| E-9 | OCH₃ | OCH₃ |
| E-10 | OCH₃ | OCH₃ |
| E-11 | OCH₃ | H |
| E-12 | OCH₃ | H |
| E-13 | OCH₃ | H |
| E-14 | OCH₃ | H |
| E-15 | OCH₃ | H |
| E-16 | SCH₃ | SCH₃ |
| E-17 | SCH₃ | SCH₃ |
| E-18 | SCH₃ | SCH₃ |
| E-19 | SCH₃ | SCH₃ |
| E-20 | SCH₃ | SCH₃ |
| E-21 | SCH₃ | H |
| E-22 | SCH₃ | H |
| E-23 | SCH₃ | H |
| E-24 | SCH₃ | H |
| E-25 | SCH₃ | H |
| E-26 | N(CH₃)₂ | N(CH₃)₂ |
| E-27 | N(CH₃)₂ | N(CH₃)₂ |
| E-28 | N(CH₃)₂ | N(CH₃)₂ |
| E-29 | N(CH₃)₂ | N(CH₃)₂ |
| E-30 | N(CH₃)₂ | N(CH₃)₂ |
| E-31 | N(CH₃)₂ | H |
| E-32 | N(CH₃)₂ | H |
| E-33 | N(CH₃)₂ | H |
| E-34 | N(CH₃)₂ | H |
| E-35 | N(CH₃)₂ | H |

Compounds F-1 to F-35 can be obtained in a manner analogous to Example 6.

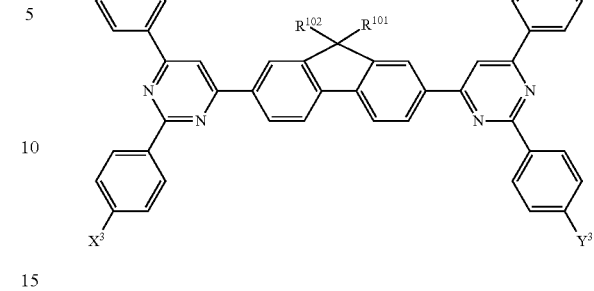

| Cpd. | R¹⁰¹ | R¹⁰² | Y³ | X³ |
| --- | --- | --- | --- | --- |
| F-1 | C₆H₁₃ | C₆H₁₃ | H | H |
| F-2 | Bu | Bu | H | H |
| F-3 | Et | Et | H | H |
| F-4 | H | H | H | H |
| F-5 | Ph | Ph | H | H |
| F-6 | C₆H₁₃ | C₆H₁₃ | OCH₃ | OCH₃ |
| F-7 | Bu | Bu | OCH₃ | OCH₃ |
| F-8 | Et | Et | OCH₃ | OCH₃ |
| F-9 | H | H | OCH₃ | OCH₃ |
| F-10 | Ph | Ph | OCH₃ | OCH₃ |
| F-11 | C₆H₁₃ | C₆H₁₃ | OCH₃ | H |
| F-12 | Bu | Bu | OCH₃ | H |
| F-13 | Et | Et | OCH₃ | H |
| F-14 | H | H | OCH₃ | H |
| F-15 | Ph | Ph | OCH₃ | H |
| F-16 | C₆H₁₃ | C₆H₁₃ | SCH₃ | SCH₃ |
| F-17 | Bu | Bu | SCH₃ | SCH₃ |
| F-18 | Et | Et | SCH₃ | SCH₃ |
| F-19 | H | H | SCH₃ | SCH₃ |
| F-20 | Ph | Ph | SCH₃ | SCH₃ |
| F-21 | C₆H₁₃ | C₆H₁₃ | SCH₃ | H |
| F-22 | Bu | Bu | SCH₃ | H |
| F-23 | Et | Et | SCH₃ | H |
| F-24 | H | H | SCH₃ | H |
| F-25 | Ph | Ph | SCH₃ | H |
| F-26 | C₆H₁₃ | C₆H₁₃ | N(CH₃)₂ | N(CH₃)₂ |
| F-27 | Bu | Bu | N(CH₃)₂ | N(CH₃)₂ |
| F-28 | Et | Et | N(CH₃)₂ | N(CH₃)₂ |
| F-29 | H | H | N(CH₃)₂ | N(CH₃)₂ |
| F-30 | Ph | Ph | N(CH₃)₂ | N(CH₃)₂ |
| F-31 | C₆H₁₃ | C₆H₁₃ | N(CH₃)₂ | H |
| F-32 | Bu | Bu | N(CH₃)₂ | H |
| F-33 | Et | Et | N(CH₃)₂ | H |
| F-34 | H | H | N(CH₃)₂ | H |
| F-35 | Ph | Ph | N(CH₃)₂ | H |

Example 7 (G-1)

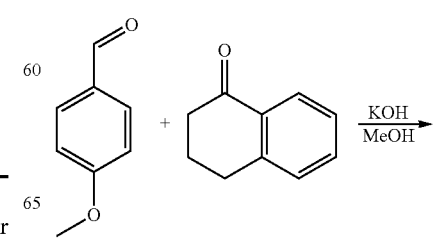

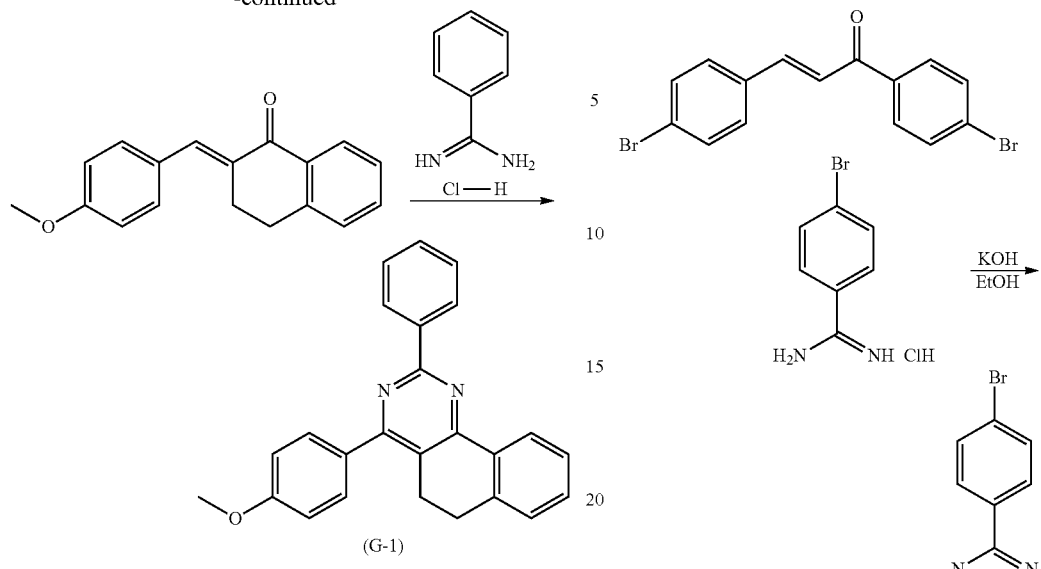

(G-1)

To 14.6 g (0.100 mol) of tetralone and 15.0 g (1.10 mol) p-methoxy-benzaldehyd in 100 ml absolute methanol 660 mg potassium hydroxide are added. The reaction mixture is refluxed for 18 h under argon and then cooled to 25° C. The formed product is filtered off and washed with methanol. To 6.61 g (25.0 mmol) of said product in 50 ml water free ethanol 1.96 g (12.5 mmol) benzamidine hydrochloride are added. A solution of 1.65 g (25.0 mmol) potassium hydroxide in 50 ml water free ethanol is added during 15 min. Dry air is bubbled through the reaction mixture. The reaction mixture is refluxed for 24 h and then poured into water. The water phase is extracted with dichloromethane. The organic phase is dried with magnesium sulfate, the solvent is removed by distillation and the remaining residue is purified by column chromatography (toluene/hexane 1/1). The product G-1 having a melting point of 169° C. is obtained.

Example 8 (H-1)

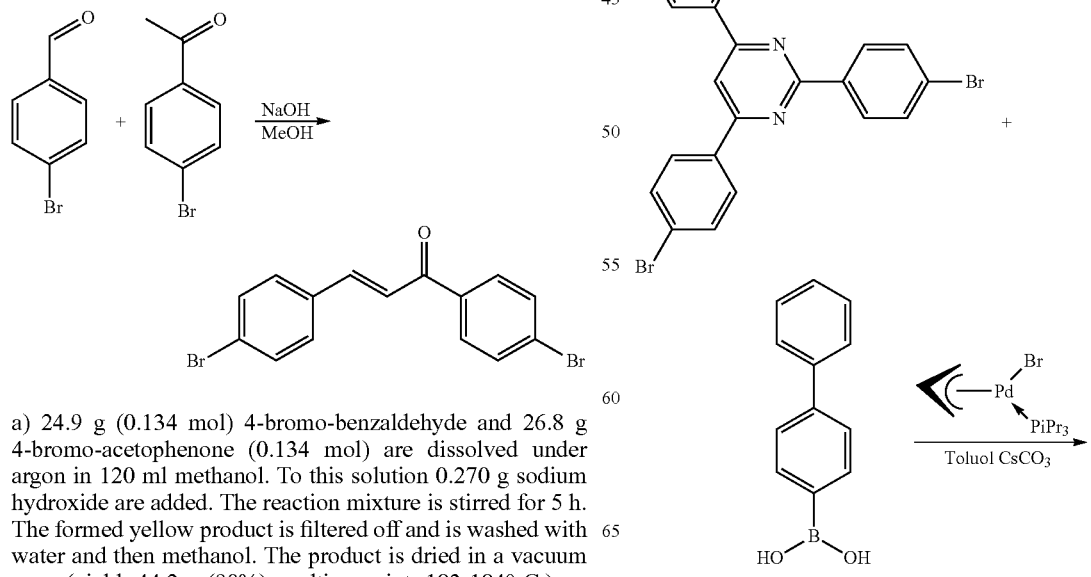

a) 24.9 g (0.134 mol) 4-bromo-benzaldehyde and 26.8 g 4-bromo-acetophenone (0.134 mol) are dissolved under argon in 120 ml methanol. To this solution 0.270 g sodium hydroxide are added. The reaction mixture is stirred for 5 h. The formed yellow product is filtered off and is washed with water and then methanol. The product is dried in a vacuum oven (yield: 44.2 g (90%), melting point: 183-184° C.).

b) To 5.00 g (13.7 mmol) of 1,3-bis-(4-bromophenyl)-2-propen-1-one (1) in 25 ml water free ethanol 1.61 g (6.83 mmol) 4-bromo-benzamidine hydrochloride are added under argon. A solution of 0.90 g (16.1 mmol) potassium hydroxide in 25 ml water free ethanol is added during 15 min. Dry air is bubbled through the reaction mixture. The reaction mixture is refluxed for 24 h and then poured into water. The product is filtered off, washed with ethanol and dried in a vacuum oven (melting point: 321-322° C.).

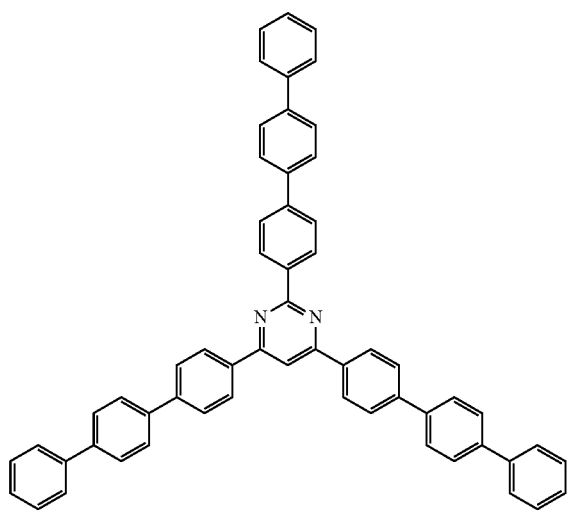

c) To 1.00 g (1.83 mmol) of tris-2,4,6-(4-bromo-phenyl)-pyrimidine and 1.27 g (6.42 mmol) of 4-biphenylboronic acid in 20 ml toluene 5.27 g (16.19 mmol) CsCO₃ in 3 ml water are added under argon. Approximately 10 mg of the Pd catalyst (WO 99/47474) are added and then the reaction mixture is refluxed for 5 h. The product is filtered off, washed with water and acetone. The product is dissolved in dichloromethane and filtered on silica gel. The solvent is removed in vacuum. The obtained product has a melting point of 364-367° C.

Example 9 (H-2)

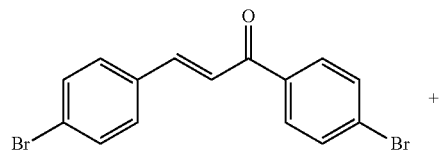

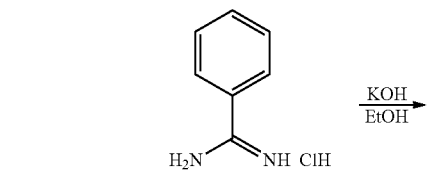

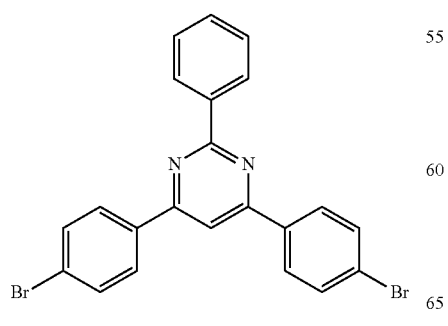

a) The product (melting point: 204-205° C.) is prepared according to the procedure given in example 8b).

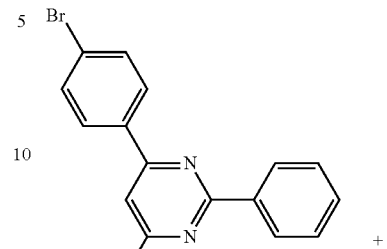

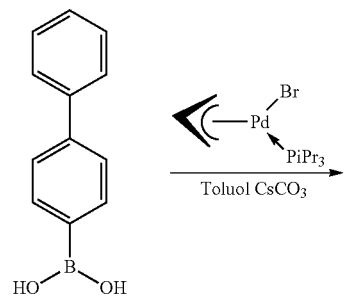

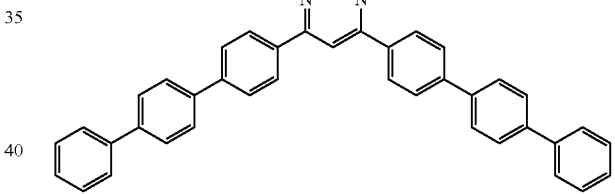

b) The product (melting point: 343-345° C.) is prepared according to the procedure given in example 8c).

Example 10 (H-3)

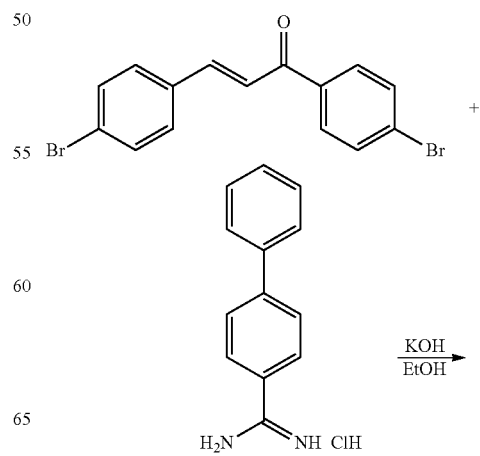

-continued
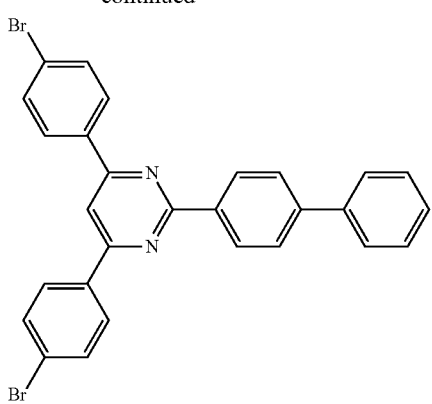
a) The product (melting point: 207-208° C.) is prepared according to the procedure given in example 8b).
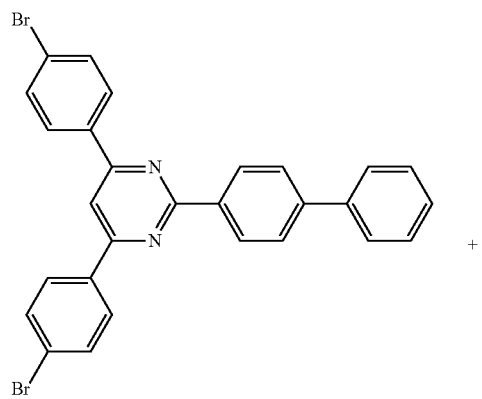
b) The product (melting point: 364-367° C.) is prepared according to the procedure given in example 8c).
Example 11 (H-4)
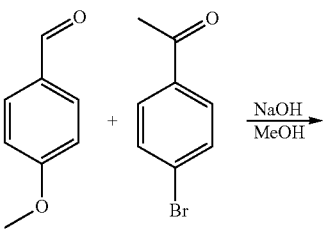
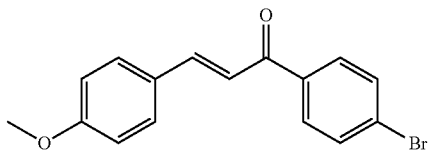
a) The product (melting point: 145-146° C.) is prepared according to the procedure given in example 8b) (yield: 86%).
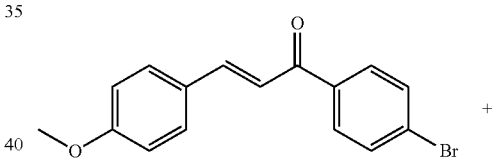
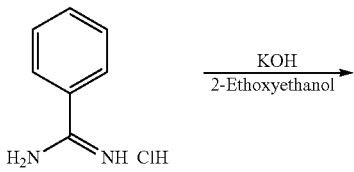
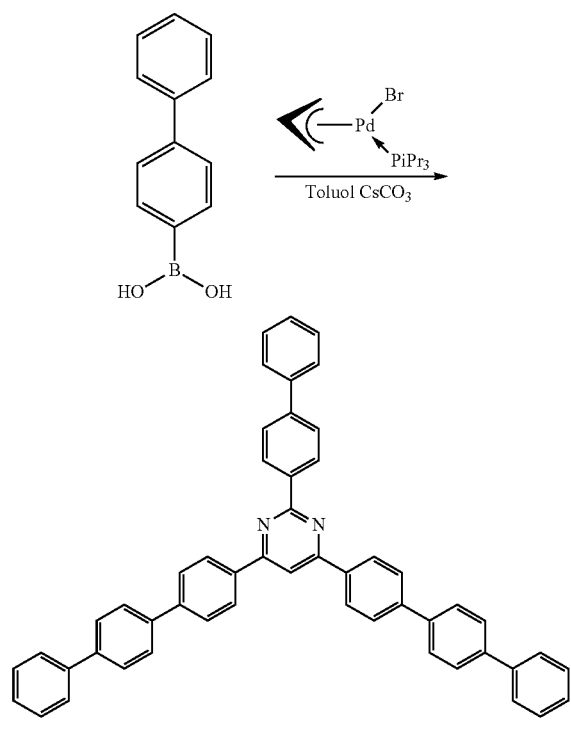
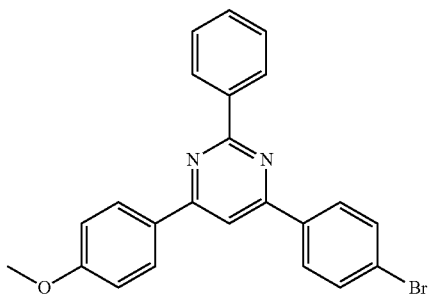

b) The product (melting point: 160° C.) is prepared according to the procedure given in example 8b) (yield: 72%).

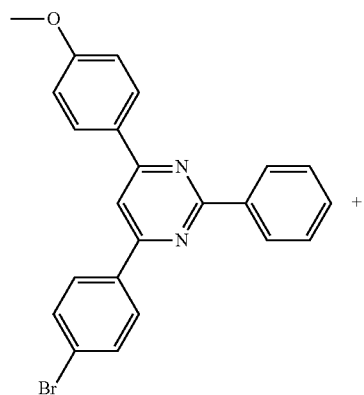

+

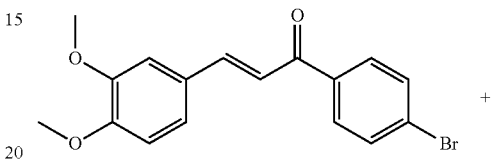

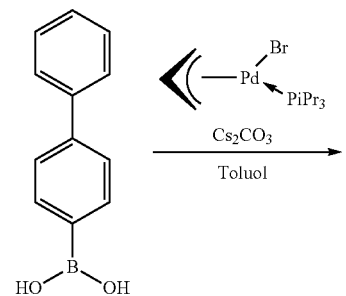

c) The product (melting point: 213-214° C.) is prepared according to the procedure given in example 8c) (yield: 53%).

Example 12 (H-5)

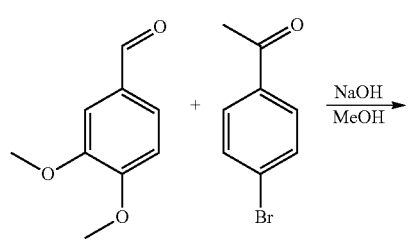

-continued

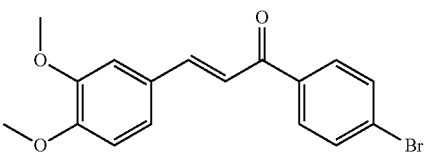

a) The product (melting point: 122-123° C.) is prepared according to the procedure given in example 8b) (yield: 91%).

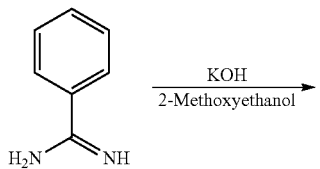

+

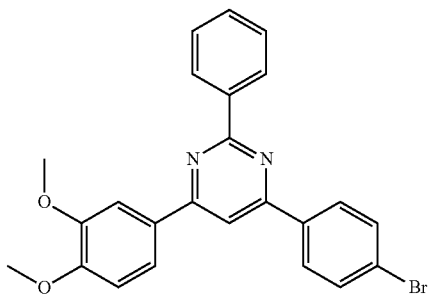

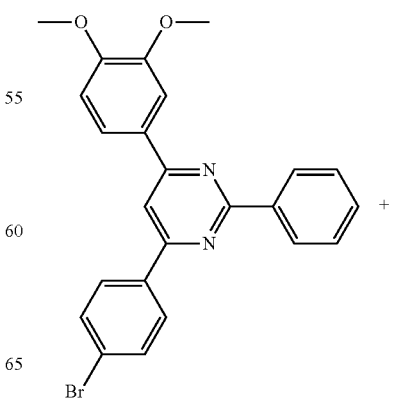

b) The product (melting point: 152-153° C.) is prepared according to the procedure given in example 8b) (yield: 54%).

+

-continued
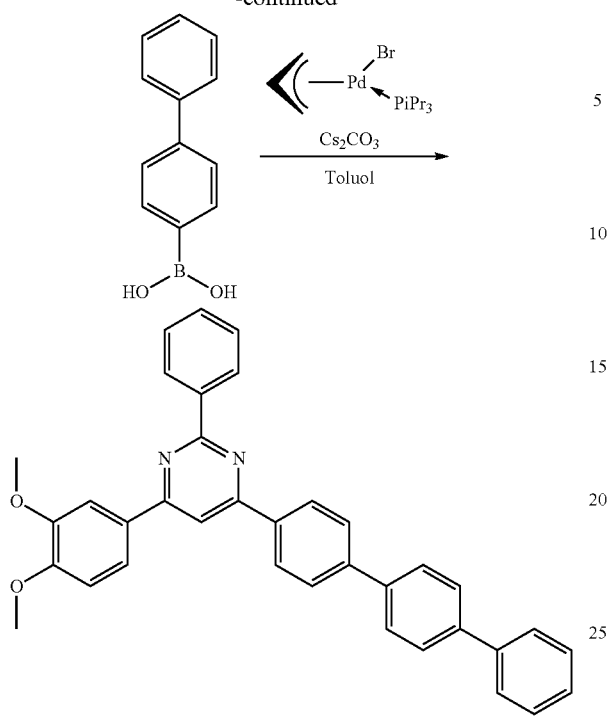
c) The product (melting point: 220-221° C.) is prepared according to the procedure given in example 8c) (yield: 80%).
Example 13 (H-6)
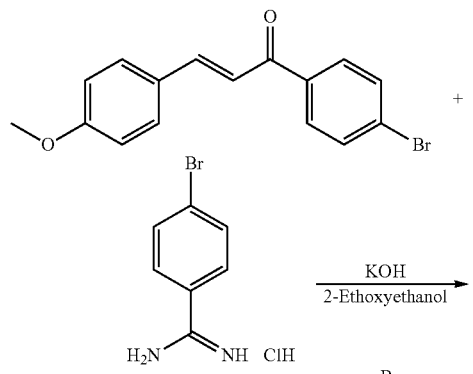
a) The product (melting point: 245-246° C.) is prepared according to the procedure given in example 8b) (yield: 42%).
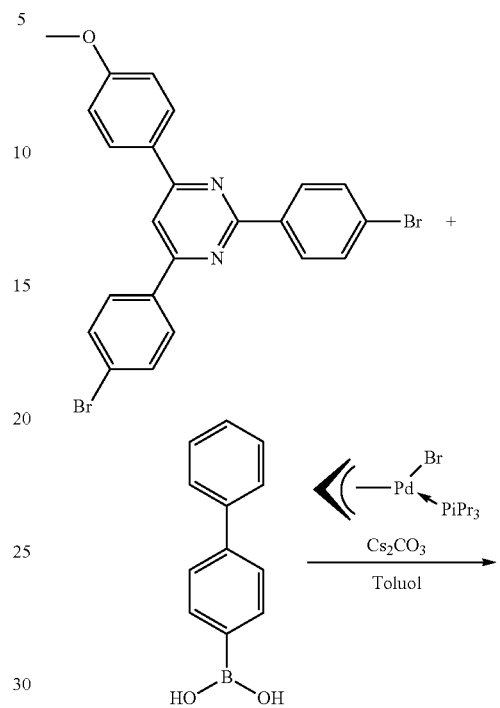
b) The product (melting point: 333-334° C.) is prepared according to the procedure given in example 8c) (yield: 75%).
Example 14 (H-7)
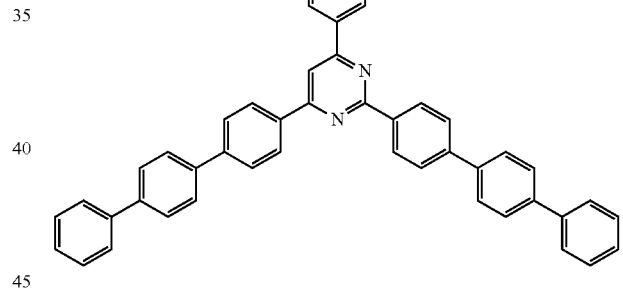
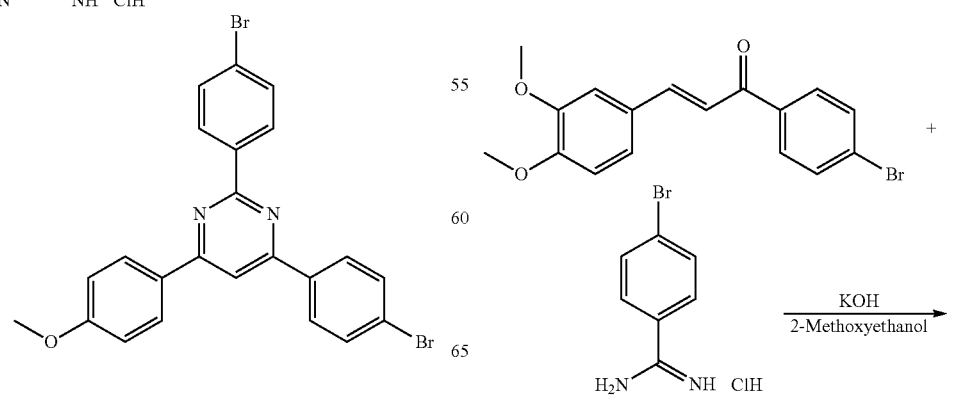

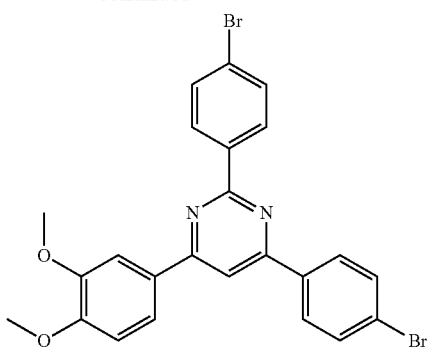

a) The product (melting point: 204-205° C.) is prepared according to the procedure given in example 8b) (yield: 46%).

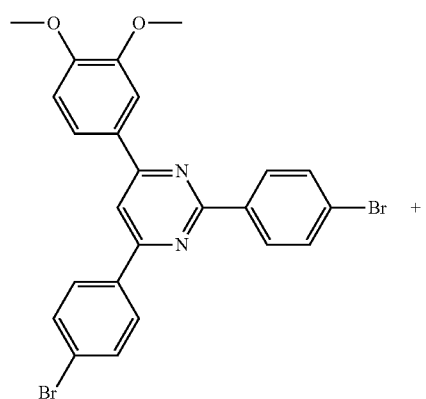

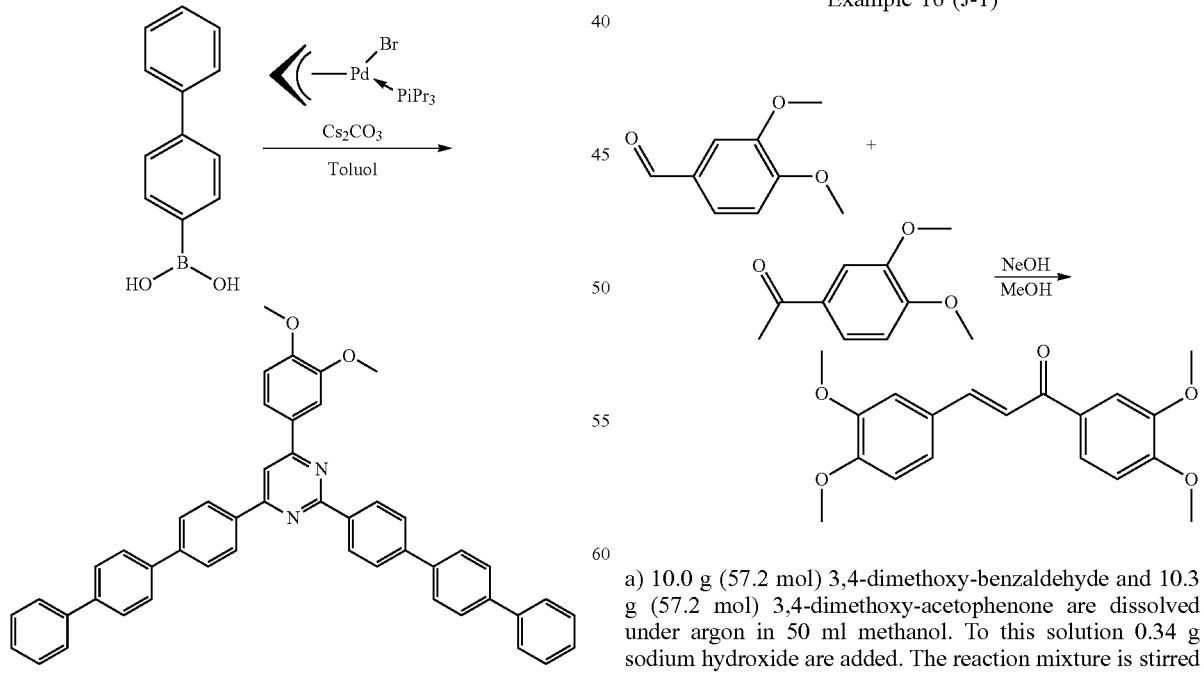

b) The product (melting point: 329-331° C.) is prepared according to the procedure given in example 8c) (yield: 61%).

Example 15

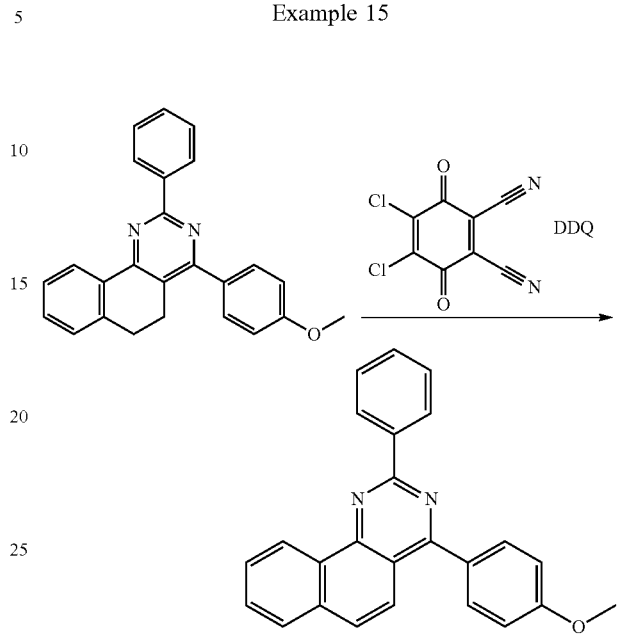

To 264 mg (1.0 mmol) of the pyrimidine (see scheme above) in 20 ml chloroform 454 mg (2.0 mmol) DDQ are added. The reaction mixture is refluxed for 1 day. Additional 908 mg (4.0 mmol) of DDQ are added and the reaction mixture is refluxed for additional 2 days. The reaction mixture is filtered on silica gel with dichloromethane. A column chromatography on silica gel with toluene gives the desired product in 61% yield (mp. 163-165° C.).

Example 16 (J-1)

a) 10.0 g (57.2 mol) 3,4-dimethoxy-benzaldehyde and 10.3 g (57.2 mol) 3,4-dimethoxy-acetophenone are dissolved under argon in 50 ml methanol. To this solution 0.34 g sodium hydroxide are added. The reaction mixture is stirred for 22 h at 40° C. The reaction mixture is cooled to 0° C. and the precipitated product is filtered off. The product is dried in vacuum (yield: 18.2 g (97%), melting point: 108-110° C.).

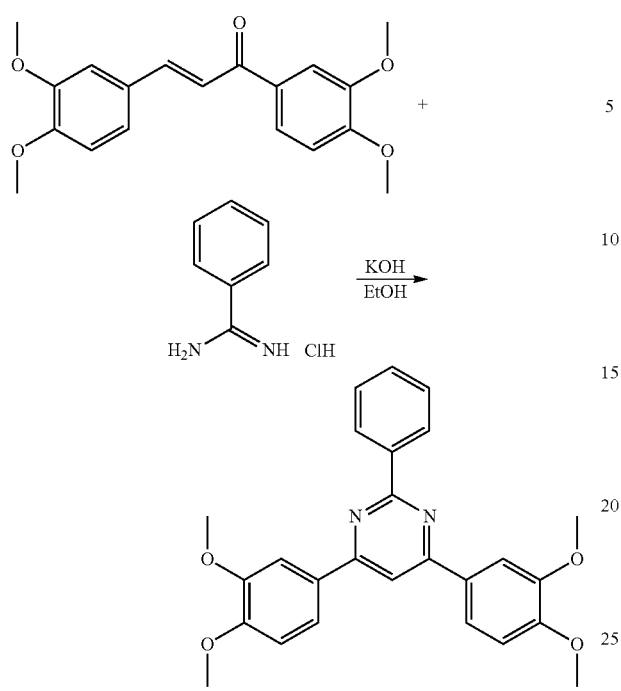

b) To 7.00 g (21.3 mmol) of 1,3-bis-(3,4-dimethoxy-phenyl)-2-propen-1-one (1) in 40 ml water free ethanol 1.67 g (10.7 mmol) benzamidine hydrochloride are added under argon. A solution of 1.41 g (25.1 mmol) potassium hydroxide (85%) in 40 ml water free ethanol is added during 20 min. Dry air is bubbled through the reaction mixture. The reaction mixture is refluxed for 48 h and then poured into water. The product is filtered off and washed with ethanol. A column chromatography on silica gel with toluene gives the desired product J-1 (melting point: 157-158° C.).

Example 17 (J-2)

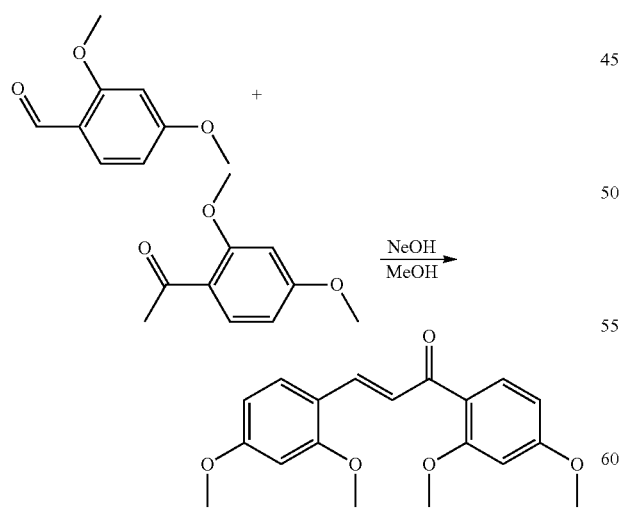

a) 10.0 g (57.2 mol) 2,4-dimethoxy-benzaldehyde and 10.3 g 2,4-dimethoxy-acetophenone (57.2 mol) are dissolved under argon in 50 ml methanol. To this solution 0.34 g sodium hydroxide are added. The reaction mixture is stirred for 48 h at 40° C. The reaction mixture is diluted with water and the precipitated product is filtered off. The product is washed with water and dried in vacuum (melting point: 127-129° C.).

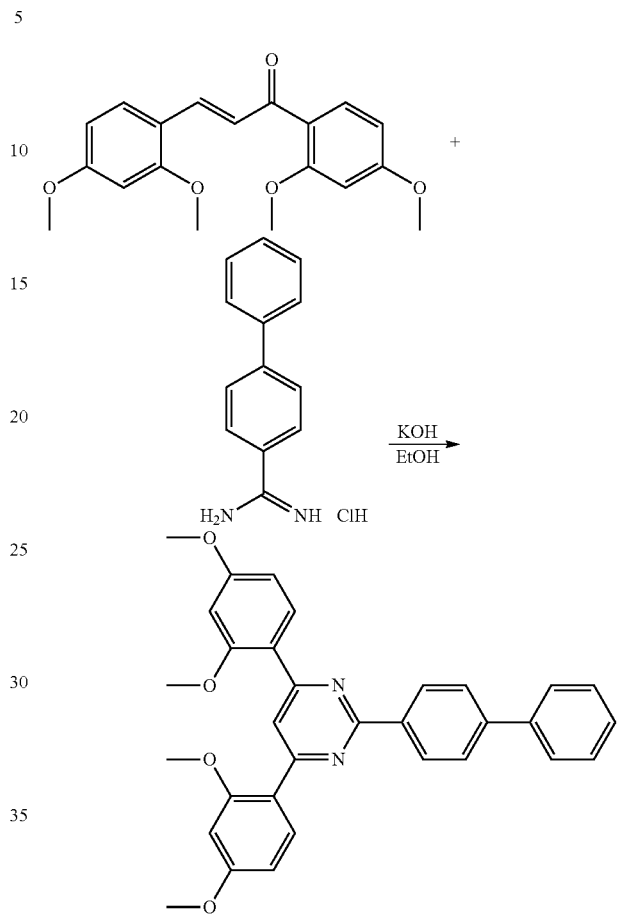

b) To 6.60 g (20.1 mmol) of 1,3-bis-(2,4-dimethoxy-phenyl)-2-propen-1-one (1) in 40 ml water free ethanol 2.34 g (10.1 mmol) biphnenyl-benzamidine hydrochloride are added under argon. A solution of 1.41 g (25.1 mmol) potassium hydroxide (85%) in 40 ml water free ethanol is added during 15 min. Dry air is bubbled through the reaction mixture. The reaction mixture is refluxed for 48 h and then poured into water. The water phase is extracted with dichloromethane. The organic phase is dried with MgSO₄ and the solvent is removed in vacuum. A column chromatography on silica gel with toluene/hexane 3/2 give the desired product J-2 (melting point: 165-167° C.).

Example 18 (J-4)

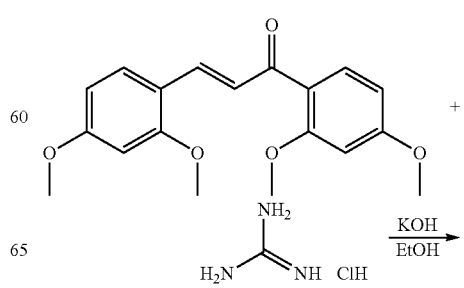

-continued

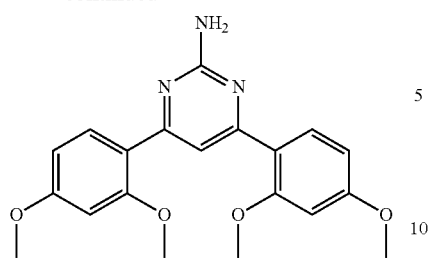

To 5.50 g (15.2 mmol) of 1,3-bis-(2,4-dimethoxy-phenyl)-2-propen-1-one (1) in 30 ml water free ethanol 0.87 g (9.14 mmol) guanidine hydrochloride are added under argon. A solution of 1.21 g (21.5 mmol) potassium hydroxide (85%) in 30 ml water free ethanol is added during 15 min. Dry air is bubbled through the reaction mixture. The reaction mixture is refluxed for 48 h and then poured into water. The water phase is extracted with dichloromethane. The organic phase is dried with MgSO$_4$ and the solvent is removed in vacuum. A column chromatography on silica gel with dichloromethane/ethyl acetate 2/1 gives the desired product (melting point: 211-213° C.).

Example 19 (J-5)

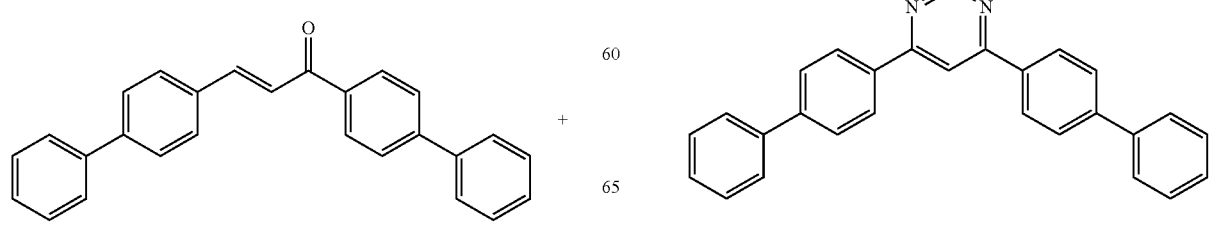

a) To a suspension of 0.69 g sodium hydride in 25 ml terahydrofurane (THF) 5.38 g (27.4 mmol) 4-acetyl-biphenyl are added at 0° C. under argon. After 1 h 5.00 g (27.4 mmol) 4-bihenylcarbadehyde in 25 ml THF are added. The reaction mixture is stirred for 19 h at 25° C. The formed precipitate is filtered off and washed with THF. The product is refluxed for 1 h in 100 ml iso-propanol and 30 ml water. The product is filtered off and dried in vacuum.

-continued

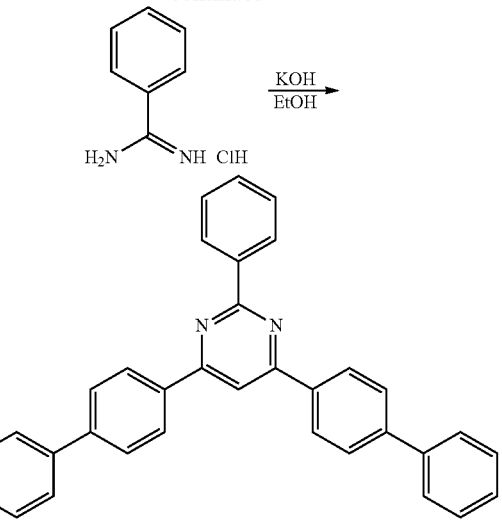

b) The desired product J-5 (melting point: 245-246° C.) is prepared according to the procedure given in example 17b).

Example 20 (J-6)

The product J-6 (melting point: 243-246° C.) is prepared according to the procedure given in example 17b).

Example 21 (J-7)

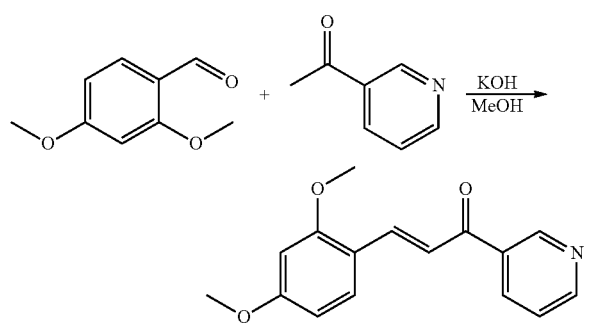

a) 18.3 g (0.100 mol) 2,4-dimethoxy-benzaldehyde and 12.1 g (0.100 mol) 3-acetyl pyridine are dissolved under argon in 100 ml methanol. To this solution 0.66 g sodium hydroxide are added. The reaction mixture is refluxed for 18 h. The reaction mixture is poured into water and extracted with dichloromethane. The organic phase is dried with $MgSO_4$ and the solvent is removed in vacuum. A column chromatography on silica gel with toluene/ethyl acetate 2/1 give the desired product (yield: 7.3 g (27%)).

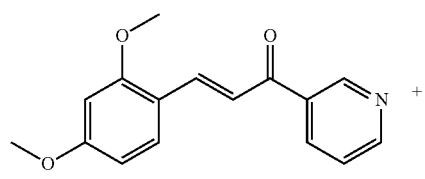

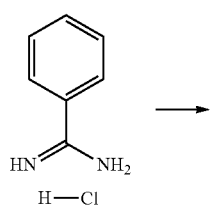

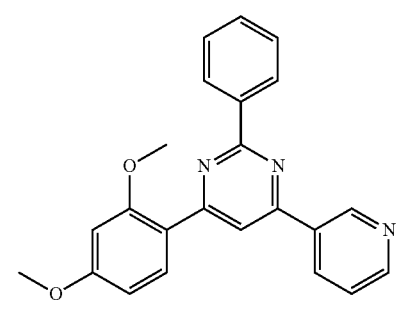

b) The product J-7 (melting point: 136° C.) is prepared according to the procedure given in example 17b).

Example 22 (K-1)

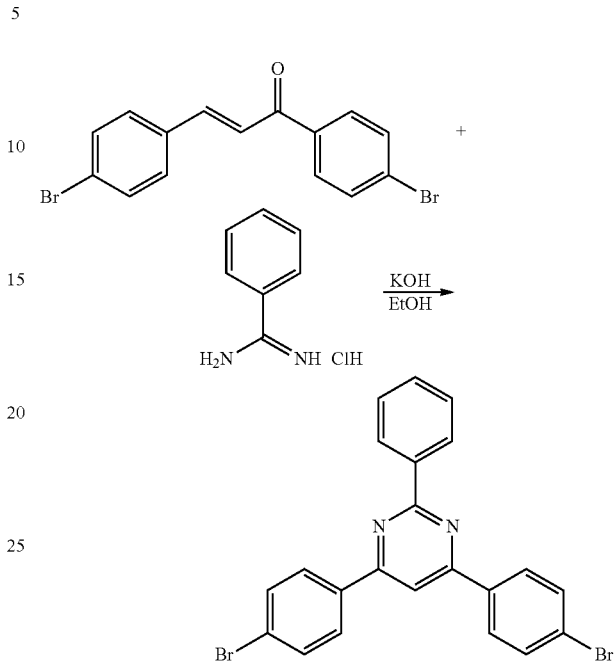

a) To 10.0 g (27.3 mmol) of 1,3-bis-(4-bromophenyl)-2-propen-1-one in 70 ml ethanol 2.14 g (13.7 mmol) benz-amidine hydrochloride are added under argon. A solution of 1.80 g (32.1 mmol) potassium hydroxide (85%) in 50 ml ethanol is added during 15 min. Dry air is bubbled through the reaction mixture. The reaction mixture is refluxed for 24 h and then is poured into water. The product is filtered off, washed with water and 10% tartaric acid, crystallized from glacial acetic acid and washed with ethanol (yield: 9.2 g (58%); melting point: 203-205° C.).

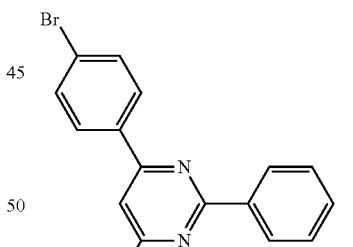

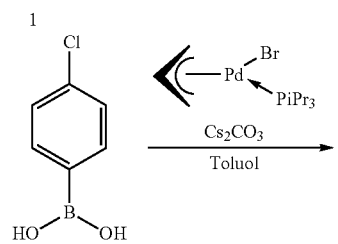

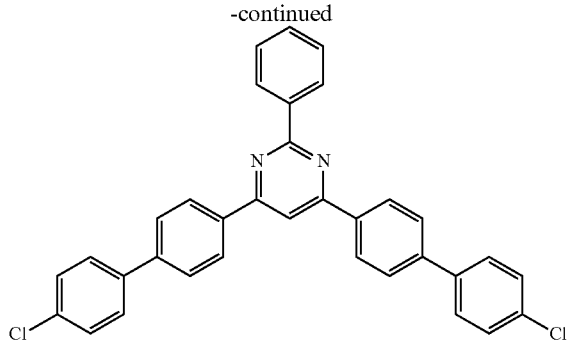

b) To 4.45 g (9.55 mmol) 4,6-tris-(p-bromophenyl)-2-phenyl-pyrimidine in 200 ml toluene 2.99 g (19.1 mmol) 4-chloro-phenylboronic acid are added. The suspension is refluxed under argon. Argon is passed through the reaction mixture. 9.33 g (28.6 mmol) of caesium carbonate in 6 ml water are added dropwise to the reaction mixture. Then 0.40 g of the catalyst are added. The reaction mixture is refluxed for 16 h and then the solids are filtered off. The solvent is removed in vacuum. The residue is dissolved in dichloromethane and is washed with water. The organic phase is dried with magnesium sulfate. The solvent is removed in vacuum. The product is crystallized from 100 ml ethanol (yield: 99%; melting point: 258-259° C.).

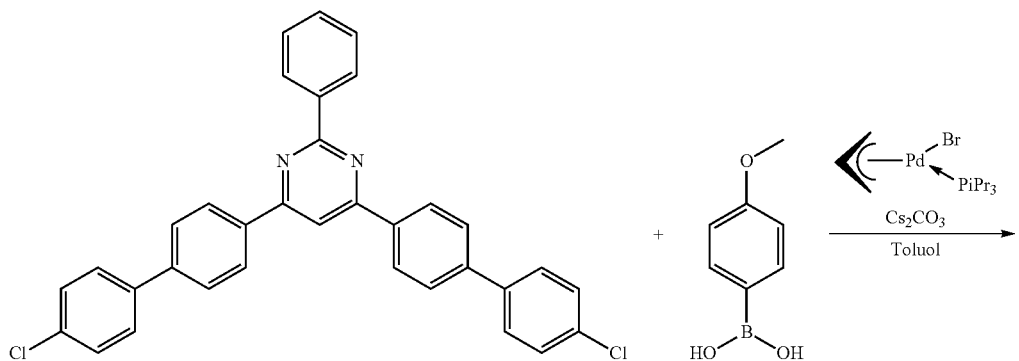

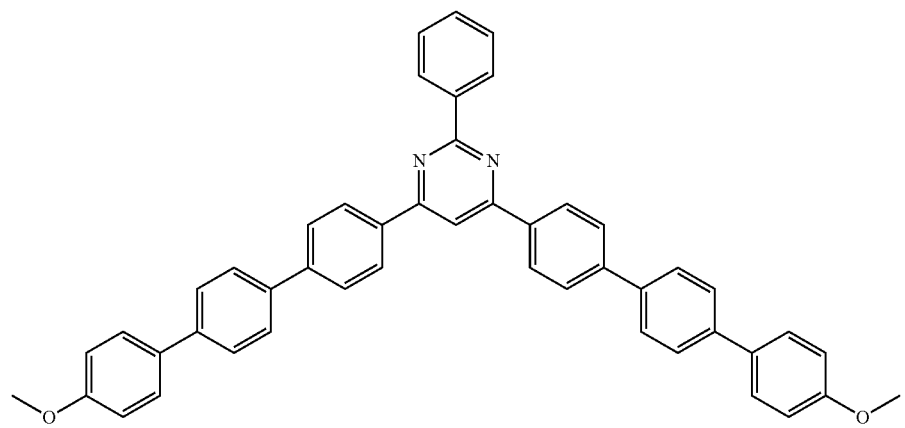

c) To 1.00 g (1.89 mmol) 4,6-bis-(p-bromophenyl)-2-phenyl-pyrimidine in 45 ml toluene 287 mg (1.89 mmol) 4-metoxy-biphenylboronic acid are added. Argon is passed through the reaction mixture. 1.23 g (3.78 mmol) of caesium carbonate in 6 ml water is added dropwise to the reaction mixture. Then 20 mg of the catalyst is added. The reaction mixture is refluxed for 18 h. Additional 4-methoxy-biphenylboronic acid and caesium carbonate is added in a 1 to 1 molar ratio until the reaction is complete. The product is filtered off and is washed with ethanol, water and again ethanol. The product is dissolved in boiling DMF, filtered on super gel (Fluka 56678, CAS [91053-39-3]) and crystallized (yield: 0.90 g (71%); melting point: 345-348° C.).

In a manner analogous to Example 22 Compounds K-2 to K-15 are obtained.

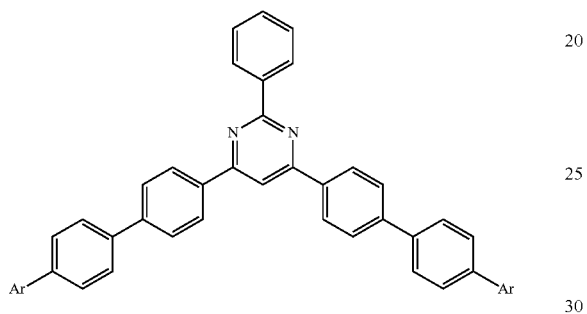

| Cpd. | Ar |
|------|----|
| K-1  | 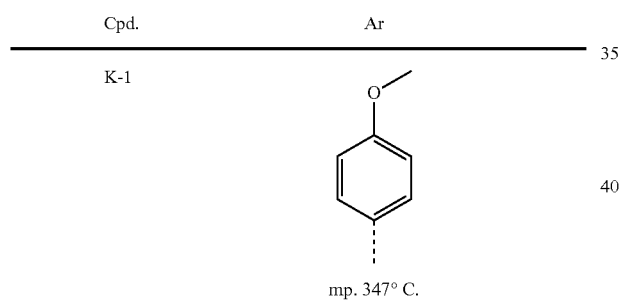 mp. 347° C. |
| K-2  | 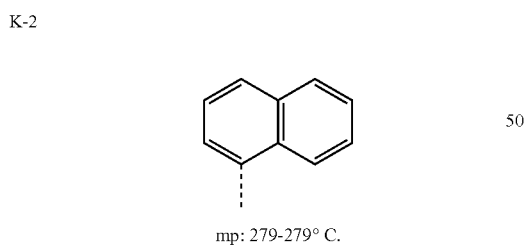 mp: 279-279° C. |
| K-3  | 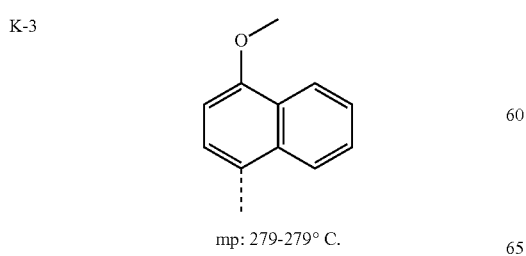 mp: 279-279° C. |

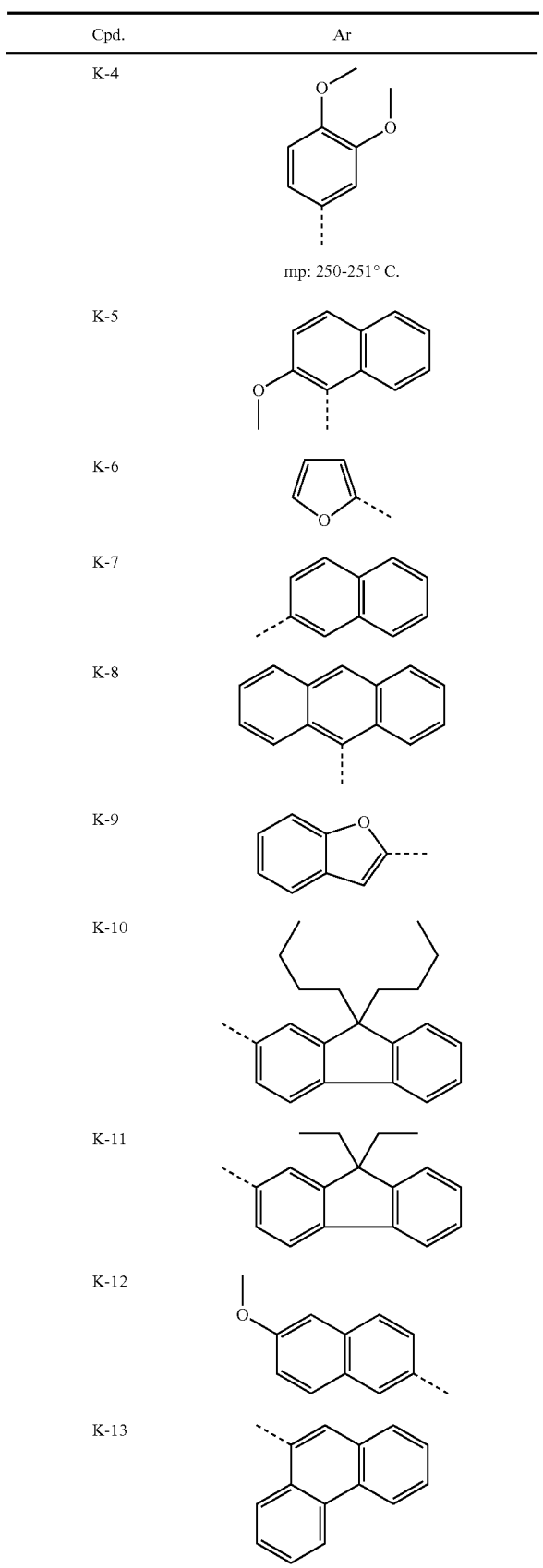

-continued

| Cpd. | Ar |
|------|----|
| K-4  | mp: 250-251° C. |
| K-5  |  |
| K-6  |  |
| K-7  |  |
| K-8  |  |
| K-9  |  |
| K-10 |  |
| K-11 |  |
| K-12 |  |
| K-13 |  |

-continued
| Cpd. | Ar |
|---|---|
| K-14 | 4-biphenylyl |
| K-15 | 4-fluorophenyl (mp: 328-330° C.) |
| K-16 | phenyl |
a) The product is prepared according to the procedure given in example 22a).
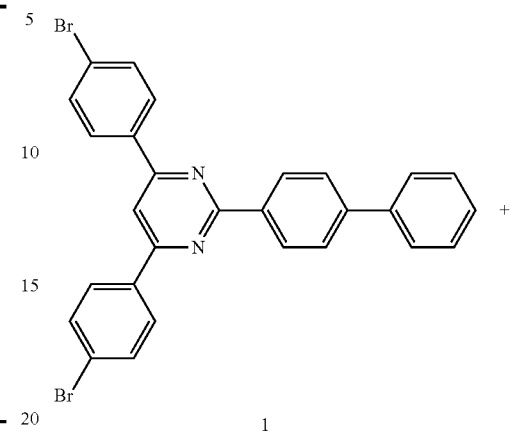
1
Example 23 (L-1)
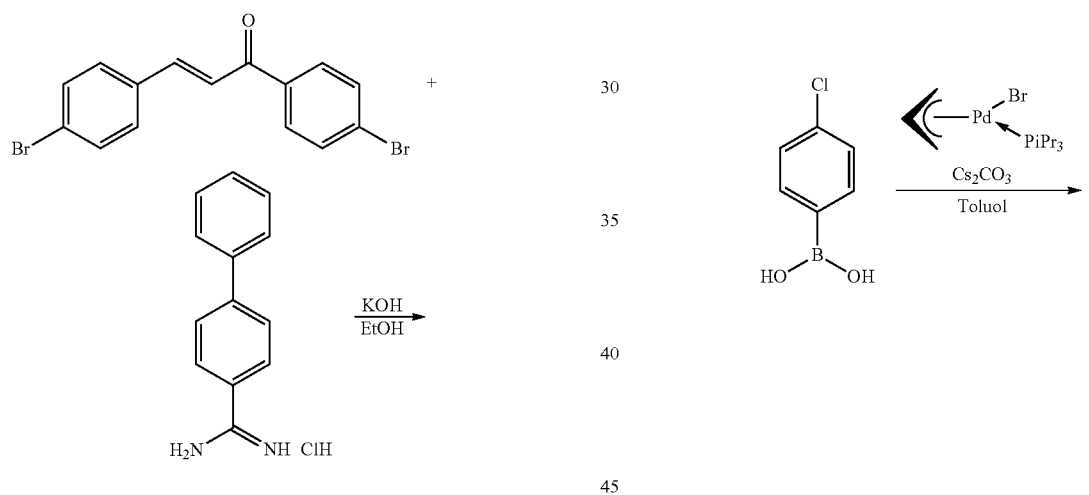
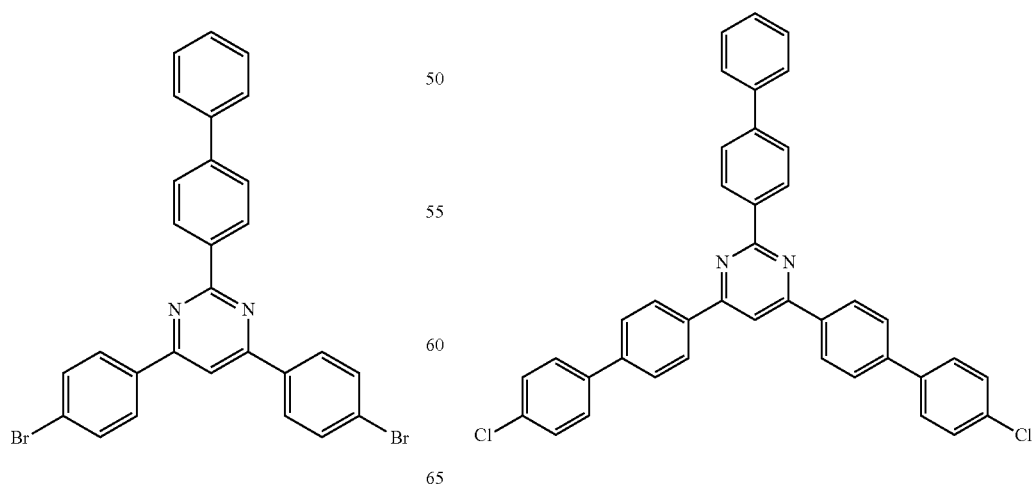

b) The product is prepared according to the procedure given in example 22b).
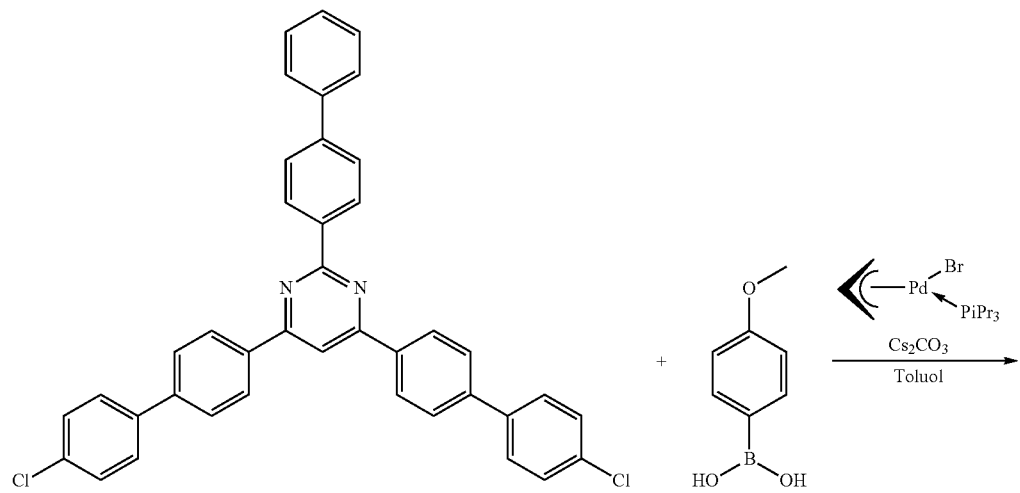
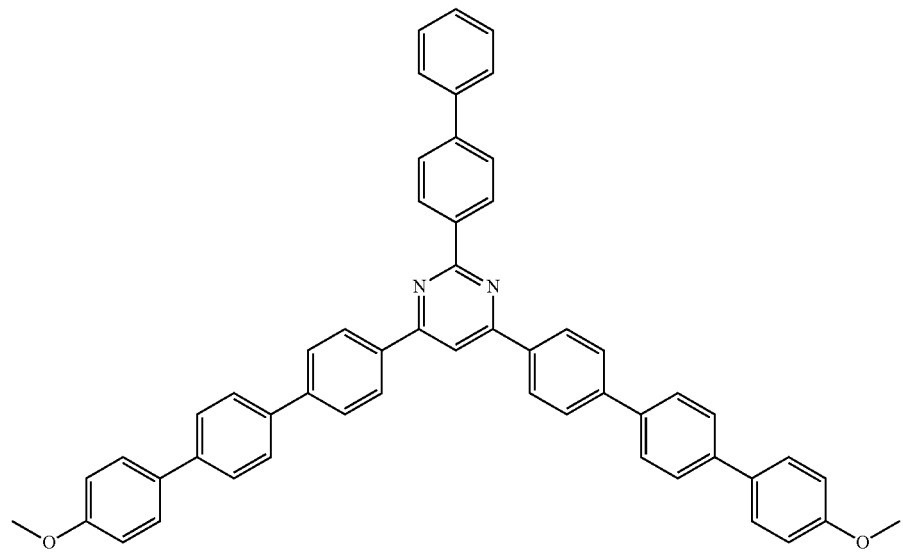

c) The product is prepared according to the procedure given in example 22c).
In a manner analogous to Example 23 Compounds L-2 to L-15 are obtained.
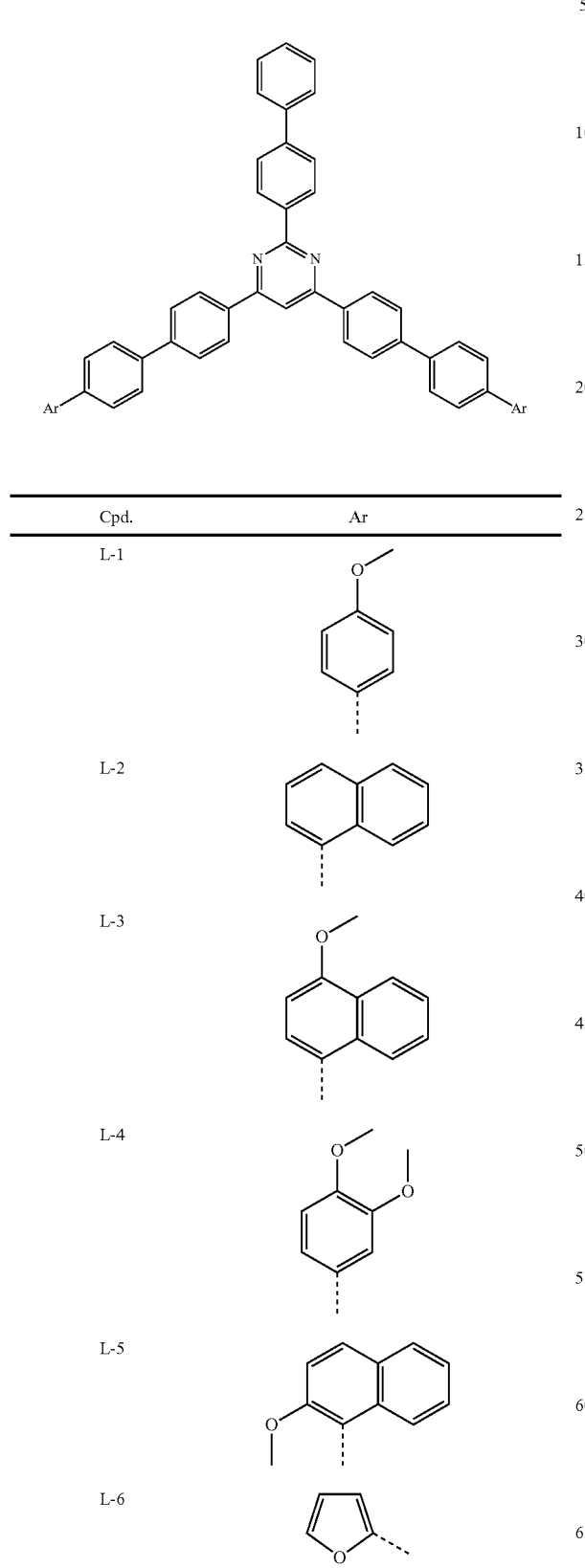
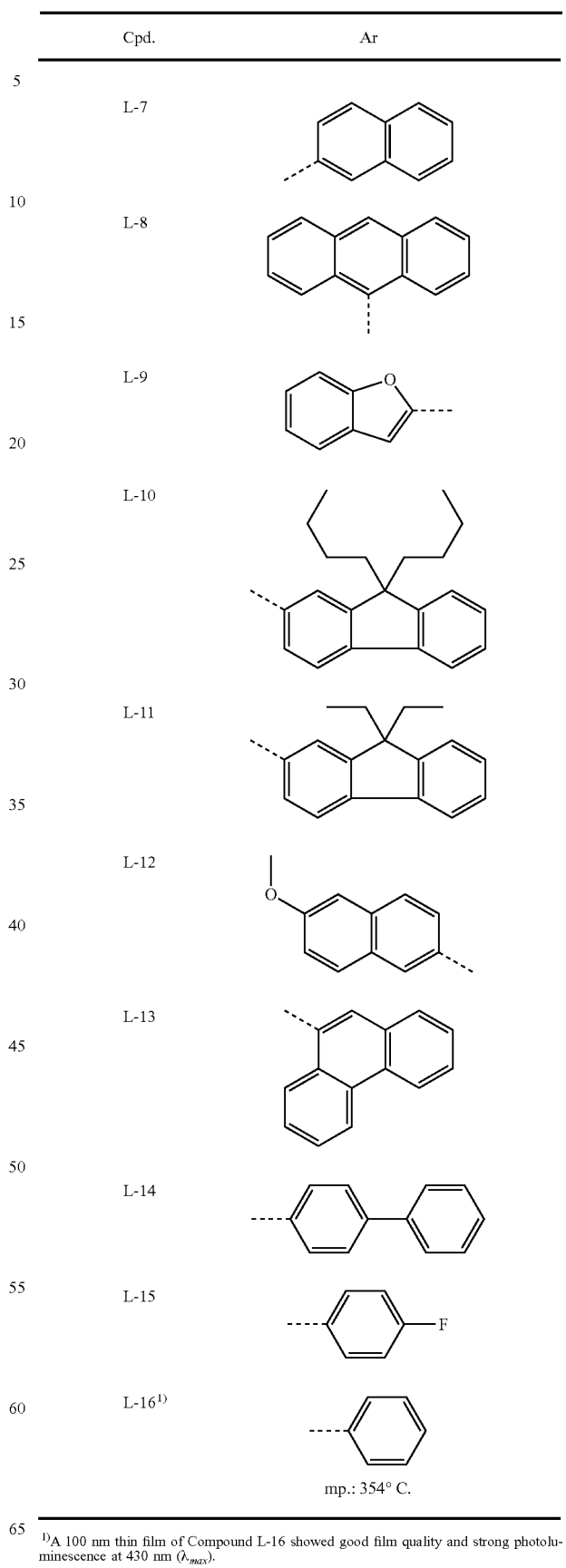
[1] A 100 nm thin film of Compound L-16 showed good film quality and strong photoluminescence at 430 nm ($\lambda_{max}$).

Example 24 (M-1)
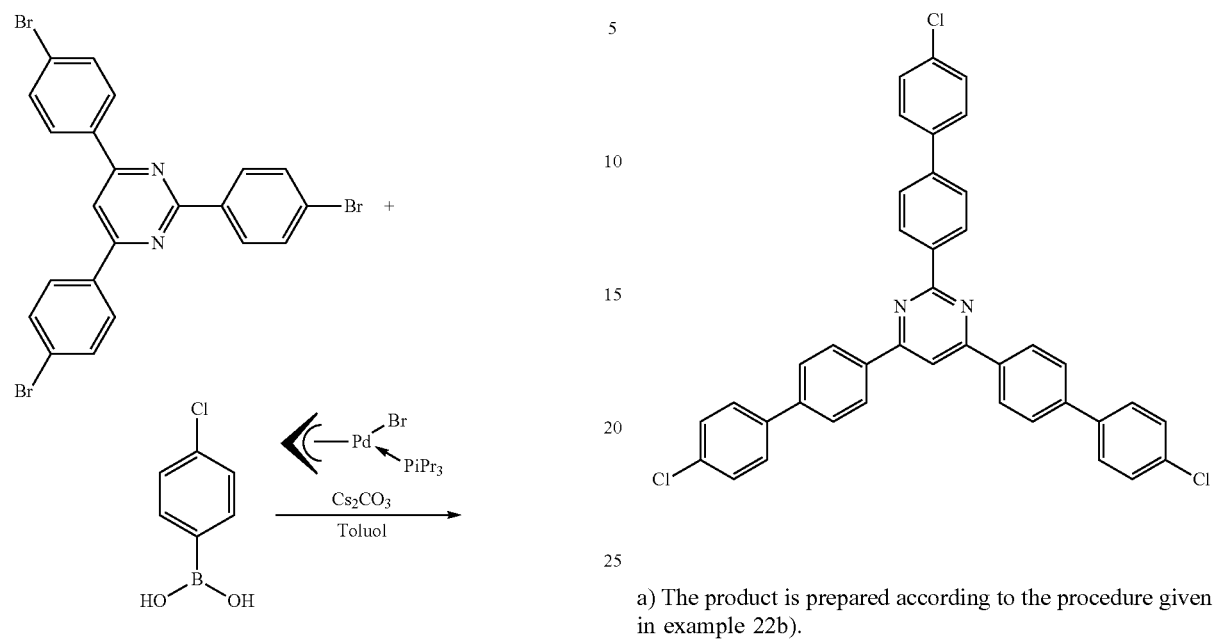
a) The product is prepared according to the procedure given in example 22b).
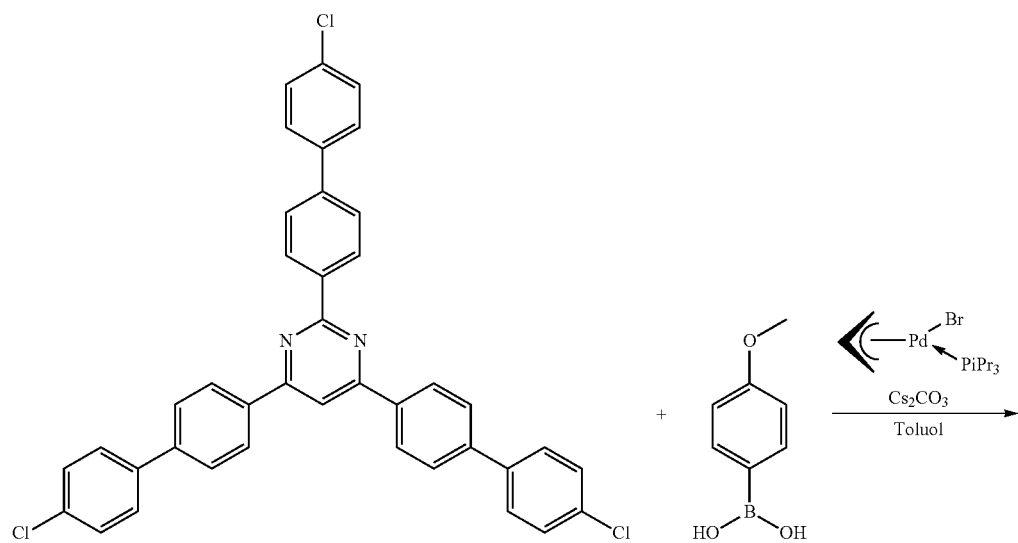

-continued
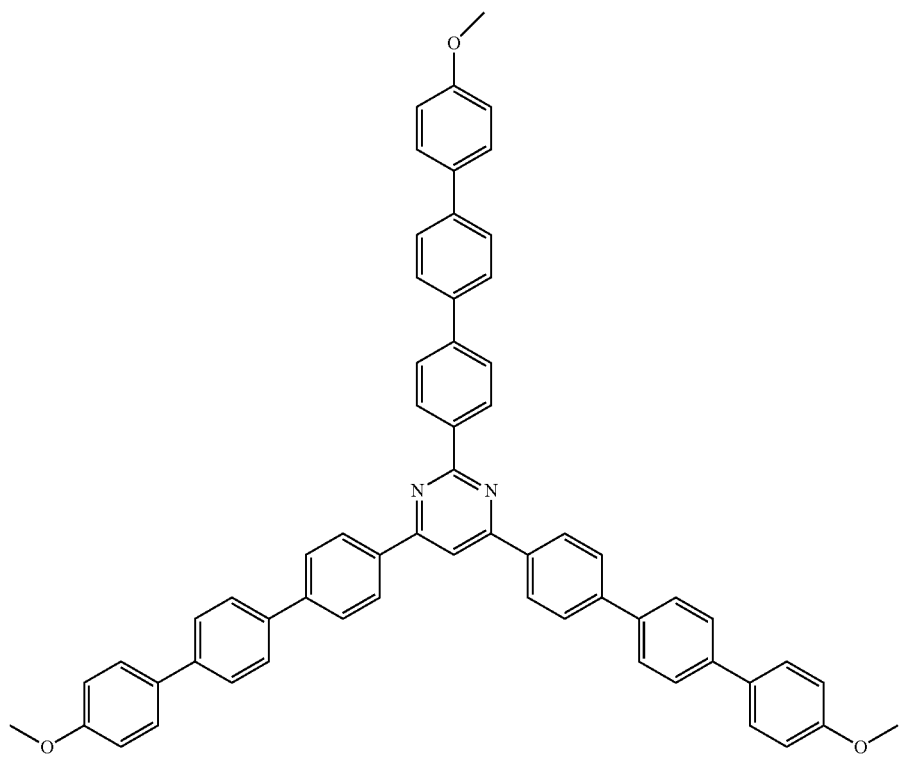
b) The product is prepared according to the procedure given in example 22c).
In a manner analogous to Example 24 Compounds M-2 to M-15 are obtained.
| Cpd. | Ar |
|---|---|
| M-1 | 4-methoxyphenyl |
| M-2 | 1-naphthyl<br>mp.: 376-378° C. |
| M-3 | 4-methoxy-1-naphthyl |

| Cpd. | Ar |
|---|---|
| M-4 | (3,4-dimethoxyphenyl) mp.: 243-250° C. |
| M-5 | (2-methoxynaphthalen-1-yl) |
| M-6 | (furan-2-yl) |
| M-7 | (naphthalen-2-yl) |
| M-8 | (anthracen-9-yl) |
| M-9 | (benzofuran-2-yl) |
| M-10 | (9,9-dipentylfluoren-2-yl) |
| M-11 | (9,9-diethylfluoren-2-yl) |
| M-12 | (6-methoxynaphthalen-2-yl) |
| M-13 | (phenanthren-9-yl) |
| Cpd. | Ar |
|---|---|
| M-14 | (biphenyl-4-yl) |
| M-15 | (4-fluorophenyl) |
| M-16 | (phenyl) mp.: 340° C. |
Example 25 (N-1)
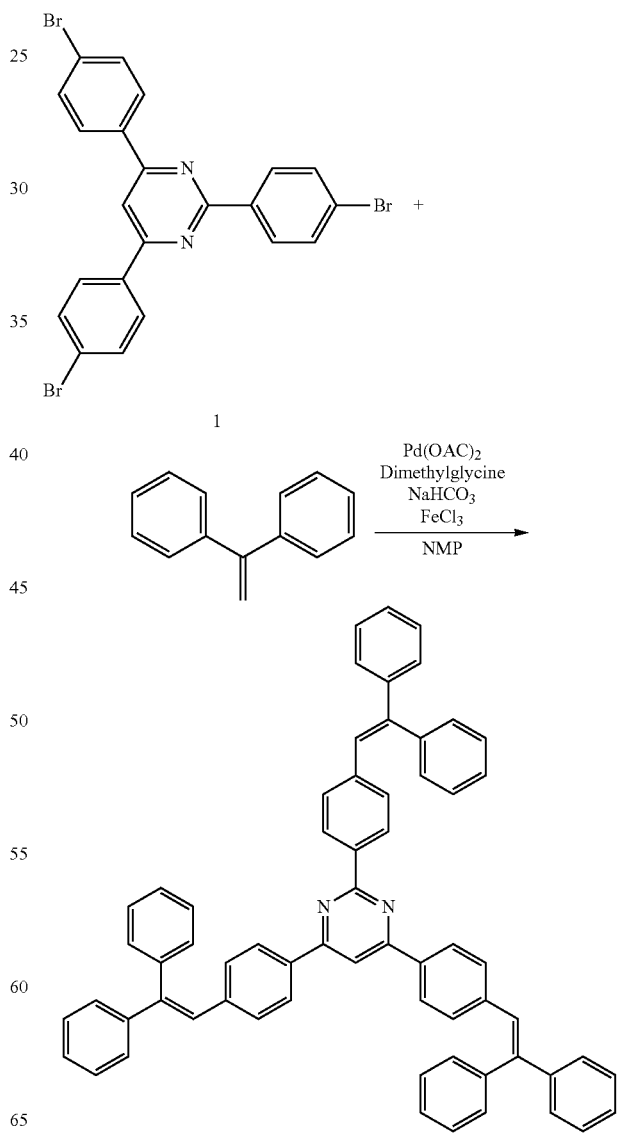

1.0 g (1.83 mmol) 2,4,6-tris-(p-bromophenyl)-pyrimidine, 1.49 g (8.26 mmol) 1,1-diphenylethylen, 40 mg Palladium-(II)-acetate, 150 mg (1.47 mmol) dimethylglycine, 1.39 g (16.5 mmol) sodium hydrogen carbonate and 70 mg (0.46 mmol) $FeCl_3$ are dissolved in 8 ml N-methyl-pyrrolidone. The reaction mixture is heated for 48 h at 150° C. The reaction mixture is poured into water and 20% hydrochloric acid is added. The water phase is extracted with dichloromethane. The organic phase is dried with magnesium sulfate. The solvent is distilled off. A column chromatography (silica gel, toluene/hexane ⅓) result in the desired product (119.5-120.5° C.).

Example 26

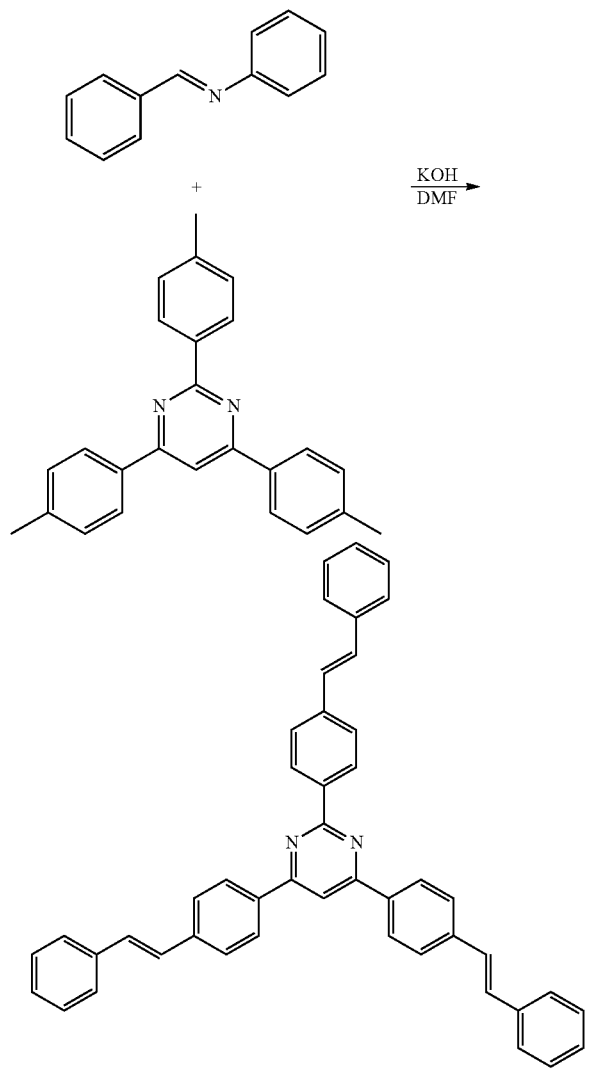

The product is synthesized as described in Example 31 of CH-A-542212.

Application Example 1

Present compounds A1, A2, A3, B1, B2, C1, G1 and H1 as light emitting materials, respectively, 2,5-bis(1-naphthyl)-1,3,4-oxadiazole and a polycarbonate resin in a weight ratio of 5:3:2 are dissolved in tetrahydrofuran, and the solution is spin-coated on a cleaned glass substrate with an ITO electrode to form a light-emitting layer having a thickness of 100 nm. An electrode having a thickness of 150 nm is formed thereon from a magnesium/indium alloy having a magnesium/indium mixing ratio of 10/1, to obtain an organic EL device. The device exhibits light emission with excellent brightness and efficiency at a direct current voltage of 5 V.

Application Example 2

Compounds A1, A2, A3, B1, B2, C1, G1 and H1, respectively, are vacuum-deposited on a cleaned glass substrate with an ITO electrode to form a light-emitting layer having a thickness of 100 nm. An electrode having a thickness of 100 nm is formed thereon from a magnesium/silver alloy having a magnesium/silver mixing ratio of 10/1, to obtain an organic EL device. The light-emitting layer is formed by deposition under a vacuum of $10^6$ Torr at a substrate temperature of room temperature. The device shows emission having an excellent brightness and efficiency at a direct current voltage of 5 V.

Application Example 3

Compounds A1, A2, A3, B1, B2, C1, G1 and H1, respectively, are dissolved in methylene chloride tetrahydrofuran, and the solution is spin-coated on a cleaned glass substrate with an ITO electrode to form a light-emitting layer having a thickness of 50 nm. Then, aluminum bis(2-methyl-8-quinolinate)(2-naphtolate) is vacuum-deposited to form an electron-injecting layer having a thickness of 10 nm, and an electrode having a thickness of 100 nm is formed thereon from a magnesium/aluminum alloy having a magnesium/aluminum mixing ratio of 10/1, to obtain an organic EL device. The light-emitting layer and the electron-injecting layer are formed by deposition under a vacuum of $10^6$ Torr at a substrate temperature of room temperature. The device shows an emission having an excellent brightness and efficiency at a direct current voltage of 5 V.

Application Example 4

Compounds A1, A2, A3, B1, B2, C1, G1 and H1, respectively, are vacuum-deposited on a cleaned glass substrate with an ITO electrode to form a light-emitting layer having a thickness of 50 nm. Then, aluminum tris(8-hydroxyquinolinate) is vacuum-deposited to form an electron-injecting layer having a thickness of 10 nm and an electrode having a thickness of 100 nm is formed thereon from an aluminum/lithium alloy having an aluminum/lithium mixing ratio of 50/1, to obtain an organic EL device. A hole-injecting layer and the light-emitting layer are formed by deposition under a vacuum of $10^6$ Torr at a substrate temperature of room temperature. The device shows a light emission having an excellent brightness and efficiency at a direct current voltage of 5 V.

Application Example 5

One of hole-injecting materials (H-1) to (H-6) is vacuum-deposited on a cleaned glass substrate with an ITO electrode, to form a hole-injecting layer having a thickness of 30 nm. Then, one of light-emitting materials A1, A2, A3, B1, B2, C1, G1 and H1, respectively is vacuum-deposited to form a light-emitting layer having a thickness of 30 nm. Further, one of electron-injecting materials (E-1) to (E-6) is vacuum-deposited to form an electron-injecting layer having a thickness of 30 nm. An electrode having a thickness of 150 nm is formed thereon from a magnesium/silver alloy having a magnesium/silver mixing ratio of 10/1, to obtain an organic EL device. Each layer is formed under a vacuum of $10^6$ Torr at a substrate temperature of room temperature. All the organic EL devices obtained in these Examples shows high brightness and efficiency.

(H-1)
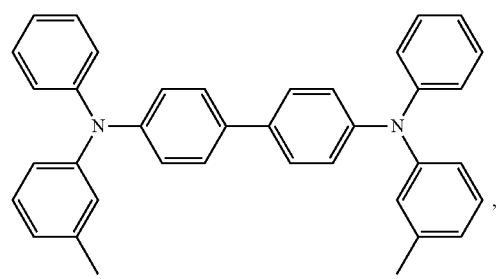
(H-2)
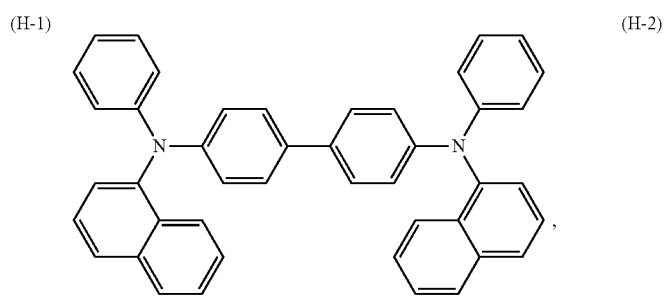
(H-3)
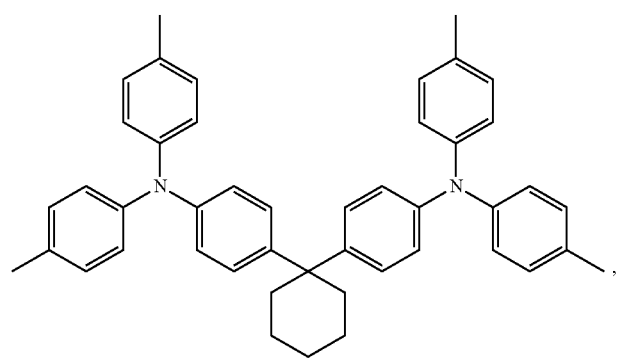
(H-4)
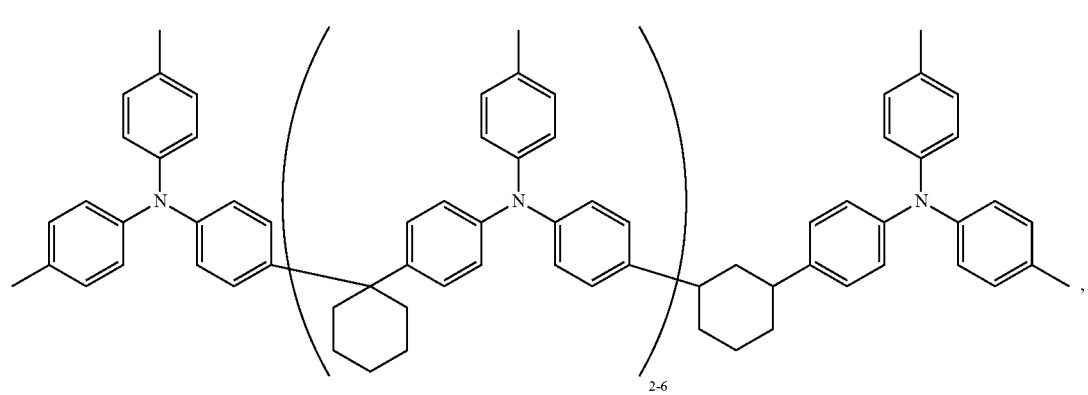
(H-5)
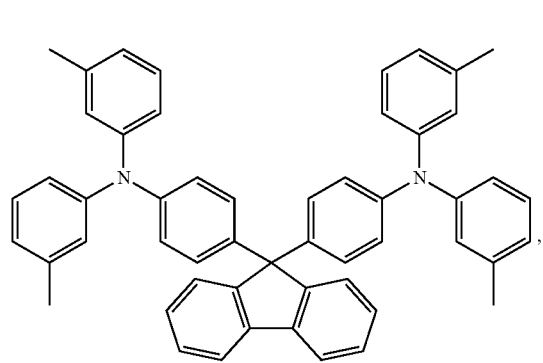
(H-6)
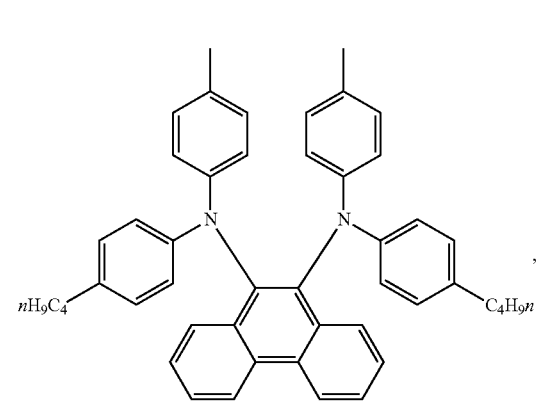

-continued

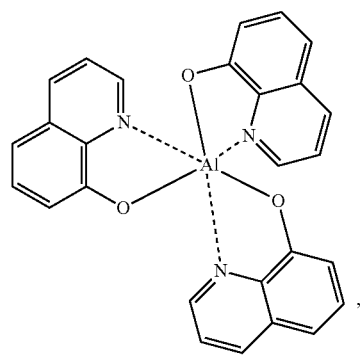
(E-1)

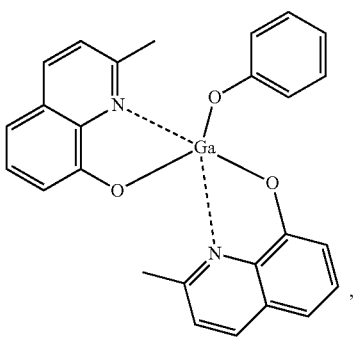
(E-2)

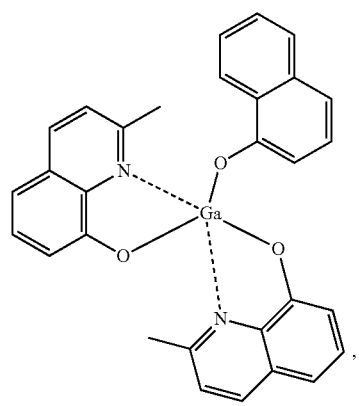
(E-3)

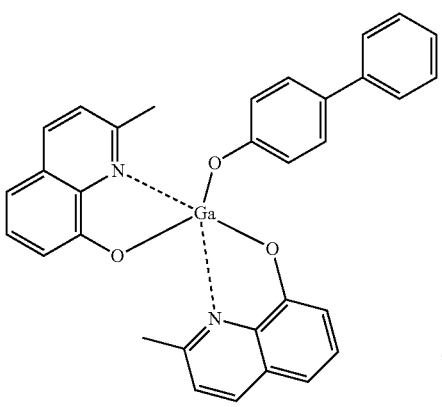
(E-4)

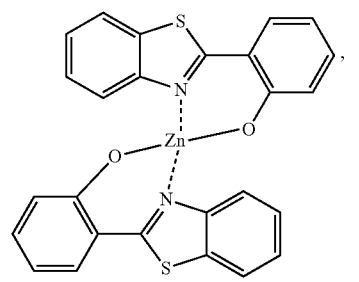
(E-5)

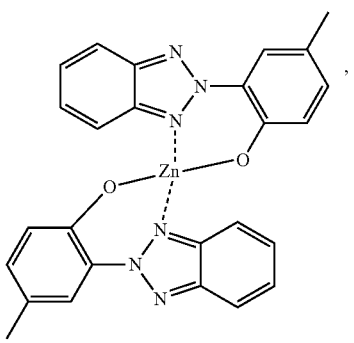
(E-6)

Application Example 6

On a cleaned glass substrate with an ITO electrode, 4,4',4''-tris(N-(3-methylphenyl)-N-phenylamino)triphenylamine is vacuum-deposited to form a first hole-injecting layer having a thickness of 25 nm. Further, a hole-injecting material (H-1) is vacuum-deposited to form a second hole-injecting layer having a thickness of 5 nm. Then, compounds A1, A2, A3, B1, B2, C1, G1 and H1, respectively, as light-emitting materials are vacuum-deposited to form a light-emitting layer having a thickness of 20 nm. Further, an electron-injecting material (E-1) is vacuum-deposited to form an electron-injecting layer having a thickness of 30 nm. Then, an electrode having a thickness of 150 nm is formed thereon from a magnesium/silver alloy having a magnesium/silver mixing ratio of 10/1, to obtain an organic EL device. The device shows emission having an outstanding brightness and efficiency at a direct current voltage of 5 V.

Application Example 7

On a cleaned glass substrate with an ITO electrode, 4,4',4''-tris(N-(1-naphthyl)-N-phenylamino)triphenylamine is vacuum-deposited to form a first hole-injecting layer having a thickness of 25 nm. Further, a hole-injecting material (H-2) is vacuum-deposited to form a second hole-injecting layer having a thickness of 5 nm. Then, compounds A1, A2, A3, B1, B2, C1, G1 and H1, respectively, as light-emitting materials are vacuum-deposited to form a light-emitting layer having a thickness of 20 nm. Further, an electron-injecting material (E-5) is vacuum-deposited to form an electron-injecting layer having a thickness of 30 nm. Then, an electrode having a thickness of 150 nm is formed thereon from a magnesium/silver alloy having a magnesium/silver mixing ratio of 10/1, to obtain an organic EL device. The device shows an emission having a outstanding brightness and efficiency at a direct current voltage of 5V.

Application Example 8

A hole-injecting material (H-5) is vacuum-deposited on a cleaned glass substrate with an ITO electrode to form a hole-injecting layer having a thickness of 20 nm. Then, compounds A1, A2, A3, B1, B2, C1, G1 and H1, respectively, as light-emitting materials are vacuum-deposited to form a light-emitting layer having a thickness of 20 nm. Further, an electron-injecting material (E-2) is vacuum-deposited to form a first electron-injecting layer having a thickness of 20 nm. Then, an electron-injecting material (E-5) is vacuum-deposited to form a second electron-injecting layer having a thickness of 10 nm, and an electrode having a thickness of 150 nm is formed thereon from a magnesium/silver alloy having an magnesium/silver mixing ratio of 10/1, to obtain an organic EL device. The device shows light emission having an excellent brightness and efficiency at a direct current voltage of 5 V.

Application Example 9

An organic EL device is prepared in the same manner as in Example 5 except that the light-emitting layer is replaced with a 30 nm thick light-emitting layer formed by vacuum-depositing compounds A1, A2, A3, B1, B2, C1, G1 and H1, respectively, and one of the dopant compounds (D-1) to (D-7) in a weight ratio of 100:1. All the organic EL devices obtained in these Examples shows high brightness characteristics and gives intended light emission colors.

(D-1)
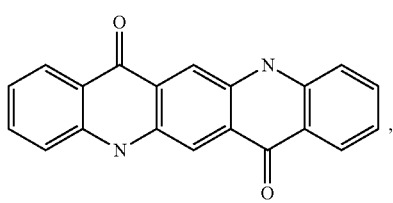

(D-2)
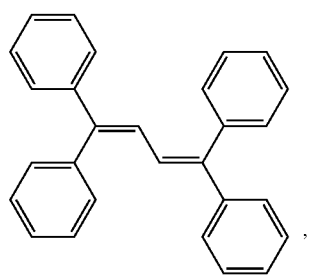

(D-3)
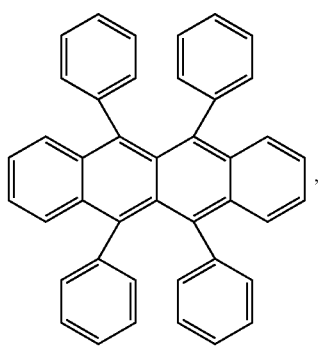

(D-4)
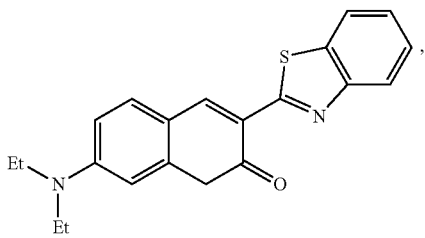

(D-5)
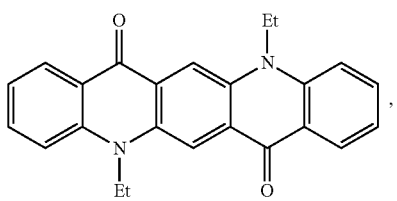

(D-6)
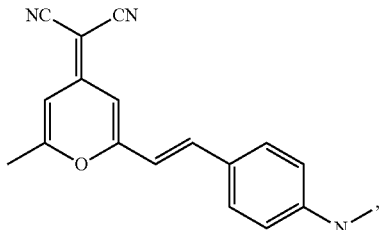

(D-7)
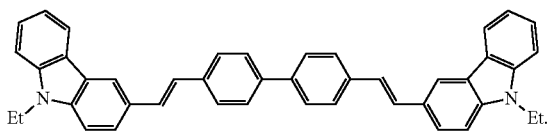

Application Example 10

An organic EL device is prepared in the same manner as in Example 5 except that the light-emitting layer is replaced with a 30 nm thick light-emitting layer formed by vacuum-depositing compounds A1, A2, A3, B1, B2, C1, G1 and H1, respectively and one of Compounds (D-1) to (D-7) in a weight ratio of 100:1. All the organic EL devices obtained in these Examples shows high brightness characteristics, or a maximum brightness and gives intended light emission colors.

Application Example 11

A hole-injecting material (H-2) is vacuum-deposited on a cleaned glass substrate with an ITO electrode to form a hole-injecting layer having a thickness of 30 nm. Then, 4,4'-bis(α,α-diphenylvinyl)biphenyl and a light-emitting material selected from compounds A1, A2, A3, B1, B2, C1, G1 and H1 for a light-emitting layer are vacuum-deposited in a weight ratio of 100:5 to form a light-emitting layer having a thickness of 30 nm. Further, an electron-injecting material (E-3) is vacuum-deposited to form an electron-injecting layer having a thickness of 30 nm. Then, an electrode having a thickness of 150 nm is formed thereon from a magnesium/silver alloy having an magnesium/silver mixing ratio of 10/1, to obtain an organic EL device. The device shows an emission having an outstanding brightness and efficiency at a direct current voltage of 5 V.

Application Example 12

An organic EL device is prepared in the same manner as in Example 11 except that the light-emitting layer is replaced with a 30 nm thick light-emitting layer formed by vacuum-depositing aluminum tris(8-hydroxyquinolinate) and one of the light-emitting materials A1, A2, A3, B1, B2, C1, G1 and H1 in a weight ratio of 100:3. All the organic EL devices obtained in these Examples shows high brightness characteristics at a direct current of 5 V.

The organic EL devices obtained in the Application Examples of the present invention show an excellent light emission brightness and achieved a high light emission efficiency. When the organic EL devices obtained in the above Examples are allowed to continuously emit light at 3 (mA/cm²), all the organic EL devices remain stable. Since the light-emitting materials of the present invention have a very high fluorescence quantum efficiency, the organic EL devices using the light-emitting materials achieved light emission with a high brightness in a low electric current applied region, and when the light-emitting layer additionally uses a doping material, the organic EL devices are improved in maximum light emission brightness and maximum light emission efficiency. Further, by adding a doping material having a different fluorescent color to the light-emitting material of the present invention, there are obtained light-emitting devices having a different light emission color. The organic EL devices of the present invention accomplish improvements in light emission efficiency and light emission brightness and a longer device life, and does not impose any limitations on a light-emitting material, a dopant, a hole-injecting material, an electron-injecting material, a sensitizer, a resin and an electrode material used in combination and the method of producing the device. The organic EL device using the material of the present invention as a light-emitting material achieves light emission having a high brightness with a high light emission efficiency and a longer life as compared with conventional devices. According to the light-emitting material of the present invention and the organic EL device of the present invention, there can be achieved an organic EL device having a high brightness, a high light emission efficiency and a long life.

The invention claimed is:
1. An electroluminescent device comprising a compound of formula (I)

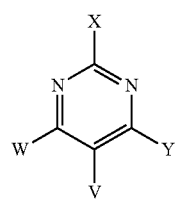

(I)

wherein
V is $C_2$-$C_{30}$ heteroaryl, which can be substituted or unsubstituted, $C_1$-$C_{18}$alkyl; $C_1$-$C_{18}$alkyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy;

$C_1$-$C_{18}$alkoxy which is optionally substituted by E and optionally interrupted by D; —$SR^5$; —$NR^5R^6$;

wherein when V is $C_1$-$C_{18}$alkyl or $C_1$-$C_{18}$alkyl which is optionally substituted by E and optionally interrupted by D, V does not join with W or Y to form a ring;

W is $C_6$-$C_{30}$aryl or $C_2$-$C_{30}$heteroaryl, which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D;

$C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; —$NR^5R^6$;

Y is $C_6$-$C_{30}$aryl or $C_2$-$C_{30}$heteroaryl, which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; —$NR^5R^6$;

X is $C_6$-$C_{30}$aryl or $C_2$-$C_{30}$heteroaryl, which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; —$NR^5R^6$; or one or more of the substituents V, W, X, or Y is a group of the formula —Z or —Ar—Z, wherein Ar is

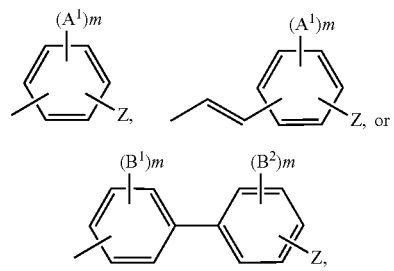

wherein Z is a group of formula

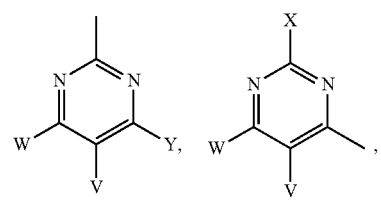

-continued

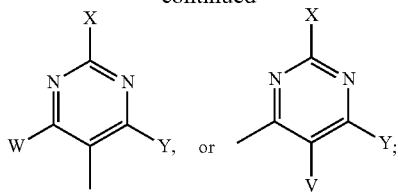

wherein
A¹, B¹ and B² are independently of each other H; $C_6$-$C_{18}$aryl; $C_6$-$C_{18}$aryl which is substituted by G; $C_1$-$C_{18}$alkyl; $C_1$-$C_{18}$alkyl which is optionally substituted by E and optionally interrupted by D; $C_7$-$C_{18}$alkylaryl; $C_7$-$C_{18}$alkylaryl which is optionally substituted by E and optionally interrupted by D; $C_2$-$C_{18}$alkenyl; $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy, $C_1$-$C_{18}$alkoxy which is optionally substituted by E and optionally interrupted by D; —$SR^5$; —$NR^5R^6$; $C_2$-$C_{18}$heteroaryl; $C_2$-$C_{18}$heteroaryl which is substituted by L; —$SOR^4$; —$SO_2R^4$; —$COR^8$; —$COOR^7$; —$CONR^5R^6$; $C_4$-$C_{18}$cycloalkyl; $C_4$-$C_{18}$cycloalkyl which is optionally substituted by E and optionally interrupted by D; $C_4$-$C_{18}$cycloalkenyl; $C_4$-$C_{18}$cycloalkenyl which is optionally substituted by E and optionally interrupted by D; wherein two substituents $A^1$, $B^1$, $B^2$ or $B^1$ and $B^2$ optionally form a five to seven membered ring, which is optionally substituted, m is an integer of 1 to 4;

D is —CO—; —COO—; —OCOO—; —S—; —SO—; —$SO_2$—; —O—; —$NR^5$—; —$SiR^5R^6$—; —$COR^8$—; —$CR^5$=$CR^6$—; or —C≡C—;

E is —$OR^5$; —$SR^5$; —$NR^5R^6$; —$COR^8$; —$COOR^7$; —$CONR^5R^6$; —CN; —$OCOOR^7$; or halogen;

G is E; K; heteroaryl; heteroaryl which is substituted by $C_6$-$C_{18}$aryl; $C_6$-$C_{18}$aryl which is substituted by E and/or K;

K is $C_1$-$C_{18}$alkyl; $C_1$-$C_{18}$alkyl which is optionally substituted by E and optionally interrupted by D; $C_7$-$C_{18}$alkylaryl which is optionally substituted by E and optionally interrupted by D; $C_2$-$C_{18}$alkenyl; $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy, $C_1$-$C_{18}$alkoxy which is optionally substituted by E and optionally interrupted by D; $C_4$-$C_{18}$cycloalkyl; $C_4$-$C_{18}$cycloalkyl which is optionally substituted by E and optionally interrupted by D; $C_4$-$C_{18}$cycloalkenyl; or $C_4$-$C_{18}$cycloalkenyl which is optionally substituted by E and optionally interrupted by D;

L is E; K; $C_6$-$C_{18}$aryl; or $C_6$-$C_{18}$aryl which is substituted by G, E and/or K;

$R^4$ is $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^5$ and $R^6$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; wherein $R^5$ and $R^6$ optionally together form a five or six membered ring $R^7$ is H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; $C_1$-$C_{18}$alkyl which is interrupted by —O—;

$R^8$ is H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; $C_1$-$C_{18}$alkyl which is interrupted by —O—;

with the proviso that at least one of the groups V, W, X and Y is a $C_6$-$C_{24}$aryl, or $C_2$-$C_{24}$heteroaryl group, which is optionally substituted.

2. The electroluminescent device of claim 1, wherein W, X, and Y are each $C_6$-$C_{30}$aryl or $C_2$-$C_{30}$heteroaryl;

at least one of the groups W, X, and Y is represented by

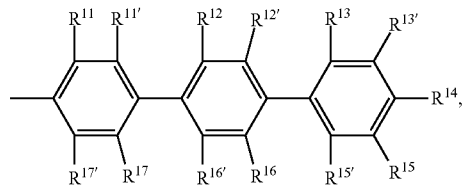

wherein $R^{11}$, $R^{11'}$, $R^{12}$, $R^{12'}$, $R^{13}$, $R^{13'}$, $R^{15}$, $R^{15'}$, $R^{16}$, $R^{16'}$, $R^{17}$, and $R^{17'}$ are independently of each other H, E, $C_6$-$C_{18}$aryl; $C_6$-$C_{18}$aryl which is substituted by E; $C_1$-$C_{18}$alkyl; $C_1$-$C_{18}$alkyl which is optionally substituted by E and optionally interrupted by D; $C_7$-$C_{18}$aralkyl; or $C_7$-$C_{18}$aralkyl which is substituted by E;

the substituent pairs $R^{11'}$ and $R^{12}$, $R^{12'}$ and $R^{13}$, $R^{15'}$ and $R^{16}$, and $R^{16'}$ and $R^{17}$ are each optionally a divalent group selected from an oxygen atom, an sulfur atom, >$CR^{118}R^{119}$, >$SiR^{118}R^{119}$, and

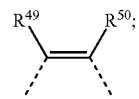

wherein $R^{118}$ and $R^{119}$ are independently of each other $C_1$-$C_{18}$alkyl; $C_1$-$C_{18}$alkoxy, $C_6$-$C_{18}$aryl; $C_7$-$C_{18}$aralkyl; $R^{49}$ and $R^{50}$ are independently of each other H, $C_1$-$C_{18}$alkyl; $C_1$-$C_{18}$alkyl, which is optionally substituted by E and optionally interrupted by D; E; $C_6$-$C_{18}$aryl; $C_6$-$C_{18}$aryl, which is substituted by E; and the substituent pairs $R^{11}$ and $R^{11'}$, $R^{12}$ and $R^{12'}$, $R^{13}$ and $R^{13'}$, $R^{13'}$ and $R^{14}$, $R^{14}$ and $R^{15}$ $R^{15}$ and $R^{15'}$, $R^{16}$ and $R^{16'}$, and $R^{17'}$ and $R^{17}$, are each optionally the divalent group

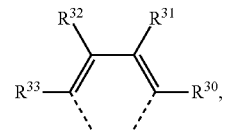

wherein $R^{30}$, $R^{31}$, $R^{32}$, and $R^{33}$ are independently of each other H, $C_1$-$C_{18}$alkyl; $C_1$-$C_{18}$alkyl, which is optionally substituted by E and optionally interrupted by D; E; $C_6$-$C_{18}$aryl; $C_6$-$C_{18}$aryl, which is substituted by E;

$R^{14}$ is H, $C_2$-$C_{30}$heteroaryl, $C_6$-$C_{30}$aryl, or $C_6$-$C_{30}$aryl which is substituted by E, $C_1$-$C_{18}$alkyl; or $C_1$-$C_{18}$alkyl which is optionally substituted by E and optionally interrupted by D;

D is —CO—; —COO—; —OCOO—; —S—; —SO—; —SO$_2$—; —O—; —NR$^5$—; SiR$^5$R$^6$—; —POR$^5$—; —CR$^9$═CR$^{10}$—; or —C≡C—;

E is —OR$^5$; —SR$^5$; —NR$^5$R$^6$; —COR$^8$; —COOR$^7$; —CONR$^5$R$^6$; —CN; or halogen, especially F, or Cl; wherein R$^5$ and R$^6$ are independently of each other C$_6$-C$_{18}$aryl; C$_6$-C$_{18}$aryl which is substituted by C$_1$-C$_{18}$alkyl, C$_1$-C$_{18}$alkyl; or C$_1$-C$_{18}$alkyl which is interrupted by —O—; wherein R$^5$ and R$^6$ together optionally form a five or six membered ring, R$^7$ is C$_6$-C$_{18}$aryl; C$_6$-C$_{18}$aryl which is substituted by C$_1$-C$_{18}$alkyl, C$_1$-C$_{18}$alkyl; or C$_1$-C$_{18}$alkyl which is interrupted by —O—;

R$^8$ is C$_7$-C$_{12}$alkylaryl; C$_1$-C$_{18}$alkyl; or C$_1$-C$_{18}$alkyl which is interrupted by —O—; and R$^9$ and R$^{10}$ are independently of each other H, C$_6$-C$_{18}$aryl; C$_6$-C$_{18}$aryl which is substituted by C$_1$-C$_{18}$alkyl, C$_1$-C$_{18}$alkyl; or C$_1$-C$_{18}$alkyl which is interrupted by —O—.

3. The electroluminescent device of claim 1, wherein W and Y are independently

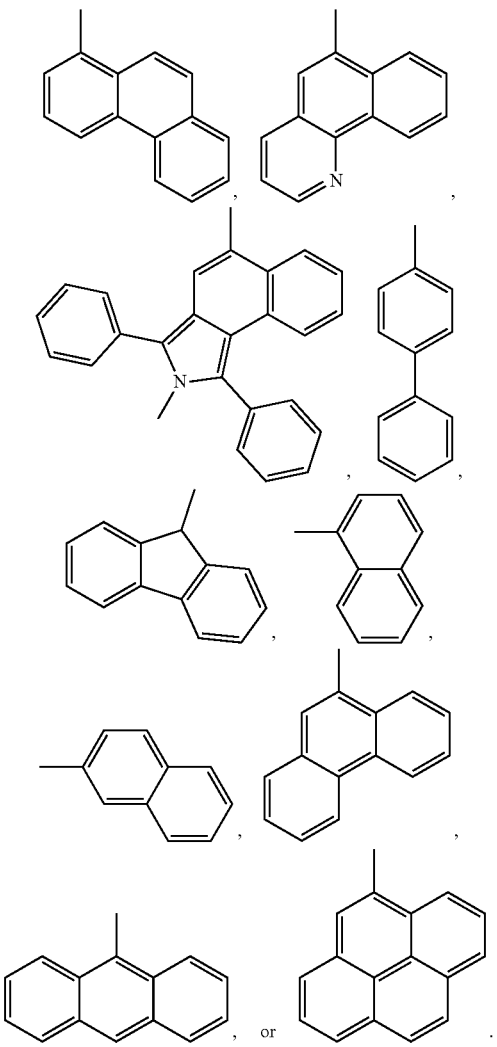

4. The electroluminescent device of claim 1, wherein W and Y are independently

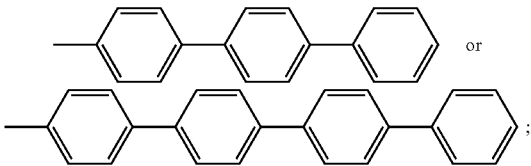

and X is

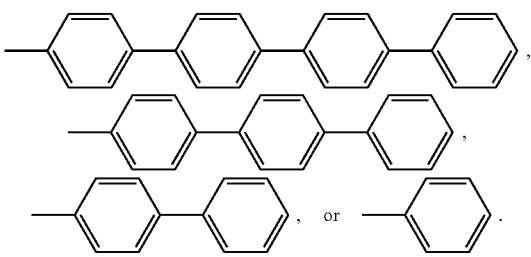

5. The electroluminescent device of claim 1, wherein

V is, C$_2$-C$_{30}$heteroaryl, C$_1$-C$_{18}$alkyl; C$_1$-C$_{18}$alkyl which is optionally substituted by E and optionally interrupted by D; C$_2$-C$_{18}$alkynyl; C$_2$-C$_{18}$alkynyl which is optionally substituted by E and optionally interrupted by D; C$_1$-C$_{18}$alkoxy; C$_1$-C$_{18}$alkoxy which is optionally substituted by E and optionally interrupted by D; —SR$^5$; or —NR$^5$R$^6$;

X is

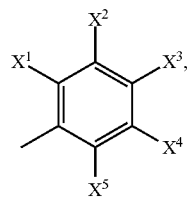

C$_2$-C$_{30}$heteroaryl, H, C$_2$-C$_{30}$heteroaryl, C$_1$-C$_{18}$alkyl; C$_1$-C$_{18}$alkyl which is optionally substituted by E and optionally interrupted by D; C$_2$-C$_{18}$alkenyl, C$_2$-C$_{18}$alkenyl which is optionally substituted by E and optionally interrupted by D; C$_2$-C$_{18}$alkynyl; C$_2$-C$_{18}$alkynyl which is optionally substituted by E and optionally interrupted by D; C$_1$-C$_{18}$alkoxy; C$_1$-C$_{18}$alkoxy which is optionally substituted by E and optionally interrupted by D; —SR$^5$; or —NR$^5$R$^6$ W is

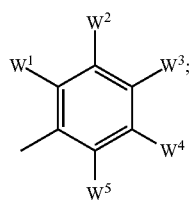

Y is

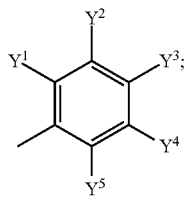

$C_2$-$C_{30}$heteroaryl, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; or —$NR^5R^6$;
  wherein the groups $W^1$ to $W^5$, $X^1$ to $X^5$ and $Y^1$ to $Y^5$ are each independently H; halogen, $C_6$-$C_{24}$aryl; $C_6$-$C_{24}$aryl which is substituted by G; $C_1$-$C_{18}$alkyl; $C_1$-$C_{18}$alkyl which is optionally substituted by E and optionally interrupted by D; $C_7$-$C_{18}$alkylaryl; $C_7$-$C_{18}$alkylaryl which is optionally substituted by E and optionally interrupted by D; $C_2$-$C_{18}$alkenyl; $C_2$-$C_{18}$alkenyl which is optionally substituted by E and optionally interrupted by D;

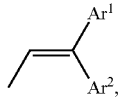

wherein $Ar^1$ is $C_6$-$C_{30}$aryl or $C_2$-$C_{30}$heteroaryl, especially phenyl, $Ar^2$ is $C_6$-$C_{30}$aryl or $C_2$-$C_{30}$heteroaryl, especially phenyl, or H, $C_2$-$C_{18}$alkynyl; $C_2$-$C_{18}$alkynyl which is optionally substituted by E and optionally interrupted by D; $C_1$-$C_{18}$alkoxy, $C_1$-$C_{18}$alkoxy which is optionally substituted by E and optionally interrupted by D; —$SR^5$; —$NR^5R^6$; $C_2$-$C_{24}$heteroaryl; $C_2$-$C_{24}$heteroaryl which is substituted by L; —$SOR^4$; —$SO_2R^4$; —$COR^8$; —$COOR^7$; —$CONR^5R^6$; $C_4$-$C_{18}$cycloalkyl; $C_4$-$C_{18}$cycloalkyl which is optionally substituted by E and optionally interrupted by D; $C_4$-$C_{18}$cycloalkenyl; $C_4$-$C_{18}$cycloalkenyl which is optionally substituted by E and optionally interrupted by D; or
  $W^5$ or $Y^5$ together with V form a group —$CR^9_2$—, —$CR^9_2$—$CR^9_2$—, —C(=O)$CR^9_2$—, —C(=O)—, or —$CR^9$=$CR^9$—, or
  $W^5$ and $Y^5$ together with V form a group

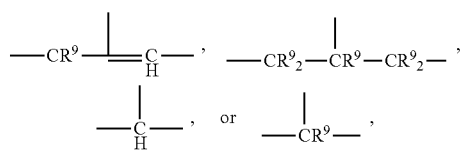

wherein $R^9$ is H; $C_1$-$C_{18}$alkyl, $C_1$-$C_{18}$alkyl which is interrupted by —O—, $C_6$-$C_{18}$aryl, $C_6$-$C_{18}$aryl which is substituted by $C_1$-$C_{18}$alkyl, or $C_1$-$C_{18}$alkoxy, or
one or more of the substituents $W^1$ to $W^5$, $X^1$ to $X^5$, or $Y^1$ to $Y^5$ is a group of the formula —Z' or —Ar—Z', wherein Ar is

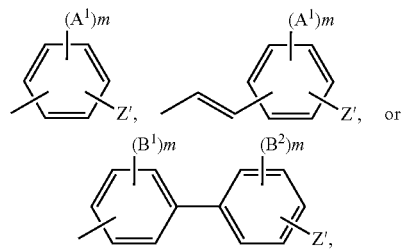

wherein Z' is a group of formula

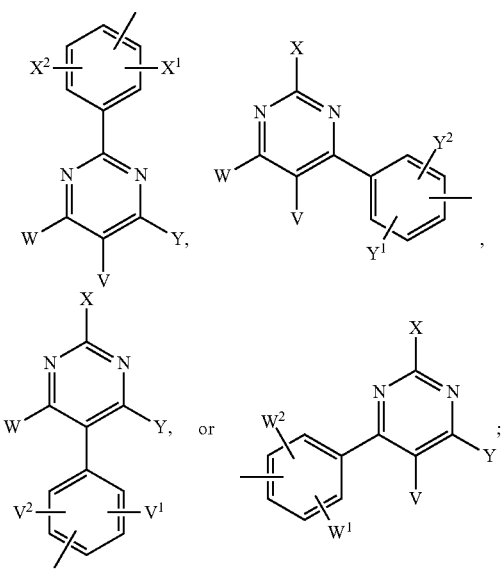

wherein two adjacent substituents $W^1$ to $W^5$, $X^1$ to $X^5$, or $Y^1$ to $Y^5$ optionally join to form a five to seven membered ring.

6. The electroluminescent device of claim 5, wherein W is

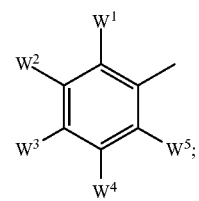

X is

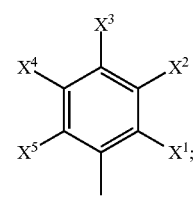

and
Y is

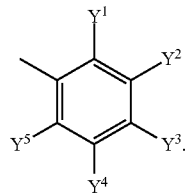

7. The electroluminescent device of claim 5, wherein the compound is represented by formula (IV)

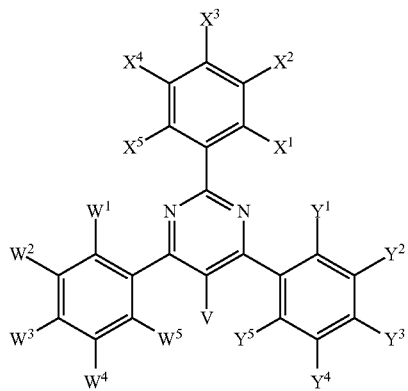

(IV)

wherein

V is $C_1$-$C_{18}$ alkyl;

$W^1$, $W^5$, $Y^1$, $Y^5$, $X^1$, and $X^5$ are independently of each other H; $C_1$-$C_{18}$alkyl; or $C_1$-$C_{18}$alkyl which is optionally substituted by E and optionally interrupted by D; and $W^3$, $X^3$ and $Y^3$ are selected from the group consisting of $C_6$-$C_{24}$aryl, $C_6$-$C_{24}$aryl which is substituted by G, $C_2$-$C_{24}$heteroaryl, $C_2$-$C_{24}$heteroaryl which is substituted by L, $C_1$-$C_{18}$alkoxy, —$SR^5$, and —$NR^5R^6$.

8. The electroluminescent device of claim 5, wherein the compound is represented by formula (Xa) or (Xb)

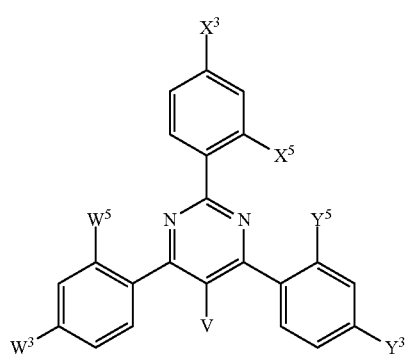

(Xa)

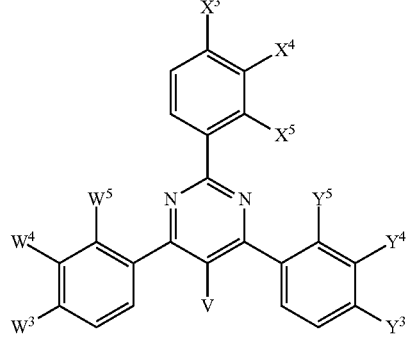

(Xb)

wherein V is $C_1$-$C_8$alkyl;

$X^3$ and $X^4$ are independently of each other H, $C_1$-$C_8$alkyl, $C_1$-$C_8$alkoxy, $C_1$-$C_8$thioalkyl, or phenyl, $X^5$ is H or $C_1$-$C_8$alkoxy;

$W^5$ is H, $C_1$-$C_8$alkyl, or $O(CH_2)_{n1}$—X;

$Y^5$ is H, $C_1$-$C_8$alkyl, or $O(CH_2)_{n1}$—X;

$Y^3$, $Y^4$, $W^3$, and $W^4$ are independently of each other $C_1$-$C_8$alkyl; $C_1$-$C_8$alkoxy; $C_1$-$C_8$thioalkyl; halogen; phenyl; or $O(CH_2)_{n1}$—X;

each occurrence of n1 is independently an integer of 1 to 5;

each X is independently —O—$(CH_2)_{m1}CH_3$, —OC(O)—$(CH_2)_{m1}CH_3$, —C(O)—O—$C_1$-$C_8$alkyl, or —$NR^{103}R^{104}$;

wherein m1 is an integer of 0 to 5; and $R^{103}$ and $R^{104}$ are independently of each other H or $C_1$-$C_8$-alkyl, wherein $R^{103}$ and $R^{104}$ together optionally form a five or six membered heterocyclic ring.

9. The electroluminescent device of claim 5, wherein the compound is represented by formula (XI)

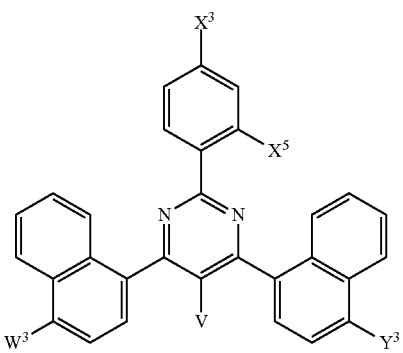

(XI)

wherein V is $C_1$-$C_8$alkyl;

$W^3$ is H, $C_1$-$C_8$alkyl, or $C_1$-$C_8$alkoxy;

$X^3$ is H, $C_1$-$C_8$alkoxy, phenyl or $O(CH_2)_{n1}$—X;

$X^5$ is H, $C_1$-$C_8$alkoxy, phenyl or $O(CH_2)_{n1}$—X;

$Y^3$ is H, $C_1$-$C_8$alkyl, or $C_1$-$C_8$alkoxy;

each occurrence of n1 is independently an integer of 1 to 5;

each X is independently —O—$(CH_2)_{m1}CH_3$, —OC(O)—$(CH_2)_{m1}CH_3$, —C(O)—O—$C_1$-$C_8$alkyl, or —$NR^{103}R^{104}$;

wherein m1 is an integer of 0 to 5; and $R^{103}$ and $R^{104}$ are independently of each other H or $C_1$-$C_8$-alkyl, wherein $R^{103}$ and $R^{104}$ together optionally form a five or six membered heterocyclic ring.

10. The electroluminescent device of claim 5, wherein the compound is represented by formula (XIVd):

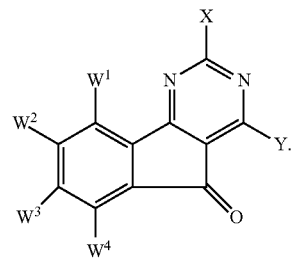

11. The electroluminescent device of claim 5, wherein the compound is represented by one of compound A-25 to A-49:

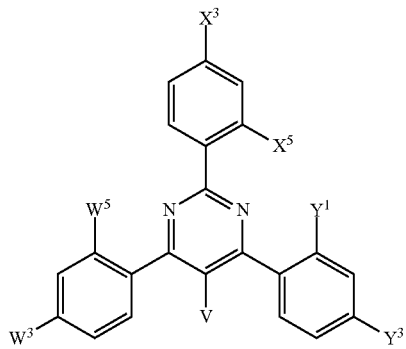

| Cpd. | $X^3$ | $Y^3$ | $W^3$ | $X^5$ | $Y^1$ | $W^5$ | V |
|---|---|---|---|---|---|---|---|
| A-25 | Ph | Ph | Ph | H | H | H | $CH_3$ |
| A-26 | OMe | OMe | OMe | H | H | H | $CH_3$ |
| A-27 | H | Ph | Ph | H | H | H | $CH_3$ |
| A-28 | H | OMe | OMe | H | H | H | $CH_3$ |
| A-29 | H | OMe | OMe | H | OMe | OMe | $CH_3$ |
| A-30 | H | OBu | OBu | H | H | H | $CH_3$ |
| A-31 | H | OBu | OBu | H | OBu | OBu | $CH_3$ |
| A-32 | OMe | OMe | OMe | OMe | OMe | OMe | $CH_3$ |
| A-33 | OMe | Br | Br | OMe | H | H | $CH_3$ |
| A-34 | Ph | Br | Br | H | H | H | $CH_3$ |
| A-35 | OMe | Ph | Ph | OMe | H | H | $CH_3$ |
| A-36 | H | $OCH_2COOMe$ | $OCH_2COOMe$ | H | $OCH_2COOMe$ | $OCH_2COOMe$ | $CH_3$ |
| A-37 | SMe | SMe | SMe | H | H | H | $CH_3$ |
| A-38 | H | SMe | SMe | H | H | H | $CH_3$ |
| A-39 | H | $OCH_2CH_2OAc$ | $OCH_2CH_2OAc$ | H | H | H | $CH_3$ |
| A-40 | H | $OCH_2CH_2OAc$ | $OCH_2CH_2OAc$ | H | $OCH_2CH_2OAc$ | $OCH_2CH_2OAc$ | $CH_3$ |
| A-41 | H | $OCH_2CH_2OCH_2Et$ | $OCH_2CH_2OCH_2Et$ | H | H | H | $CH_3$ |
| A-42 | H | $OCH_2CH_2OCH_2Et$ | $OCH_2CH_2OCH_2Et$ | H | $OCH_2CH_2OCH_2Et$ | $OCH_2CH_2OCH_2Et$ | $CH_3$ |
| A-43 | OBu | Ph | Ph | OBu | H | H | $CH_3$ |
| A-44 | H | $N(CH_3)_2$ | $N(CH_3)_2$ | H | H | H | $CH_3$ |
| A-45 | H | —N⟨pyrrolidine⟩ | —N⟨pyrrolidine⟩ | H | H | H | $CH_3$ |
| A-46 | Ph | $N(CH_3)_2$ | $N(CH_3)_2$ | H | H | H | $CH_3$ |
| A-47 | Ph | —N⟨pyrrolidine⟩ | —N⟨pyrrolidine⟩ | H | H | H | $CH_3$ |
| A-48 | Ph | $CH_3$ | $CH_3$ | H | H | H | $CH_3$ |
| A-49 | Ph | $CH_3$ | $CH_3$ | H | H | H | $CH_3$ |

12. The electroluminescent device of claim 5, wherein the compound is represented by one of compound B-13 to B-22:

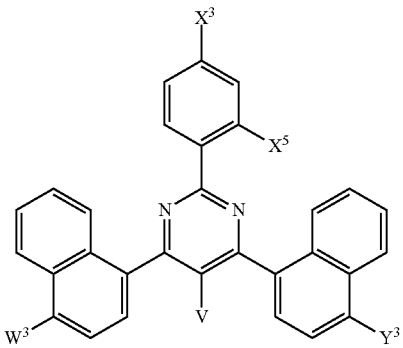

| Cpd. | X³ | Y³ | W³ | X⁵ | V |
|---|---|---|---|---|---|
| B-13 | Ph | H | H | H | CH₃ |
| B-14 | OMe | H | H | OMe | CH₃ |
| B-15 | OBu | H | H | OBu | CH₃ |
| B-16 | H | H | H | H | CH₃ |
| B-17 | OCH₂COOMe | H | H | OCH₂COOMe | CH₃ |
| B-18 | H | OMe | OMe | H | CH₃ |
| B-19 | OCH₂CH₂OCH₂Et | H | H | OCH₂CH₂OCH₂Et | CH₃ |
| B-20 | OCH₂CH₂OAc | H | H | OCH₂CH₂OAc | CH₃ |
| B-21 | H | CH₃ | CH₃ | H | CH₃ |
| B-22 | Ph | CH₃ | CH₃ | H | CH₃. |

13. The electroluminescent device of claim 1, wherein the compound is represented by formula (III)

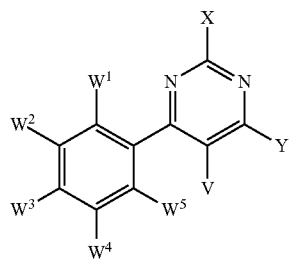

(III)

wherein

X and Y are each independently selected from the group consisting of $C_6$-$C_{30}$aryl or $C_2$-$C_{30}$heteroaryl which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; and —$NR^5R^6$; if X is

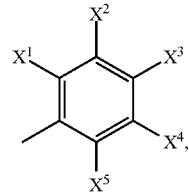

then Y is $R^1$, or
if Y is

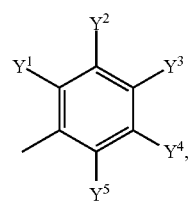

then X is $R^1$;

$R^1$ is H; $C_1$-$C_{18}$alkyl; $C_1$-$C_{18}$alkyl which is optionally substituted by E and optionally interrupted by D; $C_2$-$C_8$alkenyl; $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; or —$NR^5R^6$;

V is $C_2$-$C_{30}$heteroaryl, which can be substituted or unsubstituted; $C_1$-$C_{18}$alkyl; $C_1$-$C_{18}$alkyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; or —$NR^5R^6$;

$W^1$ to $W^5$, $X^1$ to $X^5$ and $Y^1$ to $Y^5$ are independently of each other H; $C_6$-$C_{24}$aryl; $C_6$-$C_{24}$aryl which is substituted by G; $C_1$-$C_{18}$alkyl; $C_1$-$C_{18}$alkyl which is optionally substituted by E and optionally interrupted by D; $C_7$-$C_{18}$alkylaryl; $C_7$-$C_{18}$alkylaryl which is optionally substituted by E and optionally interrupted by D; $C_2$-$C_{18}$alkenyl; $C_2$-$C_{18}$alkenyl which is optionally substituted by E and optionally interrupted by D;

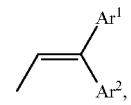

wherein $Ar^1$ is $C_6$-$C_{30}$aryl or $C_2$-$C_{30}$heteroaryl and $Ar^2$ is $C_6$-$C_{30}$aryl or $C_2$-$C_{30}$heteroaryl; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —$SR^5$; —$NR^5R^6$; $C_2$-$C_{24}$heteroaryl; $C_2$-$C_{24}$heteroaryl which is substituted by L; —$SOR^4$; —$SO_2R^4$; —$COR^8$; —$COOR^7$; —$CONR^5R^6$; $C_4$-$C_{18}$cycloalkyl; $C_4$-$C_{18}$cycloalkyl which is optionally substituted by E and optionally interrupted by D;

$C_4$-$C_{18}$cycloalkenyl; or $C_4$-$C_{18}$cycloalkenyl which is optionally substituted by E and optionally interrupted by D;

wherein two adjacent substituents selected from V, $W^1$ to $W^5$, $X^1$ to $X^5$, and $Y^1$ to $Y^5$ optionally join to form a five to seven membered ring;

D is —CO—; —COO—; —OCOO—; —S—; —SO—; —SO$_2$—; —O—; —NR$^5$—; —SiR$^5$R$^6$—; —POR$^5$—; —CR$^5$=CR$^6$— or —C≡C—;

E is —OR$^5$; —SR$^5$; —NR$^5$R$^6$; —COR$^8$; —COOK'; —CONR$^5$R$^6$; —CN; —OCOOR$^7$ or halogen;

G is E; K; heteroaryl; heteroaryl which is substituted by $C_6$-$C_{18}$aryl; $C_6$-$C_{18}$aryl which is substituted by E or K;

K is $C_1$-$C_{18}$alkyl; $C_1$-$C_{18}$alkyl which is optionally substituted by E and optionally interrupted by D; $C_7$-$C_{18}$alkylaryl which is optionally substituted by E and optionally interrupted by D; $C_2$-$C_{18}$alkenyl; $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy, $C_1$-$C_{18}$alkoxy which is optionally substituted by E and optionally interrupted by D; $C_4$-$C_{18}$cycloalkyl; $C_4$-$C_{18}$cycloalkyl which is optionally substituted by E and optionally interrupted by D; $C_4$-$C_{18}$cycloalkenyl; or $C_4$-$C_{18}$cycloalkenyl which is optionally substituted by E and optionally interrupted by D;

L is E; K; $C_6$-$C_{18}$aryl or $C_6$-$C_{18}$aryl which is substituted by G, E or K;

$R^4$ is $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;

$R^5$ and $R^6$ are independently of each other H; $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—; or $R^5$ and $R^6$ together form a five or six membered ring;

$R^7$ is H; $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; $C_1$-$C_{18}$alkyl which is interrupted by —O—;

$R^8$ is H; $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; $C_1$-$C_{18}$alkyl which is interrupted by —O—.

14. A compound of formula (I)

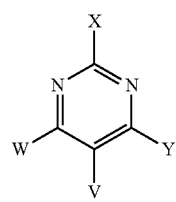

(I)

wherein

V is $C_2$-$C_{30}$heteroaryl, which can be substituted or unsubstituted, $C_1$-$C_{18}$alkyl; $C_1$-$C_{18}$alkyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —SR$^5$; —NR$^5$R$^6$;

wherein when V is $C_1$-$C_{18}$alkyl or $C_1$-$C_{18}$alkyl which is optionally substituted by E and optionally interrupted by D, V does not join with W or Y to form a ring;

W is $C_6$-$C_{30}$aryl or $C_2$-$C_{30}$heteroaryl, which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —SR$^5$; —NR$^5$R$^6$;

Y is $C_6$-$C_{30}$aryl or $C_2$-$C_{30}$heteroaryl, which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D;

$C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —SR$^5$; —NR$^5$R$^6$;

X is $C_6$-$C_{30}$aryl or $C_2$-$C_{30}$heteroaryl, which can be substituted or unsubstituted, H, $C_1$-$C_{18}$alkyl; $C_1$-$C_{18}$alkyl which is optionally substituted by E and optionally interrupted by D; $C_2$-$C_{18}$alkenyl, $C_2$-$C_{18}$alkenyl which is optionally substituted by E and optionally interrupted by D; $C_2$-$C_{18}$alkynyl; $C_2$-$C_{18}$alkynyl which is optionally substituted by E and optionally interrupted by D; $C_1$-$C_{18}$alkoxy; $C_1$-$C_{18}$alkoxy which is optionally substituted by E and optionally interrupted by D; —SR$^5$; —NR$^5$R$^6$; or one or more of the substituents V, W, X, or Y is a group of the formula —Z or —Ar—Z, wherein Ar is

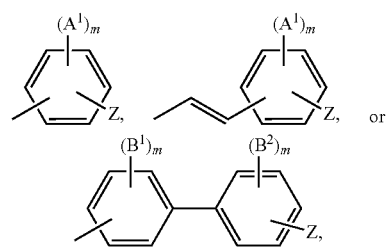

wherein Z is a group of formula

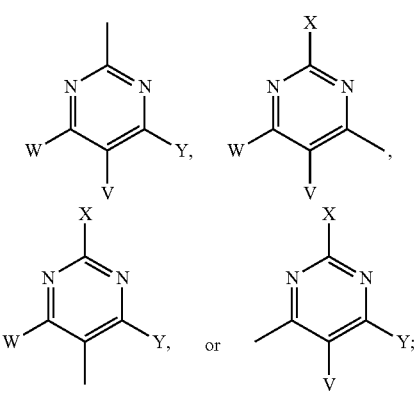

wherein
A$^1$, B$^1$ and B$^2$ are independently of each other H; C$_6$-C$_{18}$aryl; C$_6$-C$_{18}$aryl which is substituted by G; C$_1$-C$_{18}$alkyl; C$_1$-C$_{18}$alkyl which is optionally substituted by E and optionally interrupted by D; C$_7$-C$_{18}$alkylaryl; C$_7$-C$_{18}$alkylaryl which is optionally substituted by E and optionally interrupted by D; C$_2$-C$_{18}$alkenyl; C$_2$-C$_{18}$alkenyl which is optionally substituted by E and optionally interrupted by D; C$_2$-C$_{18}$alkynyl; C$_2$-C$_{18}$alkynyl which is optionally substituted by E and optionally interrupted by D; C$_1$-C$_{18}$alkoxy, C$_1$-C$_{18}$alkoxy which is optionally substituted by E and optionally interrupted by D; —SR$^5$; —NR$^5$R$^6$; C$_2$-C$_{18}$heteroaryl; C$_2$-C$_{18}$heteroaryl which is substituted by L; —SOR$^4$; —SO$_2$R$^4$; —COR$^8$; —COOR$^7$; —CONR$^5$R$^6$; C$_4$-C$_{18}$cycloalkyl; C$_4$-C$_{18}$cycloalkyl which is optionally substituted by E and optionally interrupted by D; C$_4$-C$_{18}$cycloalkenyl; C$_4$-C$_{18}$cycloalkenyl which is optionally substituted by E and optionally interrupted by D; wherein two substituents A$^1$, B$^1$, B$^2$ or B$^1$ and B$^2$ optionally form a five to seven membered ring, which is optionally substituted, m is an integer of 1 to 4;

D is —CO—; —COO—; —OCOO—; —S—; —SO—; —SO$_2$—; —O—; —NR$^5$—; —SiR$^5$R$^6$—; —POR$^5$—; —CR$^5$=CR$^6$— or —C≡C—;

E is —OR$^5$; —SR$^5$; —NR$^5$R$^6$; —COR$^8$; —COOR$^7$; —CONR$^5$R$^6$; —CN; —OCOOR$^7$; or halogen;

G is E; K; heteroaryl; heteroaryl which is substituted by C$_6$-C$_{18}$aryl; C$_6$-C$_{18}$aryl which is substituted by E and/or K;

K is C$_1$-C$_{18}$alkyl; C$_1$-C$_{18}$alkyl which is optionally substituted by E and optionally interrupted by D; C$_7$-C$_{18}$alkylaryl which is optionally substituted by E and optionally interrupted by D; C$_2$-C$_{18}$alkenyl; C$_2$-C$_{18}$alkenyl which is optionally substituted by E and optionally interrupted by D; C$_2$-C$_{18}$alkynyl; C$_2$-C$_{18}$alkynyl which is optionally substituted by E and optionally interrupted by D; C$_1$-C$_{18}$alkoxy, C$_1$-C$_{18}$alkoxy which is optionally substituted by E and optionally interrupted by D; C$_4$-C$_{18}$cycloalkyl; C$_4$-C$_{18}$cycloalkyl which is optionally substituted by E and optionally interrupted by D; C$_4$-C$_{18}$cycloalkenyl; or C$_4$-C$_{18}$cycloalkenyl which is optionally substituted by E and optionally interrupted by D;

L is E; K; C$_6$-C$_{18}$aryl; or C$_6$-C$_{18}$aryl which is substituted by G, E and/or K;

R$^4$ is C$_6$-C$_{18}$aryl; C$_6$-C$_{18}$aryl which is substituted by C$_1$-C$_{18}$alkyl, C$_1$-C$_{18}$alkoxy; C$_1$-C$_{18}$alkyl; or C$_1$-C$_{18}$alkyl which is interrupted by —O—;

R$^5$ and R$^6$ are independently of each other H; C$_6$-C$_{18}$aryl; C$_6$-C$_{18}$aryl which is substituted by C$_1$-C$_{18}$alkyl, C$_1$-C$_{18}$alkoxy; C$_1$-C$_{18}$alkyl; or C$_1$-C$_{18}$alkyl which is interrupted by —O—; wherein R$^5$ and R$^6$ optionally together form a five or six membered ring R$^7$ is H; C$_6$-C$_{18}$aryl; C$_6$-C$_{18}$aryl which is substituted by C$_1$-C$_{18}$alkyl, C$_1$-C$_{18}$alkoxy; C$_1$-C$_{18}$alkyl; C$_1$-C$_{18}$alkyl which is interrupted by —O—;

R$^8$ is H; C$_6$-C$_{18}$aryl; C$_6$-C$_{18}$aryl which is substituted by C$_1$-C$_{18}$alkyl, C$_1$-C$_{18}$alkoxy; C$_1$-C$_{18}$alkyl; C$_1$-C$_{18}$alkyl which is interrupted by —O—;

with the proviso that at least one of the groups V, W, X and Y is a C$_6$-C$_{24}$aryl, or C$_2$-C$_{24}$heteroaryl group, which is optionally substituted; and wherein at least one of the following conditions (i)-(iii) is true:
(i) W, X, and Y are each C$_6$-C$_{30}$aryl or C$_2$-C$_{30}$heteroaryl; at least one of the groups W, X, and Y is represented by

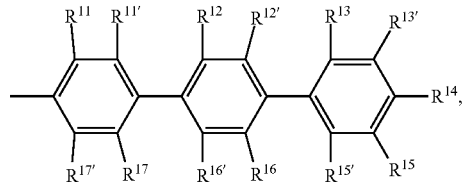

wherein R$^{11}$, R$^{11'}$, R$^{12}$, R$^{12'}$, R$^{13}$, R$^{13'}$, R$^{15}$, R$^{15'}$, R$^{16}$, R$^{16'}$, R$^{17}$, and R$^{17'}$ are independently of each other H, E, C$_6$-C$_{18}$aryl; C$_6$-C$_{18}$aryl which is substituted by E; C$_1$-C$_{18}$alkyl; C$_1$-C$_{18}$alkyl which is optionally substituted by E and optionally interrupted by D; C$_7$-C$_{18}$aralkyl; or C$_7$-C$_{18}$aralkyl which is substituted by E;

the substituent pairs R$^{11'}$ and R$^{12}$, R$^{12'}$ and R$^{13}$, R$^{15'}$ and R$^{16}$, and R$^{16'}$ and R$^{17}$ are each optionally a divalent group selected from an oxygen atom, an sulfur atom, >CR$^{118}$R$^{119}$, >SiR$^{118}$R$^{119}$, an

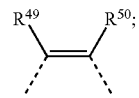

wherein R$^{118}$ and R$^{119}$ are independently of each other C$_1$-C$_{18}$alkyl; C$_1$-C$_{18}$alkoxy, C$_6$-C$_{18}$aryl; C$_7$-C$_{18}$aralkyl; R$^{49}$ and R$^{50}$ are independently of each other H, C$_1$-C$_{18}$alkyl; C$_1$-C$_{18}$alkyl, which is optionally substituted by E and optionally interrupted by D; E; C$_6$-C$_{18}$aryl; C$_6$-C$_{18}$aryl, which is substituted by E; and
the substituent pairs R$^{11}$ and R$^{11'}$, R$^{12}$ and R$^{12'}$, R$^{13}$ and R$^{13'}$, R$^{13'}$ and R$^{14}$, R$^{14}$ and R$^{15}$, R$^{15}$ and R$^{15'}$, R$^{16}$ and R$^{16'}$, and R$^{17'}$ and R$^{17}$, are each optionally the divalent group

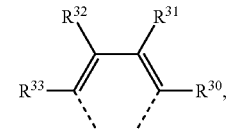

wherein R$^{30}$, R$^{31}$, R$^{32}$, and R$^{33}$ are independently of each other H, C$_1$-C$_{18}$alkyl; C$_1$-C$_{18}$alkyl, which is optionally substituted by E and optionally interrupted by D; E; C$_6$-C$_{18}$aryl; C$_6$-C$_{18}$aryl, which is substituted by E;
R$^{14}$ is H, C$_2$-C$_{30}$heteroaryl, C$_6$-C$_{30}$aryl, or C$_6$-C$_{30}$aryl which is substituted by E, C$_1$-C$_{18}$alkyl; or C$_1$-C$_{18}$alkyl which is optionally substituted by E and optionally interrupted by D;
D is —CO—; —COO—; —OCOO—; —S—; —SO—; —SO$_2$—; —O—; —NR$^5$—; SiR$^5$R$^6$—; —POR$^5$—; —CR$^9$=CR$^{10}$—; or —C≡C—;
E is —OR$^5$; —SR$^5$; —NR$^5$R$^6$; —COR$^8$; —COOR$^7$; —CONR$^5$R$^6$; —CN; or halogen, especially F, or Cl; wherein R$^5$ and R$^6$ are independently of each other C$_6$-C$_{18}$aryl; C$_6$-C$_{18}$aryl which is substituted by C$_1$-C$_{18}$alkyl, C$_1$-C$_{18}$alkyl; or C$_1$-C$_{18}$alkyl which is interrupted by —O—; wherein R$^5$ and R$^6$ together optionally form a five or six membered ring, $R^7$ is $C_6$-$C_{18}$aryl; $C_6$-$C_{18}$aryl which is substituted by $C_1$-$C_{18}$alkyl, $C_1$-$C_{18}$alkyl; or $C_1$-$C_{18}$alkyl which is interrupted by —O—;

$R^8$ is $C_7$-$C_{12}$alkylaryl; $C_1$-$C_{18}$alkyl; or $C_1$-$C_{18}$alkyl which is interrupted by —O—; and $R^9$ and $R^{10}$ are independently of each other H, $C_6$-$C_{18}$aryl; $C_6$-$C_{18}$aryl which is substituted by $C_1$-$C_{18}$alkyl, $C_1$-$C_{18}$alkyl; or $C_1$-$C_{18}$alkyl which is interrupted by —O—;

(ii) W and Y are independently

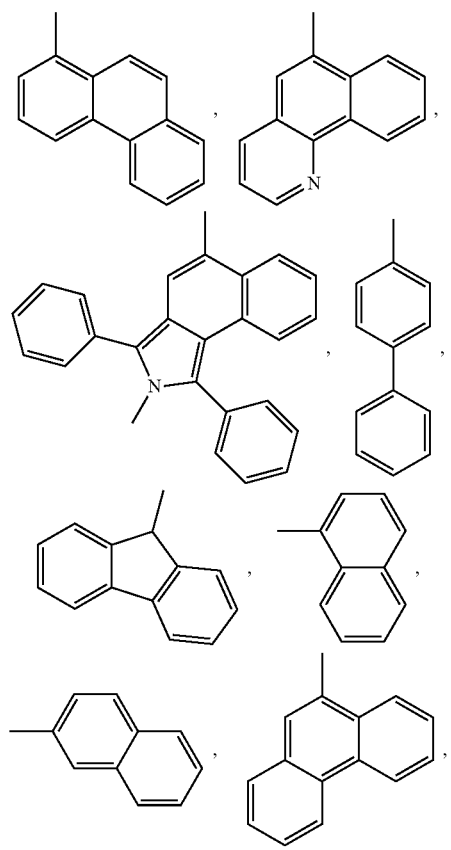

-continued

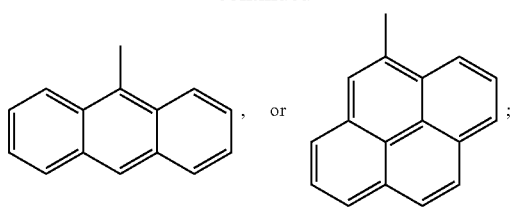

or (iii) W and Y are independently

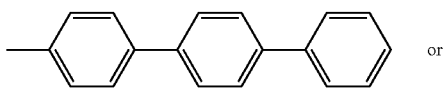

or

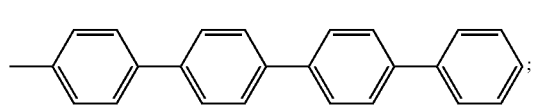

and X is

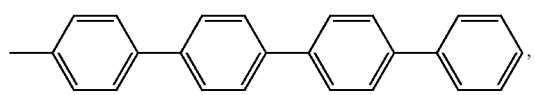

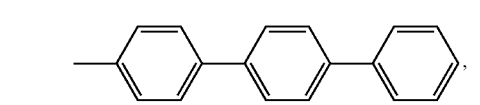

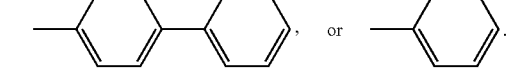

* * * * *